US006927318B2

(12) United States Patent
Ramesh et al.

(10) Patent No.: US 6,927,318 B2
(45) Date of Patent: Aug. 9, 2005

(54) WIP, A WASP-ASSOCIATED PROTEIN

(75) Inventors: Narayanaswamy Ramesh, Wayland, MA (US); Miguel A. de la Fuente, Boston, MA (US); Ines M. Anton, Turin (IT); Raif S. Geha, Belmont, MA (US)

(73) Assignee: The Children's Medical Center Corporation, Boston, MA (US)

( * ) Notice: Subject to any disclaimer, the term of this patent is extended or adjusted under 35 U.S.C. 154(b) by 0 days.

(21) Appl. No.: 10/078,547

(22) Filed: Feb. 19, 2002

(65) Prior Publication Data

US 2002/0199211 A1 Dec. 26, 2002

Related U.S. Application Data

(63) Continuation-in-part of application No. 09/599,287, filed on Jun. 22, 2000, which is a continuation of application No. PCT/US98/27501, filed on Dec. 22, 1998.
(60) Provisional application No. 60/101,457, filed on Sep. 23, 1998, and provisional application No. 60/068,533, filed on Dec. 23, 1997.

(51) Int. Cl.⁷ .......................... C12N 15/00; C12N 5/00; A01K 67/00; A01K 67/027
(52) U.S. Cl. ............................ 800/21; 800/13; 800/18; 800/22; 800/25; 435/325
(58) Field of Search ............................ 800/13, 18, 21, 800/22, 25, 8, 9, 14; 435/325

(56) References Cited

FOREIGN PATENT DOCUMENTS

| GB | 2 311 783 A | 8/1997 |
|---|---|---|
| WO | WO 99/32628 | 7/1999 |

OTHER PUBLICATIONS

Houdebine, L–M., 2002, Journal of Biotechnology, vol. 98, p. 145–160.*
Kappel et al., 1992, Current Opinion in Biotechnology, vol. 3, p. 548–553.*
Wu et al., 1997, Methods in Gene Biotechnology, CRC Press, Boca Raton, p. 339–365.*
Houdebine, 1994, Journal of Biotechnology, vol. 34, p. 269–287.*
Seamark, 1994, Reprod. Fertil. Dev., vol. 6, p. 653–657.*
Moreadith et al., 1997, Journal of Molecular Medicine, vol. 75, p. 208–216.*
Wolfer et al., 2002, Trends in Neurosciences, vol. 25, No. 7, p. 336–340.*
Sigmund, Jun. 2000, Arterioscler. Thromb. Vasc. Biol., p. 1425–1429.*
Attwood, T.K., "The Babel of Bioinformatics," *Science,* 290(5491):471–473 (2000).

Skolnick, J., et al., "From Genes to Protein Structure and Function: Novel Applications of Computational Approaches in the Genomic Era," *Trends Biotechnol.,* 18(1):34–9 (2000).
Anton, Ines, M., et al., "WIP (WASP Interacting Protein) deficiency reveals a differential role for WIP and the actin cytoskeleton in T and B cell activation", (abstract 66) Workshop on Molecular Basis of Human Congenital Lymphocyte Disorders, Dec. 3–5, 2001).
GenBank Accession No. AA501229, dbEST Id: 1145859, Clone Id: IMAGE: 891622 (5')1997.
Kreideweiss, S. et al., "H.sapiens mRNA for PRPL–2 protein", GenBank Accession No.:X86019, Locus: HSPRPL2 (Jan. 6, 1998).
Ramesh, N. et al., "Identification of a novel protein that interacts with Wiskott–Aldrich syndrome protein (WASP) .", *Journal of Allergy and Clinical Immunology* vol. 99, No. 1, Part 2, PS18Q (Jan. 1997); Joint meeting of the American Academy of Allergy, Asthma and Immunology, The American Association of Immunologists and The Clinic Immunology Society San Francisco, California, US Feb. 21–26, 1997; Abstract No. 727.
Ruhlmann, A. et al., "Gene from: H.sapiens mRNA for PRPL–2 protein", GenBank Accession No.: 762950, Locus: 762950 (Apr. 4, 1995).
Ruhlmann, A. et al., "H.sapiens mRNA for PRPL–2 protein", GenBank Accession No.:X86019, Locus HSPRPL2, (Apr. 4, 1995).
Ruhlmann, A. et al., "prpL__2 gene product", GenBank Accession No.: 762951, Locus: 762951 (Apr. 4, 1995).
Stewart, D.M. et al., "Homo sapiens Wiskott–Aldrich syndrome protein interacting protein (WASPIP) mRNA, partial cds.", GenBank Accession No.: AF106062, Locus: AF106062 (Jul. 31, 1999).
Antón, I.M. et al., "The Wiskott–Aldrich Syndrome Protein–interacting Protein (WIP) Binds to the Adaptor Protein Nck", *J. Biol. Chem.*273 (33):20992–20995 (1998).
Hanin, S. et al., "Wiskott–Aldrich syndrome protein (WASp) is a binding partner for c–Src family protein–tyrosiine kinases", *Curr. Biol.* 6(8):981–988 (1996).
Cooper, M.D. et al., "Wiskott–Aldrich Syndrome: An Immunologic Deficiency Disease Involving the Afferent Limb of Immunity", *Am. J. Med.* 44:499–513 (1968).

(Continued)

*Primary Examiner*—Shin-Lin Chen
(74) *Attorney, Agent, or Firm*—Hamilton, Brook, Smith & Reynolds, P.C.

(57) ABSTRACT

Described herein is a novel gene and its product, WIP, which associates with WASP. The subject invention relates to the isolated WIP gene or cDNA and transgenic mammals that have the WIP gene disrupted in their genome. Also the subject of this invention are methods of treating conditions or diseases in which WIP and/or WASP DNA or protein is deficient and/or defective, for example, mutated or altered, such that an individual is adversely affected. Also described are methods of altering or regulating WIP and its functions in a mammal or in a cell of a mammal, for example in a lymphocyte. A further subject of this invention is an assay to identify drugs which alter the activity of WIP or expression of WIP DNA.

30 Claims, 13 Drawing Sheets

OTHER PUBLICATIONS

Donnelly, S. F. H. et al., "A proline–rich protein, verprolin, involved in cytoskeletal organization and cellular growth in the yeast *Saccharomyces cerevisiae*", *Mol. Microbiol.* 10(3):585–596 (1993).

Featherstone, C., "The Many Faces of WAS Protein", *Science* 275:27–28 (1997).

Gertler, F. B. et al., "Mena, a Relative of VASP and Drosophila Enabled, Is Implicated in the Control of Microfilament Dynamics", *Cell* 87(2):227–239 (1996).

Kolluri, R. et al., "Direct interaction of the Wiskott–Aldrich syndrome protein with the GTPase Cdc42", *Proc. Natl. Acad. Sci. USA* 93:5615–5618 (1996).

Lehmann, J. M. et al., "Nck, a melanoma cDNA encoding a crytoplasmic protein consisting of the src homology units SH2 and SH3", *Nucleic Acids Research* 18(4):1048 (1990).

Meisenhelder, J. and T. Hunter, "The SH2/SH3 Domain–Containing Protein Nck Is Recognized by Certain Anti–Phospholipase C–γ1 Monoclonal Antibodies, And Its Phosphorylation on Tyrosine Is Stimulated by Platelet–Derived Growth Factor and Epidermal Growth Factor Treatment", *Molecular and Cellular Biology* 12(12):5843–5856 (1992).

Prasad, K. V. et al., "Src–homology 3 domain of protein kinase $p59^{fyn}$ mediates binding to phosphatidylinositol 3–kinase in T cells", *Proc. Natl. Acad. Sci. USA* 90:7366–7370 (1993).

Purich, D. L. and F. S. Southwick, "ABM–1 and ABM–2 Homology Sequences: Consensus Docking Sites for Actin–Based Motility Defined by Oligoproline Regions in Listeria ActA Surface Protein and Human VASP", *Biochem. and Biophys. Res. Commun.* 231:686–691 (1997).

Ramesh, N. et al., "WIP, a protein associated with Wiskott–Aldrich syndrome protein, induces actin polymerization and redistribution in lymphoid cells", *Proc. Natl. Acad. Sci USA* 94:14671–14676 (1997).

Reinhard, M. et al., "The proline–rich focal adhesion and microfilament protein VASP is a ligand for profilins", *The EMBO Journal* 14(8):1583–1589 (1995).

Rivero–Lezcano, O. M. et al., "Wiskott–Aldrich Syndrome Protein Physically Associates with Nck through Src Homology 3 Domains", *Mol. Cell. Biol.* 15(10):5725–5731 (1995).

Stewart, D. M. et al., "Mutations That Cause the Wiskott–Aldrich Syndrome Impair the Interaction of Wiskkott–Aldrich Syndrome Protein (WASP) with WASP Interacting Protein", *J. Immunol.* 162:5019–5024 (1999).

Symons, M. et al., "Wiskott–Aldrich Syndrome Protein, a Novel Effector for the GTPase CDC42Hs, Is Implicated in Actin Polymerization", *Cell* 84(5):723–734 (1996).

Theriot, J. A. and T.J. Mitchison, "The Three Faces of Profilin", *Cell* 75(5):835–838 (1993).

Troys, M. V. et al., "The actin binding site of thymosin β4 mapped by mutational analysis", *The EMBO Journal* 15(2):201–210 (1996).

Vaduva, G. et al., "The Human WASP–interacting Protein, WIP, Activates the Cell Polarity Pathway in Yeast", *J. Biol. Chem.* 274(24):17103–17108 (1999).

Vaduva, G. et al., "Wiskott–Aldrich Syndrome Protein interacting protein, WIP, complements veprolin function in yeast cells", Poster presented at the $14^{th}$ Annual Symposium in Cellular Endocrinology; Cellular Signaling & the Cytoskeleton, Sep. 1998.

Antón, I.M. et al.,"The Wiskott–Aldrich Syndrome Protein–Interacting Protein (WIP) Binds to the Adaptor Protein Nck and Induces Actin Clusters After PDGF Stimulation", Poster presented at the $14^{th}$ Annual Symposium in Cellular Endocrinology; Cellular Singaling & the Cytoskeleton, Sep. 1998.

Meinkoth, J., et al., "Hybridization of Nucleic Acids Immobilized on Solid Supports," *Anal Biochem.*, 138(2):267–284.

Ngo, J.T., et al., "Computational complexity, protein structure predication, and the Levinthal paradox in The Protein Folding Problem," Ch. 14, pp. 435–508, *Birkhauser*, 1994.

Antón l.M., et al., "WIP Deficiency Reveals a Differential Role for WIP and the Actin Cytoskeleton in T and B Cell Activation," *Immunity*, 16:1–20 (2002).

GenBank Accession No. B65694, dbGSS Id: 65846, Clone Id: 2022M15 1998.

Ramesh, N. et al., "Identification of a novel protein that interacts with Wiskott–Aldrich syndrome protein (WASP)", Redacted abstract submission form for the AAAI/AAI/CIS Joint Meeting (Feb. 21–26, 1997); submitted to AAI; Abstract published Jan. 1997 (see Ref. AT).

Zhang, J., et al., "Antigen Receptor–induced Activation and Cytoskeletal Rearrangement Are Impaired in Wiskott–Aldrich Syndrome Protein–deficient Lymphocytes," *J. Exp. Med.*, 190(9):1329–1341 (1999).

Savoy, D.M., et al., "Cutting Edge: WIP, a Binding Partner for Wiskott–Aldrich Syndrome Protein, Cooperates with Vav in the Regulation of T Cell Activation," *J. of Immunology* 164:2866–2870 (2000).

Martinez–Quiles, N., et al., "WIP regulates N–WASP–mediated actin polymorization and filopodium formation," *Nature Cell Biology* 3(5):484–491 (2001).

Snapper, S.B., et al., "Wiskott–Aldrich Syndrome Protein–Deficient Mice Reveal a Role for WASP in T but Not B Cell Activation," *Immunity* 9:81–91 (1998).

* cited by examiner

```
ccc ggg cag gtt aga aga cag cag ggg aac tcg aga agt tgg ttg ttt      48
Pro Gly Gln Val Arg Arg Gln Gln Gly Asn Ser Arg Ser Trp Leu Phe
 1               5                  10                  15
tca gca gat taa aac aat aca gat tta tca gca aga ctg ttc aac gca      96
Ser Ala Asp OCH Asn Asn Thr Asp Leu Ser Ala Arg Leu Phe Asn Ala
                 20                  25                  30
taa ctg ccc aag atg cct gtc cct ccc cct cca gca ccc ccg ccg ccc     144
OCH Leu Pro Lys Met Pro Val Pro Pro Pro Ala Pro Pro Pro Pro
             35                  40                  45
ccg acg ttt gca ctg gcc aat aca gag aag cct acc ttg aat aag aca     192
Pro Thr Phe Ala Leu Ala Asn Thr Glu Lys Pro Thr Leu Asn Lys Thr
             50                  55                  60
gag cag gct ggg aga aat gct ctc ctt tct gat atc agc aaa ggg aag     240
Glu Gln Ala Gly Arg Asn Ala Leu Leu Ser Asp Ile Ser Lys Gly Lys
             65                  70                  75
aaa cta aag aag acg gtc acc aat gac aga agt gca cca ata ctg gac     288
Lys Leu Lys Lys Thr Val Thr Asn Asp Arg Ser Ala Pro Ile Leu Asp
         80                  85                  90
aaa cct aaa gga gct ggt gct gga ggc ggt ggt ggt ggc ttt ggt gga     336
Lys Pro Lys Gly Ala Gly Ala Gly Gly Gly Gly Gly Gly Phe Gly Gly
 95                 100                 105                 110
ggc ggc gga ttt ggc gga gga ggt ggt ggc gga ggc ggt gga aGT TTT     384
Gly Gly Gly Phe Gly Gly Gly Gly Gly Gly Gly Gly Gly Gly Ser Phe
                115                 120                 125
GGA GGG GGC GGA CCT CCA GGT CTG GGA GGA TTG TTC CAG GCT GGA ATG     432
Gly Gly Gly Gly Pro Pro Gly Leu Gly Gly Leu Phe Gln Ala Gly Met
             130                 135                 140
CCG AAG CTG AGA TCC ACC GCC AAC AGG GAT AAT GAT TCT GGA GGA AGC     480
Pro Lys Leu Arg Ser Thr Ala Asn Arg Asp Asn Asp Ser Gly Gly Ser
             145                 150                 155
CGA CCA CCA TTG TTG CCA CCG GGA GGA AGA TCC ACA TCT GCG AAA CCC     528
Arg Pro Pro Leu Leu Pro Pro Gly Gly Arg Ser Thr Ser Ala Lys Pro
         160                 165                 170
TTT TCA CCC CCA AGT GGC CCA GGG AGG TTT CCT GTG CCT TCT CCA GGC     576
Phe Ser Pro Pro Ser Gly Pro Gly Arg Phe Pro Val Pro Ser Pro Gly
175                 180                 185                 190
CAC AGA AGT GGT CCC CCA GAG CCT CAG AGG AAC CGA ATG CCG CCC CCA     624
His Arg Ser Gly Pro Pro Glu Pro Gln Arg Asn Arg Met Pro Pro Pro
                195                 200                 205
AGG CCC GAC GTG GGC TCA AAG CCT GAT AGC ATT CCT CCT CCA GTA CCT     672
Arg Pro Asp Val Gly Ser Lys Pro Asp Ser Ile Pro Pro Pro Val Pro
             210                 215                 220
AGT ACT CCA AGA CCC ATT CAA TCA AGT CTG CAC AAC CGG GGG TCC CCA     720
Ser Thr Pro Arg Pro Ile Gln Ser Ser Leu His Asn Arg Gly Ser Pro
             225                 230                 235
CCA GTG CCC GGA GGC CCC AGG CAG CCC AGC CCC GGG CCC ACT CCT CCC     768
Pro Val Pro Gly Gly Pro Arg Gln Pro Ser Pro Gly Pro Thr Pro Pro
             240                 245                 250
CCT TTC CCT GGA AAC CGC GGC ACT GCT TTG GGA GGA GGC TCA ATA CGT     816
Pro Phe Pro Gly Asn Arg Gly Thr Ala Leu Gly Gly Gly Ser Ile Arg
255                 260                 265                 270
CAG TCC CCC TTG AGC TCC TCC TCG CCC TTC TCC AAC CGG CCT CCC CTC     864
Gln Ser Pro Leu Ser Ser Ser Ser Pro Phe Ser Asn Arg Pro Pro Leu
                275                 280                 285
CCG CCT ACC CCC AGC AGG GCG TTG GAT GAC AAA CCC CCT CCA CCA CCT     912
Pro Pro Thr Pro Ser Arg Ala Leu Asp Asp Lys Pro Pro Pro Pro Pro
             290                 295                 300
```

FIG. 1A

```
CCT CCA GTG GGC AAC AGG CCC TCC ATC CAC AGG GAA GCG GTT CCC CCT    960
Pro Pro Val Gly Asn Arg Pro Ser Ile His Arg Glu Ala Val Pro Pro
        305                 310                 315
CCT CCT CCT CAG AAC AAC AAG CCT CCA GTG CCT TCC ACT CCG CGG CCT   1008
Pro Pro Pro Gln Asn Asn Lys Pro Pro Val Pro Ser Thr Pro Arg Pro
        320                 325                 330
TCG GCT CCT CAC AGG CCC CAC CTC CGC CCG CCA CCT CCC AGC AGG CCC   1056
Ser Ala Pro His Arg Pro His Leu Arg Pro Pro Pro Ser Arg Pro
335                 340                 345                 350
GGG CCG CCT CCT CTG CCT CCA AGT TCC AGC GGC AAT GAC GAA ACC CCA   1104
Gly Pro Pro Pro Leu Pro Pro Ser Ser Ser Gly Asn Asp Glu Thr Pro
                355                 360                 365
AGA CTC CCA CAG CGG AAT CTG TCC CTC AGT TCG TCC ACG CCC CCG TTA   1152
Arg Leu Pro Gln Arg Asn Leu Ser Leu Ser Ser Ser Thr Pro Pro Leu
        370                 375                 380
CCT TCG CCA GGA CGT TCA GGT CCT CTT CCT CCC CCA GTG CCC AGT GAG   1200
Pro Ser Pro Gly Arg Ser Gly Pro Leu Pro Pro Pro Val Pro Ser Glu
        385                 390                 395
AGA CCC CCA CCT CCA GTG AGG GAC CCG CCA GGC CGA TCA GGC CCC CTC   1248
Arg Pro Pro Pro Pro Val Arg Asp Pro Pro Gly Arg Ser Gly Pro Leu
        400                 405                 410
CCA CCA CCT CCT CCA GTA AGC AGA AAC GGC AGC ACA TCT CGG GCC CTG   1296
Pro Pro Pro Pro Pro Val Ser Arg Asn Gly Ser Thr Ser Arg Ala Leu
415                 420                 425                 430
CCT GCT ACC CCT CAG TTG CCA TCC AGG AGT GGA GTA GAC AGT CCC AGG   1344
Pro Ala Thr Pro Gln Leu Pro Ser Arg Ser Gly Val Asp Ser Pro Arg
                435                 440                 445
AGT GGA CCC AGG CCT CCC CTT CCT CCT GAT AGG CCC AGT GCT GGG GCA   1392
Ser Gly Pro Arg Pro Pro Leu Pro Pro Asp Arg Pro Ser Ala Gly Ala
        450                 455                 460
CCT CCC CCA CCT CCA CCA TCA ACA TCT ATT AGA AAT GGC TTC CAA GAC   1440
Pro Pro Pro Pro Pro Pro Ser Thr Ser Ile Arg Asn Gly Phe Gln Asp
        465                 470                 475
TCT CCA TGT GAA GAT GAG TGG GAA AGC AGA TTC TAC TTC CAT CCG ATT   1488
Ser Pro Cys Glu Asp Glu Trp Glu Ser Arg Phe Tyr Phe His Pro Ile
        480                 485                 490
TCC GAT TTG CCA CCT CCA GAG CCA TAT GTA CAA ACG ACC AAA AGT TAT   1536
Ser Asp Leu Pro Pro Pro Glu Pro Tyr Val Gln Thr Thr Lys Ser Tyr
495                 500                 505                 510
CCC AGC AAA CTG GCA AGA AAC GAA AGC CGG AGT Gga tcc aac cga aga   1584
Pro Ser Lys Leu Ala Arg Asn Glu Ser Arg Ser Gly Ser Asn Arg Arg
                515                 520                  525
gaa agg ggt ggt cca cca ctc cct ccc atc ccg agg tga tct ttg gct   1632
Glu Arg Gly Gly Pro Pro Leu Pro Pro Ile Pro Arg OPA Ser Leu Ala
                530                 535                 540
gct ctt ctc tac cca agc tca aga gct gct tct gtt ggt atc taa gaa   1680
Ala Leu Leu Tyr Pro Ser Ser Arg Ala Ala Ser Val Gly Ile OCH Glu
                545                 550                 555
ctg gat acc ctc ccc cct                                           1698
Leu Asp Thr Leu Pro Pro
                560
```

FIG. 1B

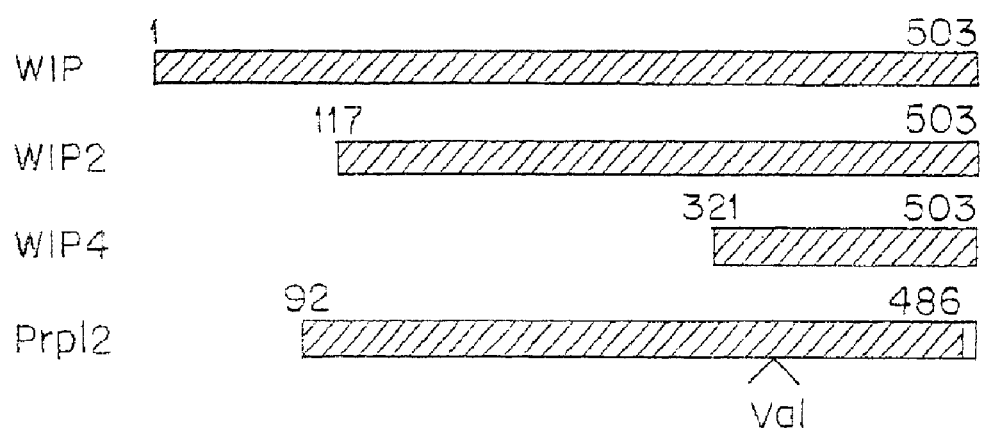
FIG. IC

```
              ***   ***
  1     MPVPPPPAPP PPPTFALANT EKPTLNKTEQ AGRNALLSDI

SKGKKLKKTV TNDRSAPILD KPKGAGAGGG GGGFGGGGGF

81     GGGGGGGGGG SFGGGGPPGL GGLFQAGMPK LRSTANRDND

SGGSRPPLLP PGGRSTSAKP FSPPSGPGRF PVPSPGHRSG

161     PPEPQRNRMP PPRPDVGSKP DSIPPPVPST PRPIQSSLHN

RGSPPVPGGP RQPSPGPTPP PFPGNRGTAL GGSIRQSPL

241     SSSSPFSNRP PLPPTPSRAL DDKPPPPPPP VGNRPSIHRE

AVPPPPPQNN KPPVPSTPRP SAPHRPHLRP PPPSRPGPPP

321     LPPSSSGNDE TPRLPQRNLS LSSSTPPLPS PGRSGPLPPP

PSERPPPPVR DPPGRSGPLP PPPPVSRNGS TSRALPATPQ

****  **
401     LPSRSGVDSP RSGPRPPLPP DRPSAGAPPP PPPSTSIRNG

FQDSPCEDEW ESRFYFHPIS DLPPPEPYVQ TTKSYPSKLA

481     RNESRSGSNR RERGGPPLPP IPR
```

FIG. 1D

```
WIP   1   MPVPPPPAPPPPPTEFALANTEKPTLNKTEQA  GRNALLSDISKGKKLKKTVTNDRSAPILD
          |::::|.|::|..||||||            . |||||.|||||||.||||..||||||||
Verp  1   MAGAPAPPPPPPPALGGSAPKPA..KSVMQ    GRDALLGDIRKGMKLKKAEFNDRSAPIV.

WIP  61   KPKGAGAGGGGGGFGGGGGGGGFGGGGGGGGSFGGG       GPPGLGGLFQAGMPKLR
          |::      |.:|:|:                    |      |.|  :.:.|||:|
Verp 57   ....GGGVVSSASGSSGTVSSKGPSMSAPPIPGM         GAPQLGDILAGGIPKLK
```

FIG. 1E

| | | | | | | | | | | |
|---|---|---|---|---|---|---|---|---|---|---|
| WIP | 352-361 | G | R | S | G | P | L | P | P | P |
| WIP | 374-383 | G | R | S | G | P | L | P | P | P |
| WIP | 410-419 | P | R | S | G | P | R | P | L | P |
| WASP | 338-347 | G | R | S | G | P | L | P | P | V | P |
| WASP | 376-385 | G | R | S | G | P | L | P | P | P |
| Consensus | | G | R | S | G | P | X | P | P | X | P |

FIG. 1F

Targeting construct

Targeted allele

SEQUENCE LISTING

```
<160> NUMBER OF SEQ ID NOS: 27

<210> SEQ ID NO 1
<211> LENGTH: 1698
<212> TYPE: DNA
<213> ORGANISM: Human
<220> FEATURE:
<221> NAME/KEY: CDS
<222> LOCATION: (1)...(1698)

<400> SEQUENCE: 1 ccc ggg cag gtt aga aga cag cag ggg aac tcg aga agt tgg ttg ttt      48
Pro Gly Gln Val Arg Arg Gln Gln Gly Asn Ser Arg Ser Trp Leu Phe
 1               5                  10                  15 tca gca gat taa aac aat aca gat tta tca gca aga ctg ttc aac gca      96
Ser Ala Asp  *  Asn Asn Thr Asp Leu Ser Ala Arg Leu Phe Asn Ala
                20                  25                  30 taa ctg ccc aag atg cct gtc cct ccc cct cca gca ccc ccg ccg ccc     144
 *  Leu Pro Lys Met Pro Val Pro Pro Pro Ala Pro Pro Pro Pro
             35                  40                  45 ccg acg ttt gca ctg gcc aat aca gag aag cct acc ttg aat aag aca     192
Pro Thr Phe Ala Leu Ala Asn Thr Glu Lys Pro Thr Leu Asn Lys Thr
             50                  55                  60 gag cag gct ggg aga aat gct ctc ctt tct gat atc agc aaa ggg aag     240
Glu Gln Ala Gly Arg Asn Ala Leu Leu Ser Asp Ile Ser Lys Gly Lys
         65                  70                  75 aaa cta aag aag acg gtc acc aat gac aga agt gca cca ata ctg gac     288
Lys Leu Lys Lys Thr Val Thr Asn Asp Arg Ser Ala Pro Ile Leu Asp
     80                  85                  90 aaa cct aaa gga gct ggt gct gga ggc ggt ggt ggt ggc ttt ggt gga     336
Lys Pro Lys Gly Ala Gly Ala Gly Gly Gly Gly Gly Gly Phe Gly Gly
 95                 100                 105                 110 ggc ggc gga ttt ggc gga gga ggt ggt ggc gga ggc ggt gga agt ttt     384
Gly Gly Gly Phe Gly Gly Gly Gly Gly Gly Gly Gly Gly Ser Phe
                115                 120                 125
```

-continued

| | |
|---|---|
| gga ggg ggc gga cct cca ggt ctg gga gga ttg ttc cag gct gga atg<br>Gly Gly Gly Gly Pro Pro Gly Leu Gly Gly Leu Phe Gln Ala Gly Met<br>          130                      135                    140 | 432 |
| ccg aag ctg aga tcc acc gcc aac agg gat aat gat tct gga gga agc<br>Pro Lys Leu Arg Ser Thr Ala Asn Arg Asp Asn Asp Ser Gly Gly Ser<br>        145                      150                      155 | 480 |
| cga cca cca ttg ttg cca ccg gga gga aga tcc aca tct gcg aaa ccc<br>Arg Pro Pro Leu Leu Pro Pro Gly Gly Arg Ser Thr Ser Ala Lys Pro<br>160                      165                      170 | 528 |
| ttt tca ccc cca agt ggc cca ggg agg ttt cct gtg cct tct cca ggc<br>Phe Ser Pro Pro Ser Gly Pro Gly Arg Phe Pro Val Pro Ser Pro Gly<br>175                      180                      185                    190 | 576 |
| cac aga agt ggt ccc cca gag cct cag agg aac cga atg ccg ccc cca<br>His Arg Ser Gly Pro Pro Glu Pro Gln Arg Asn Arg Met Pro Pro Pro<br>                195                      200                      205 | 624 |
| agg ccc gac gtg ggc tca aag cct gat agc att cct cct cca gta cct<br>Arg Pro Asp Val Gly Ser Lys Pro Asp Ser Ile Pro Pro Pro Val Pro<br>                210                      215                      220 | 672 |
| agt act cca aga ccc att caa tca agt ctg cac aac cgg ggg tcc cca<br>Ser Thr Pro Arg Pro Ile Gln Ser Ser Leu His Asn Arg Gly Ser Pro<br>        225                      230                      235 | 720 |
| cca gtg ccc gga ggc ccc agg cag ccc agc ccc ggg ccc act cct ccc<br>Pro Val Pro Gly Gly Pro Arg Gln Pro Ser Pro Gly Pro Thr Pro Pro<br>240                      245                      250 | 768 |
| cct ttc cct gga aac cgc ggc act gct ttg gga gga ggc tca ata cgt<br>Pro Phe Pro Gly Asn Arg Gly Thr Ala Leu Gly Gly Gly Ser Ile Arg<br>255                      260                      265                    270 | 816 |
| cag tcc ccc ttg agc tcc tcc tcg ccc ttc tcc aac cgg cct ccc ctc<br>Gln Ser Pro Leu Ser Ser Ser Ser Pro Phe Ser Asn Arg Pro Pro Leu<br>                275                      280                      285 | 864 |
| ccg cct acc ccc agc agg gcg ttg gat gac aaa ccc cct cca cca cct<br>Pro Pro Thr Pro Ser Arg Ala Leu Asp Asp Lys Pro Pro Pro Pro Pro<br>                290                      295                      300 | 912 |
| cct cca gtg ggc aac agg ccc tcc atc cac agg gaa gcg gtt ccc cct<br>Pro Pro Val Gly Asn Arg Pro Ser Ile His Arg Glu Ala Val Pro Pro<br>                305                      310                      315 | 960 |
| cct cct cct cag aac aac aag cct cca gtg cct tcc act ccg cgg cct<br>Pro Pro Pro Gln Asn Asn Lys Pro Pro Val Pro Ser Thr Pro Arg Pro<br>320                      325                      330 | 1008 |
| tcg gct cct cac agg ccc cac ctc cgc ccg cca cct ccc agc agg ccc<br>Ser Ala Pro His Arg Pro His Leu Arg Pro Pro Pro Pro Ser Arg Pro<br>335                      340                      345                    350 | 1056 |
| ggg ccg cct cct ctg cct cca agt tcc agc ggc aat gac gaa acc cca<br>Gly Pro Pro Pro Leu Pro Pro Ser Ser Ser Gly Asn Asp Glu Thr Pro<br>                355                      360                      365 | 1104 |
| aga ctc cca cag cgg aat ctg tcc ctc agt tcg tcc acg ccc ccg tta<br>Arg Leu Pro Gln Arg Asn Leu Ser Leu Ser Ser Ser Thr Pro Pro Leu<br>                370                      375                      380 | 1152 |
| cct tcg cca gga cgt tca ggt cct ctt cct ccc cca gtg ccc agt gag<br>Pro Ser Pro Gly Arg Ser Gly Pro Leu Pro Pro Pro Val Pro Ser Glu<br>        385                      390                      395 | 1200 |
| aga ccc cca cct cca gtg agg gac ccg cca ggc cga tca ggc ccc ctc<br>Arg Pro Pro Pro Pro Val Arg Asp Pro Pro Gly Arg Ser Gly Pro Leu<br>400                      405                      410 | 1248 |
| cca cca cct cct cca gta agc aga aac ggc agc aca tct cgg gcc ctg<br>Pro Pro Pro Pro Pro Val Ser Arg Asn Gly Ser Thr Ser Arg Ala Leu<br>415                      420                      425                    430 | 1296 |
| cct gct acc cct cag ttg cca tcc agg agt gga gta gac agt ccc agg<br>Pro Ala Thr Pro Gln Leu Pro Ser Arg Ser Gly Val Asp Ser Pro Arg | 1344 |

-continued

```
                       435                 440                 445
agt gga ccc agg cct ccc ctt cct cct gat agg ccc agt gct ggg gca    1392
Ser Gly Pro Arg Pro Pro Leu Pro Pro Asp Arg Pro Ser Ala Gly Ala
            450                 455                 460 cct ccc cca cct cca cca tca aca tct att aga aat ggc ttc caa gac    1440
Pro Pro Pro Pro Pro Ser Thr Ser Ile Arg Asn Gly Phe Gln Asp
        465                 470                 475 tct cca tgt gaa gat gag tgg gaa agc aga ttc tac ttc cat ccg att    1488
Ser Pro Cys Glu Asp Glu Trp Glu Ser Arg Phe Tyr Phe His Pro Ile
    480                 485                 490 tcc gat ttg cca cct cca gag cca tat gta caa acg acc aaa agt tat    1536
Ser Asp Leu Pro Pro Pro Glu Pro Tyr Val Gln Thr Thr Lys Ser Tyr
495                 500                 505                 510 ccc agc aaa ctg gca aga aac gaa agc cgg agt gga tcc aac cga aga    1584
Pro Ser Lys Leu Ala Arg Asn Glu Ser Arg Ser Gly Ser Asn Arg Arg
            515                 520                 525 gaa agg ggt ggt cca cca ctc cct ccc atc ccg agg tga tct ttg gct    1632
Glu Arg Gly Gly Pro Pro Leu Pro Pro Ile Pro Arg  *  Ser Leu Ala
        530                 535                 540 gct ctt ctc tac cca agc tca aga gct gct tct gtt ggt atc taa gaa    1680
Ala Leu Leu Tyr Pro Ser Ser Arg Ala Ala Ser Val Gly Ile  *  Glu
    545                 550                 555 ctg gat acc ctc ccc cct                                            1698
Leu Asp Thr Leu Pro Pro
        560

<210> SEQ ID NO 2
<211> LENGTH: 503
<212> TYPE: PRT
<213> ORGANISM: Human

<400> SEQUENCE: 2

Met Pro Val Pro Pro Pro Ala Pro Pro Pro Pro Thr Phe Ala
1               5                   10                  15

Leu Ala Asn Thr Glu Lys Pro Thr Leu Asn Lys Thr Glu Gln Ala Gly
            20                  25                  30

Arg Asn Ala Leu Leu Ser Asp Ile Ser Lys Gly Lys Lys Leu Lys Lys
        35                  40                  45

Thr Val Thr Asn Asp Arg Ser Ala Pro Ile Leu Asp Lys Pro Lys Gly
    50                  55                  60

Ala Gly Ala Gly Gly Gly Gly Gly Phe Gly Gly Gly Gly Phe
65                  70                  75                  80

Gly Gly Gly Gly Gly Gly Gly Gly Ser Phe Gly Gly Gly
            85                  90                  95

Pro Pro Gly Leu Gly Gly Leu Phe Gln Ala Gly Met Pro Lys Leu Arg
        100                 105                 110

Ser Thr Ala Asn Arg Asp Asn Asp Ser Gly Gly Ser Arg Pro Pro Leu
    115                 120                 125

Leu Pro Pro Gly Gly Arg Ser Thr Ser Ala Lys Pro Phe Ser Pro Pro
130                 135                 140

Ser Gly Pro Gly Arg Phe Pro Val Pro Ser Gly His Arg Ser Gly
145                 150                 155                 160

Pro Pro Glu Pro Gln Arg Asn Arg Met Pro Pro Arg Pro Asp Val
            165                 170                 175

Gly Ser Lys Pro Asp Ser Ile Pro Pro Val Pro Ser Thr Pro Arg
        180                 185                 190

Pro Ile Gln Ser Ser Leu His Asn Arg Gly Ser Pro Pro Val Pro Gly
```

```
                195                 200                 205
Gly Pro Arg Gln Pro Ser Pro Gly Pro Thr Pro Pro Phe Pro Gly
    210                 215                 220

Asn Arg Gly Thr Ala Leu Gly Gly Gly Ser Ile Arg Gln Ser Pro Leu
225                 230                 235                 240

Ser Ser Ser Ser Pro Phe Ser Asn Arg Pro Pro Leu Pro Pro Thr Pro
                245                 250                 255

Ser Arg Ala Leu Asp Asp Lys Pro Pro Pro Pro Pro Val Gly
            260                 265                 270

Asn Arg Pro Ser Ile His Arg Glu Ala Val Pro Pro Pro Pro Gln
        275                 280                 285

Asn Asn Lys Pro Pro Val Pro Ser Thr Pro Arg Pro Ser Ala Pro His
290                 295                 300

Arg Pro His Leu Arg Pro Pro Pro Ser Arg Pro Gly Pro Pro Pro
305                 310                 315                 320

Leu Pro Pro Ser Ser Ser Gly Asn Asp Glu Thr Pro Arg Leu Pro Gln
                325                 330                 335

Arg Asn Leu Ser Leu Ser Ser Ser Thr Pro Pro Leu Pro Ser Pro Gly
            340                 345                 350

Arg Ser Gly Pro Leu Pro Pro Pro Ser Glu Arg Pro Pro Pro
        355                 360                 365

Val Arg Asp Pro Pro Gly Arg Ser Gly Pro Leu Pro Pro Pro Pro Pro
    370                 375                 380

Val Ser Arg Asn Gly Ser Thr Ser Arg Ala Leu Pro Ala Thr Pro Gln
385                 390                 395                 400

Leu Pro Ser Arg Ser Gly Val Asp Ser Pro Arg Ser Gly Pro Arg Pro
                405                 410                 415

Pro Leu Pro Pro Asp Arg Pro Ser Ala Gly Ala Pro Pro Pro Pro
            420                 425                 430

Pro Ser Thr Ser Ile Arg Asn Gly Phe Gln Asp Ser Pro Cys Glu Asp
        435                 440                 445

Glu Trp Glu Ser Arg Phe Tyr Phe His Pro Ile Ser Asp Leu Pro Pro
450                 455                 460

Pro Glu Pro Tyr Val Gln Thr Thr Lys Ser Tyr Pro Ser Lys Leu Ala
465                 470                 475                 480

Arg Asn Glu Ser Arg Ser Gly Ser Asn Arg Arg Glu Arg Gly Gly Pro
                485                 490                 495

Pro Leu Pro Pro Ile Pro Arg
            500

<210> SEQ ID NO 3
<211> LENGTH: 6
<212> TYPE: PRT
<213> ORGANISM: unknown
<220> FEATURE:
<223> OTHER INFORMATION: profilin motif

<400> SEQUENCE: 3

Ala Pro Pro Pro Pro Pro
 1               5

<210> SEQ ID NO 4
<211> LENGTH: 4
<212> TYPE: PRT
<213> ORGANISM: unknown
<220> FEATURE:
<223> OTHER INFORMATION: actin-binding motif
```

```
<400> SEQUENCE: 4

Lys Leu Lys Lys
  1

<210> SEQ ID NO 5
<211> LENGTH: 112
<212> TYPE: PRT
<213> ORGANISM: unknown
<220> FEATURE:
<223> OTHER INFORMATION: N-terminal of WIP, human

<400> SEQUENCE: 5

Met Pro Val Pro Pro Pro Ala Pro Pro Pro Pro Thr Phe Ala
  1               5                  10                  15

Leu Ala Asn Thr Glu Lys Pro Thr Leu Asn Lys Thr Glu Gln Ala Gly
             20                  25                  30

Arg Asn Ala Leu Leu Ser Asp Ile Ser Lys Gly Lys Lys Leu Lys Lys
         35                  40                  45

Thr Val Thr Asn Asp Arg Ser Ala Pro Ile Leu Asp Lys Pro Lys Gly
     50                  55                  60

Ala Gly Ala Gly Gly Gly Gly Gly Phe Gly Gly Gly Gly Phe
 65                  70                  75                  80

Gly Gly Gly Gly Gly Gly Gly Gly Ser Phe Gly Gly Gly
                 85                  90                  95

Pro Pro Gly Leu Gly Gly Leu Phe Gln Ala Gly Met Pro Lys Leu Arg
                100                 105                 110

<210> SEQ ID NO 6
<211> LENGTH: 104
<212> TYPE: PRT
<213> ORGANISM: unknown
<220> FEATURE:
<223> OTHER INFORMATION: Saccharomyces cerevisiae, Verprolin N-terminal

<400> SEQUENCE: 6

Met Ala Gly Ala Pro Ala Pro Pro Pro Pro Pro Pro Ala Leu
  1               5                  10                  15

Gly Gly Ser Ala Pro Lys Pro Ala Lys Ser Val Met Gln Gly Arg Asp
             20                  25                  30

Ala Leu Leu Gly Asp Ile Arg Lys Gly Met Lys Leu Lys Lys Ala Glu
         35                  40                  45

Thr Asn Asp Arg Ser Ala Pro Ile Val Gly Gly Val Val Ser Ser
     50                  55                  60

Ala Ser Gly Ser Ser Gly Thr Val Ser Ser Lys Gly Pro Ser Met Ser
 65                  70                  75                  80

Ala Pro Pro Ile Pro Gly Met Gly Ala Pro Gln Leu Gly Asp Ile Leu
                 85                  90                  95

Ala Gly Gly Ile Pro Lys Leu Lys
                100

<210> SEQ ID NO 7
<211> LENGTH: 10
<212> TYPE: PRT
<213> ORGANISM: unknown
<220> FEATURE:
<223> OTHER INFORMATION: consensus sequence GRSGPXPPXP
<221> NAME/KEY: VARIANT
<222> LOCATION: (1)...(10)
<223> OTHER INFORMATION: Xaa = Any Amino Acid
<221> NAME/KEY: VARIANT
```

```
<222> LOCATION: 6, 9
<223> OTHER INFORMATION: Xaa = Any Amino Acid

<400> SEQUENCE: 7

Gly Arg Ser Gly Pro Xaa Pro Pro Xaa Pro
 1               5                  10

<210> SEQ ID NO 8
<211> LENGTH: 10
<212> TYPE: PRT
<213> ORGANISM: unknown
<220> FEATURE:
<223> OTHER INFORMATION: WIP sequence 352-361a.a., human

<400> SEQUENCE: 8

Gly Arg Ser Gly Pro Leu Pro Pro Pro Pro
 1               5                  10

<210> SEQ ID NO 9
<211> LENGTH: 10
<212> TYPE: PRT
<213> ORGANISM: unknown
<220> FEATURE:
<223> OTHER INFORMATION: WIP sequence 374-383 a.a., human

<400> SEQUENCE: 9

Gly Arg Ser Gly Pro Leu Pro Pro Pro Pro
 1               5                  10

<210> SEQ ID NO 10
<211> LENGTH: 10
<212> TYPE: PRT
<213> ORGANISM: unknown
<220> FEATURE:
<223> OTHER INFORMATION: WIP sequence 410-419 a.a., human

<400> SEQUENCE: 10

Pro Arg Ser Gly Pro Arg Pro Pro Leu Pro
 1               5                  10

<210> SEQ ID NO 11
<211> LENGTH: 10
<212> TYPE: PRT
<213> ORGANISM: unknown
<220> FEATURE:
<223> OTHER INFORMATION: WASP sequence 338-347 a.a.

<400> SEQUENCE: 11

Gly Arg Ser Gly Pro Leu Pro Pro Val Pro
 1               5                  10

<210> SEQ ID NO 12
<211> LENGTH: 10
<212> TYPE: PRT
<213> ORGANISM: unknown
<220> FEATURE:
<223> OTHER INFORMATION: WASP sequence 376-385 a.a.

<400> SEQUENCE: 12

Gly Arg Ser Gly Pro Leu Pro Pro Pro Pro
 1               5                  10

<210> SEQ ID NO 13
<211> LENGTH: 6
<212> TYPE: PRT
<213> ORGANISM: unknown
<220> FEATURE:
```

<223> OTHER INFORMATION: PPPPPP domain of WASP

<400> SEQUENCE: 13

Pro Pro Pro Pro Pro Pro
1               5

<210> SEQ ID NO 14
<211> LENGTH: 6
<212> TYPE: PRT
<213> ORGANISM: unknown
<220> FEATURE:
<223> OTHER INFORMATION: ABM-2 motif
<221> NAME/KEY: VARIANT
<222> LOCATION: (1)...(6)
<223> OTHER INFORMATION: Xaa = Any Amino Acid
<221> NAME/KEY: VARIANT
<222> LOCATION: 1
<223> OTHER INFORMATION: Xaa = Any Amino Acid

<400> SEQUENCE: 14

Xaa Pro Pro Pro Pro Pro
1               5

<210> SEQ ID NO 15
<211> LENGTH: 24
<212> TYPE: DNA
<213> ORGANISM: unknown
<220> FEATURE:
<223> OTHER INFORMATION: WIP-out PCR primer sequence, human

<400> SEQUENCE: 15
gcggcattcg gttcctctga ggct                                              24

<210> SEQ ID NO 16
<211> LENGTH: 25
<212> TYPE: DNA
<213> ORGANISM: unknown
<220> FEATURE:
<223> OTHER INFORMATION: WIP-in PCR primer sequence, human

<400> SEQUENCE: 16
acttctgtgg cctggagaag gcaca                                             25

<210> SEQ ID NO 17
<211> LENGTH: 4
<212> TYPE: PRT
<213> ORGANISM: unknown
<220> FEATURE:
<223> OTHER INFORMATION: KLRK motif in Ena/VASP

<400> SEQUENCE: 17

Lys Leu Arg Lys
1

<210> SEQ ID NO 18
<211> LENGTH: 4
<212> TYPE: PRT
<213> ORGANISM: unknown
<220> FEATURE:
<223> OTHER INFORMATION: KLRR motif in Ena/VASP

<400> SEQUENCE: 18

Lys Leu Arg Arg
1

<210> SEQ ID NO 19
<211> LENGTH: 6

```
<212> TYPE: PRT
<213> ORGANISM: unknown
<220> FEATURE:
<223> OTHER INFORMATION: APPPPP motif, WIP

<400> SEQUENCE: 19

Ala Pro Pro Pro Pro Pro
 1               5

<210> SEQ ID NO 20
<211> LENGTH: 6
<212> TYPE: PRT
<213> ORGANISM: unknown
<220> FEATURE:
<223> OTHER INFORMATION: PPP(psi)XP putative SH3 binding motif
<221> NAME/KEY: VARIANT
<222> LOCATION: (1)...(6)
<223> OTHER INFORMATION: Xaa = Any Amino Acid
<221> NAME/KEY: VARIANT
<222> LOCATION: 4, 5
<223> OTHER INFORMATION: Xaa = Any Amino Acid

<400> SEQUENCE: 20

Pro Pro Pro Xaa Xaa Pro
 1               5

<210> SEQ ID NO 21
<211> LENGTH: 6
<212> TYPE: PRT
<213> ORGANISM: unknown
<220> FEATURE:
<223> OTHER INFORMATION: profilin-binding consensus sequence
<221> NAME/KEY: VARIANT
<222> LOCATION: (1)...(1)
<223> OTHER INFORMATION: Xaa = A, G, L or S
<221> NAME/KEY: VARIANT
<222> LOCATION: 1
<223> OTHER INFORMATION: Xaa = Any Amino Acid

<400> SEQUENCE: 21

Xaa Pro Pro Pro Pro Pro
 1               5

<210> SEQ ID NO 22
<211> LENGTH: 19
<212> TYPE: PRT
<213> ORGANISM: Artificial Sequence
<220> FEATURE:
<223> OTHER INFORMATION: Translated WIP ORF No.1

<400> SEQUENCE: 22

Pro Gly Gln Val Arg Arg Gln Gly Asn Ser Arg Ser Trp Leu Phe
 1               5                  10                  15

Ser Ala Asp

<210> SEQ ID NO 23
<211> LENGTH: 12
<212> TYPE: PRT
<213> ORGANISM: Artificial Sequence
<220> FEATURE:
<223> OTHER INFORMATION: Translated WIP ORF No. 2

<400> SEQUENCE: 23

Asn Asn Thr Asp Leu Ser Ala Arg Leu Phe Asn Ala
 1               5                  10

<210> SEQ ID NO 24
<211> LENGTH: 507
```

```
<212> TYPE: PRT
<213> ORGANISM: Artificial Sequence
<220> FEATURE:
<223> OTHER INFORMATION: Translated WIP ORF No. 3

<400> SEQUENCE: 24
```

Leu Pro Lys Met Pro Val Pro Pro Pro Ala Pro Pro Pro Pro
1               5                   10                  15

Thr Phe Ala Leu Ala Asn Thr Glu Lys Pro Thr Leu Asn Lys Thr Glu
            20                  25                  30

Gln Ala Gly Arg Asn Ala Leu Leu Ser Asp Ile Ser Lys Gly Lys Lys
            35                  40                  45

Leu Lys Lys Thr Val Thr Asn Asp Arg Ser Ala Pro Ile Leu Asp Lys
50                  55                  60

Pro Lys Gly Ala Gly Ala Gly Gly Gly Gly Phe Gly Gly Gly
65                  70                  75                  80

Gly Gly Phe Gly Gly Gly Gly Gly Gly Gly Gly Ser Phe Gly
                85                  90                  95

Gly Gly Gly Pro Pro Gly Leu Gly Gly Leu Phe Gln Ala Gly Met Pro
                100                 105                 110

Lys Leu Arg Ser Thr Ala Asn Arg Asp Asn Asp Ser Gly Gly Ser Arg
            115                 120                 125

Pro Pro Leu Leu Pro Pro Gly Arg Ser Thr Ser Ala Lys Pro Phe
            130                 135                 140

Ser Pro Pro Ser Gly Pro Gly Arg Phe Pro Val Pro Ser Pro Gly His
145                 150                 155                 160

Arg Ser Gly Pro Pro Glu Pro Gln Arg Asn Arg Met Pro Pro Arg
                165                 170                 175

Pro Asp Val Gly Ser Lys Pro Asp Ser Ile Pro Pro Val Pro Ser
                180                 185                 190

Thr Pro Arg Pro Ile Gln Ser Ser Leu His Asn Arg Gly Ser Pro Pro
            195                 200                 205

Val Pro Gly Gly Pro Arg Gln Pro Ser Pro Gly Pro Thr Pro Pro Pro
210                 215                 220

Phe Pro Gly Asn Arg Gly Thr Ala Leu Gly Gly Gly Ser Ile Arg Gln
225                 230                 235                 240

Ser Pro Leu Ser Ser Ser Ser Pro Phe Ser Asn Arg Pro Pro Leu Pro
                245                 250                 255

Pro Thr Pro Ser Arg Ala Leu Asp Asp Lys Pro Pro Pro Pro Pro
                260                 265                 270

Pro Val Gly Asn Arg Pro Ser Ile His Arg Glu Ala Val Pro Pro
                275                 280                 285

Pro Pro Gln Asn Asn Lys Pro Pro Val Pro Ser Thr Pro Arg Pro Ser
            290                 295                 300

Ala Pro His Arg Pro His Leu Arg Pro Pro Pro Ser Arg Pro Gly
305                 310                 315                 320

Pro Pro Pro Leu Pro Pro Ser Ser Gly Asn Asp Glu Thr Pro Arg
                325                 330                 335

Leu Pro Gln Arg Asn Leu Ser Leu Ser Ser Thr Pro Pro Leu Pro
                340                 345                 350

Ser Pro Gly Arg Ser Gly Pro Leu Pro Pro Val Pro Ser Glu Arg
                355                 360                 365

Pro Pro Pro Pro Val Arg Asp Pro Pro Gly Arg Ser Gly Pro Leu Pro
370                 375                 380

-continued

```
Pro Pro Pro Pro Val Ser Arg Asn Gly Ser Thr Ser Arg Ala Leu Pro
385                 390                 395                 400

Ala Thr Pro Gln Leu Pro Ser Arg Ser Gly Val Asp Ser Pro Arg Ser
            405                 410                 415

Gly Pro Arg Pro Pro Leu Pro Pro Asp Arg Pro Ser Ala Gly Ala Pro
        420                 425                 430

Pro Pro Pro Pro Pro Ser Thr Ser Ile Arg Asn Gly Phe Gln Asp Ser
        435                 440                 445

Pro Cys Glu Asp Glu Trp Glu Ser Arg Phe Tyr Phe His Pro Ile Ser
    450                 455                 460

Asp Leu Pro Pro Pro Glu Pro Tyr Val Gln Thr Thr Lys Ser Tyr Pro
465                 470                 475                 480

Ser Lys Leu Ala Arg Asn Glu Ser Arg Ser Gly Ser Asn Arg Arg Glu
            485                 490                 495

Arg Gly Gly Pro Pro Leu Pro Pro Ile Pro Arg
            500                 505

<210> SEQ ID NO 25
<211> LENGTH: 17
<212> TYPE: PRT
<213> ORGANISM: Artificial Sequence
<220> FEATURE:
<223> OTHER INFORMATION: Translated WIP ORF No.4

<400> SEQUENCE: 25

Ser Leu Ala Ala Leu Leu Tyr Pro Ser Ser Arg Ala Ala Ser Val Gly
1               5                   10                  15

Ile

<210> SEQ ID NO 26
<211> LENGTH: 7
<212> TYPE: PRT
<213> ORGANISM: Artificial Sequence
<220> FEATURE:
<223> OTHER INFORMATION: Translated WIP ORF No.5

<400> SEQUENCE: 26

Glu Leu Asp Thr Leu Pro Pro
1               5

<210> SEQ ID NO 27
<211> LENGTH: 14
<212> TYPE: PRT
<213> ORGANISM: Artificial Sequence
<220> FEATURE:
<223> OTHER INFORMATION: Synthetic WIP peptide

<400> SEQUENCE: 27

Glu Ser Arg Ser Gly Ser Asn Arg Arg Glu Arg Gly Ala Pro
1               5                   10
```

WIP, A WASP-ASSOCIATED PROTEIN

RELATED APPLICATIONS

This application is a continuation-in-part of U.S. application Ser. No. 09/599,287, filed Jun. 22, 2000, which is a continuation of International Application No. PCT/US98/27501, which designated the United States and was filed on Dec. 22, 1998, published in English, which claims the benefit of U.S. Provisional Application No. 60/101,457, filed on Sep. 23, 1998 and U.S. Provisional Application No. 60/068,533, filed on Dec. 23, 1997.

The entire teachings of the above applications are incorporated herein by reference.

GOVERNMENT SUPPORT

The invention was supported, in whole or in part, by grant 59561 from United States Public Health Service, and by National Institutes of Health grants AI 37130 and AI 35714. The Government has certain rights in the invention.

BACKGROUND OF THE INVENTION

Wiskott-Aldrich Syndrome (WAS) is an X-linked immunodeficiency caused by mutations that affect the WAS protein (WASP). It is characterized by thrombocytopenia, eczema, impaired immunity and a predisposition to develop lymphomas and leukemias (Cooper, M. D., Chase, H. P., Lowman, J. T., Krivit, W. & Good, R. A. (1968) *Am. J. Medicine,* 44: 499–513). The size of platelets and lymphocytes is reduced in WAS and scanning electron microscopy of T lymphocytes shows a relatively smooth surface with decrease in the number and size of microvilli, suggesting a defect in cytoskeletal architecture (Remold-O'Donnell, E. & Rosen, F. S. (1993) in *Sialophorin (CD43) and the Wiskott-Aldrich Syndrome,* eds. Rosen, F. S. & Seligmann, M. S. (Harwood Academic Publishers, Chur), pp. 225–241), pp.225–241 (1993)). The WAS gene is located on Xp11.22-Xp11.23 and encodes a 502 amino acid (aa) long proline rich protein, WASP (Derry, J. M. J., Ochs, H. D. & Francke, U. (1994) *Cell,* 78: 635–644.). WASP contains an N-terminal pleckstrin homology (PH) domain, which partially overlaps with a WASP homology (WH) domain, WH1, found in several proteins involved in the maintenance of cytoskeletal integrity that include Ena, Mena, Evl and VASP (Gertler, F. B., Niebuhr, K., Reinhard, M., Wehland, J. & Soriano, P. (1996) *Cell,* 87: 227–239). The WH1 domain in WASP is followed by a GTPase binding domain (GBD/CRIB) (Bunnell, S. C., Henry, P. A., Kolluri, R., Kirchhausen, T., Rickles, R. J. & Berg, L. J. (1996) *J. Biol. Chem.* 271: 25646–25656), a number of proline rich stretches, a second WH domain (WH2), a short verprolin homology sequence, a cofilin homology sequence, and an acidic C-terminal region. Recently, a protein highly homologous to WASP was cloned from bovine brain and was termed N-WASP (Miki, H., Miura, K. & Takenawa, T. (1996) *EMBO J.* 15, 5326–5335). N-WASP has a domain organization similar to that of WASP, and is widely expressed, in contrast to WASP which is expressed only in hematopoietic cells.

WASP binds via its GBD domain to the small molecular weight GTPase Cdc42 and weakly to Rac, but not to Rho (Aspenstrom, P., Lindberg, U. & Hall, A. (1996) *Curr. Biol.* 6: 70–75; Kolluri, R., Tolias, K. F., Carpenter, C. L., Rosen, F. S. & Kirchhausen, T. (1996) *Proc. Natl. Acad. Sci. (USA)* 93: 5615–5618; Symons, M., Derry, J. M. J., Kariak, B., Jiang, S., Lemahieu, V., McCormick, F., Francke, U. & Abo, A. (1996) *Cell* 84: 723–734). Cdc42, Rac and Rho regulate cytoskeletal organization (Nobes, C. D. & Hall, A. (1995) *Cell* 81: 53–62). Overexpression of WASP induces the formation of actin-containing clusters (Symons, M., Derry, J. M. J., Kariak, B., Jiang, S., Lemahieu, V., McCormick, F., Francke, U. & Abo, A. (1996) *Cell* 84: 723–734). This is inhibited by dominant negative mutants of Cdc42, but not of Rac or Rho (Symons, M., Derry, J. M. J., Kariak, B., Jiang, S., Lemahieu, V., McCormick, F., Francke, U. & Abo, A. (1996) *Cell* 84: 723–734). These findings suggest that WASP may provide a link between Cdc42, Rac and the cytoskeleton.

WASP interacts with components of signal transduction pathways via their SH3 domains (Src homology 3) which recognize the proline rich domain in WASP (Featherstone, C. (1997) *Science* 275: 27–28). WASP associates with the adaptor protein Nck (Rivero-Lezcano, O. M., Marcilla, A., Sameshima, J. H. & Robbins, K. C. (1995) *Mol. Cell Biol.,* 15: 5725–5731). Nck can be recruited via its SH2 domain to tyrosine phosphorylated receptors (Galisteo, M. L., Chernoff, J., Su, Y.-C., Skolnich, E. Y. & Schlessinger, J. (1996) *J. Biol. Chem.* 271: 20997–21000). WASP also binds in vivo to fyn (Rivero-Lezcano, O. M., Marcilla, A., Sameshima, J. H. & Robbins, K. C. (1995) *Mol. Cell Biol.* 15: 5725–5731; Banin, S., Truong, O., Katz. D. R., Waterfield, M. D., Brickell, P. M. & Gout, I. (1996) *Curr. Biol.,* 6: 981–988) and in vitro to the src kinase fgr, to the tyrosine kinases btk, itk, Abl and to the p85 subunit of PLC-g (Banin, S., Truong, O., Katz. D. R., Waterfield, M. D., Brickell, P. M. & Gout, I. (1996) *Curr. Biol.* 6, 981–988; Molina, I. J., Sancho, J., Terhorst, C., Rosen, F. S. & Remold-O'Donnell, E. (1993) *J. Immunol.,* 151: 4383–4390; Finan, P. M., Soames, C. J., Wilson, L., Nelson, D. L., Stewart, D. M., Truong, O., Hsuan, J. J. & Kellie, S. (1996) *J. Biol. Chem.,* 271: 26291–26295).

The WASP-interacting protein (WIP) is a proline-rich protein. However, the role of WIP in TCR-mediated cell activation and cytoskeleton organization are not understood.

There exists a need therefore, for further studies, particularly in vivo studies, to elucidate the biological functions of WIP, to identify regulators of WIP, and to develop therapeutic strategies for the treatment or prevention of diseases or conditions that are associated with WIP function.

SUMMARY OF THE INVENTION

Described herein is a novel human gene whose 503 amino acid (aa) product interacts with WASP. The protein is referred to as WIP, for WASP-interacting protein. The proline-rich WIP, which co-immunoprecipitated with WASP from lymphocytes, has been shown to bind to WASP at a site distinct from the Cdc42 binding site and to have actin, profilin and Nck binding motifs. Expression of WIP in human B cells, but not of a WIP truncation mutant that lacks the actin binding motif, increased polymerized actin content and induced the appearance of actin-containing cerebriform projections on the cell surface. Work described herein supports the role of WIP in cortical actin assembly that may be important for lymphocyte function. Overexpression of WIP increases F-actin content and induces actin containing structures in the human B cell line BJAB, suggesting an important role for WIP in the organization of the actin cytoskeleton.

In particular, the present invention relates to isolated (for example, purified, essentially pure) nucleic acids (oligonucleotides, polynucleotides, nucleotide sequences) which encode mammalian (for example, human) WIP, and include for example, nucleic acids (DNA, RNA) which are obtained from natural sources, recombinantly produced or chemically synthesized. The nucleic acids of the present invention include nucleic acids encoding human WIP (SEQ ID NO: 1) and characteristic portions of the nucleic acid sequences (for example, probes, primers). The invention also includes complementary sequences (i.e., a complement) of SEQ ID NO: 1 and characteristic portions thereof. The nucleic acids of the present invention encompass nucleic acids encoding a human WIP amino acid sequence (SEQ ID NO: 2) and characteristic portions thereof.

The present invention further relates to isolated, recombinantly produced or synthetic nucleic acids which hybridize to the nucleic acids described herein (for example, the complement of SEQ ID NO: 1 or characteristic portions thereof) and encode WIP (a protein having the same amino acid sequence as the amino acid sequences included herein and/or a protein which exhibits the same characteristics as WIP described herein). In particular, the invention relates to nucleic acids which hybridize, under moderate or high stringency conditions, to SEQ ID NO: 1 characteristic portions thereof or other sequences which encode WIP.

Also encompassed by the present invention is a nucleic acid construct comprising nucleic acid which encodes a WIP (for example, SEQ ID NO: 1 and characteristic portions thereof), wherein the nucleic acid of the construct is expressed when the construct is present in an appropriate host cell. In one embodiment, the nucleic acid construct of the present invention is operably linked to exogenous regulatory sequence(s) such as a promoter and/or enhancer, whereby mammalian WIP is expressed when the host cell is maintained under conditions suitable for expression. The present invention also relates to a host cell comprising nucleic acid encoding mammalian WIP.

Also encompassed by the present invention is a method for producing a WIP (mammalian, such as human). In one embodiment, a nucleic acid construct comprising a nucleotide sequence (DNA, RNA) which encodes a WIP is introduced into a host cell, resulting in production of a recombinant host cell which contains a WIP coding sequence operably linked to an (i.e., at least one) expression control sequence. The host cells produced are maintained in a suitable medium under conditions appropriate for the nucleotide sequence to be expressed, whereby the encoded WIP is produced.

The present invention also relates to isolated (for example, purified, essentially pure) WIP and includes, for example, WIP obtained from natural sources, recombinantly produced or chemically synthesized. For example, the WIP can be human WIP (SEQ ID NO: 2) or functional portions thereof.

Also encompassed by the present invention is an agent which interacts with WIP directly or indirectly, and inhibits or enhances WIP function. In one embodiment, the agent is an inhibitor which interferes with WIP directly (for example, by binding WIP) or indirectly (for example, by blocking the ability of WIP to a) bind WASP, profilin and/or Nck; b) increase F-actin content in lymphocytes; c) increase cellular content of polymerized actin; d) increase appearance of cerebriform projections on the cell surface containing F-actin). In a particular embodiment, an inhibitor of the WIP is an antibody specific for WIP protein or a portion of a WIP; that is, the antibody binds the WIP. For example, the antibody can be specific for the human WIP (SEQ ID NO: 2) or functional portions thereof. Alternatively, the inhibitor can be an agent other than an antibody (for example, small organic molecule, protein, peptide) which binds WIP and blocks its activity. Furthermore, the inhibitor can be an agent which mimics WIP structurally but lacks its function. Alternatively, the inhibitor of WIP can be an agent which binds to or interacts with a molecule which WIP normally binds with or interacts with, thus blocking WIP from doing so and preventing it from exerting the effects it would normally exert. In another embodiment, the agent is an enhancer of WIP which increases the activity of WIP (for example, the ability of WIP to a) bind WASP, profilin and/or Nck; b) increase F-actin content in lymphocytes; c) increase cellular content of polymerized actin; d) increase appearance of cerebriform projections on the cell surface containing F-actin), increases the length of time it is effective (by preventing its degradation or otherwise prolonging the time during which it is active) or both, either directly or indirectly.

The present invention also relates to antibodies (monoclonal or polyclonal) or functional portions thereof (for example, an antigen binding portion such as an Fv, Fab, Fab', or F(ab')$_2$ fragment) which bind WIP.

WIP DNA fragments can be used as probes (for example, in hybridization methods) or primers (for example, in amplification methods). They can be used, for example, to determine whether WIP DNA or RNA is present in cells (for example, a sample obtained from an individual). For example, WIP DNA can be used as a probe to determine if wild-type (nonmutated) or mutated WIP DNA is present in a sample of cells and also to determine the extent (quantity) to which wild-type and mutated forms occur. Antibodies can also be used as probes to assess cells for the occurrence of WIP.

Isolation of WIP makes it possible to detect WIP in a sample (for example, test sample). The present invention also relates to a method of detecting WIP in a sample (for example, blood) obtained from an individual, such as a human. In one embodiment, the sample is treated to render nucleic acids in the sample available for hybridization to a nucleic acid probe (for example, SEQ ID NO: 1 and/or characteristic portions thereof which bind to characteristic regions of WIP-encoding nucleic acids). The treated sample is combined with a nucleic acid probe (labeled or unlabeled) comprising or complementary to all or a characteristic portion of the nucleotide sequence encoding WIP, under conditions appropriate for hybridization of complementary nucleic acids to occur. Hybridization of nucleic acids in the treated sample with the nucleic acid probe is detected; the occurrence of hybridization indicates the presence of WIP in the sample. In another embodiment, the sample is contacted with an antibody which binds to WIP (for example, SEQ ID NO: 2 or functional portions thereof) under conditions suitable for binding of the antibody to the mammalian WIP. Binding of the antibody to a component of the sample is detected; binding of the antibody to a component of the sample indicates the presence of WIP protein in the sample.

Isolation of WIP also makes it possible to identify a promoter(s) and/or enhancer(s) of the WIP gene. Identification of promoters and/or enhancers of the WIP gene allow for identification of regulators of WIP transcription.

In addition, the present invention relates to transgenic non-human animals (for example, mice) which lack the WIP gene or contain a nonfunctional WIP gene such that WIP activity is lacking (for example, WIP knockout mouse). The invention also relates to methods of producing WIP gene knockout animals, such as mice. WIP knockout mice can be used to further study the WIP gene and to assay for inhibitors and enhancers of WIP.

Methods of altering actin content, actin polymerization or both, methods of altering or regulating WASP function and methods of treating conditions in which WIP and/or WASP and/or their respective DNAs are deficient and/or defective are also the subject of this invention. In the methods, WIP or DNA encoding WIP can be administered to an individual, by known methods, in sufficient quantity to alter actin content and/or the extent to which polymerization occurs and, thus, to prevent or reduce (totally or partially) cytoskeletal abnormalities and other adverse effects. For example, Wiskott-Aldrich Syndrome can be treated or prevented in this manner.

The present invention also relates to a transgenic non-human mammal that has a disrupted WIP gene (also referred to herein as a WIP knockout mammal or a transgenic non-human WIP knockout mammal), the mammal being, for example, a mouse, a goat or a rabbit, and the like.

In a preferred embodiment, the transgenic non-human mammal is a mouse.

In one embodiment, the transgenic non-human mammal lacks a functional WIP gene. The transgenic non-human mammal of the present invention can have at least one non-functional allele for the WIP gene.

In another embodiment, the transgenic non-human mammal is characterized by a disruption of the WIP gene which is either a homozygous disruption or a heterozygous disruption.

In a particular embodiment, the disruption of the WIP gene in the genome of the WIP knockout mammal is in a segment that includes exons 2 to 5 of the WIP gene.

In another embodiment, the genome of the WIP knockout mammal includes an insertion of an exogenous nucleic acid sequence into an exon of the WIP gene, or a substitution of an exogenous nucleic acid sequence into an exon of the WIP gene.

As a result of the disruption of the WIP gene, the transgenic non-human mammal of the present invention manifests particular phenotypes. In one embodiment, the WIP knockout mammal has disrupted a cortical actin network, for example, in lymphocytes, including T cells and B cells. In another embodiment, the WIP knockout mammal is defective in contact formation and immunological synapse formation in response to T cell activation, for example, failure to form an expanded interface with an antigen presenting cell (APC). In a further embodiment, T cells of the WIP knockout mammal fail to proliferate, secrete IL-2, increase F-actin content, polarize and extend protrusions following T cell receptor (TCR) ligation. In another embodiment, B cells of the WIP knockout mammal are enhanced in their proliferation, CD69 expression and tyrosine phosphorylation of proteins less than 50kDa, in response to B cell receptor (BCR) ligation. In a further embodiment, B cells of the WIP knockout mammal fail to undergo IgG isotype switching in response to T-dependent (TD) antigen stimulation.

The invention further provides a method of producing a transgenic non-human mammal which lacks a functional WIP gene. This method includes introducing a targeting vector into an embryonic stem (ES) cell to produce a transgenic stem cell in which the WIP gene is disrupted. This transgenic ES cell, which includes a disrupted WIP gene due to the integration of the targeting vector into its genome, is selected. The selected ES cell is then introduced into a blastocyst, to form a chimeric blastocyst. The chimeric blastocyst is introduced into the uterus of a pseudo-pregnant mammal and the pseudo-pregnant mammal gives birth to a transgenic non-human mammal that lacks a functional WIP gene due to heterozygous disruption of the WIP gene. The method can further comprise breeding the transgenic non-human mammal which lacks a functional WIP gene due to a heterozygous disruption with a second mammal of the same species to generate F1 progeny having a heterozygous disruption of the WIP gene, thereby expanding the population of transgenic non-human mammals having a heterozygous disruption of the WIP gene. The F1 progeny can then be cross-bred to produce a transgenic non-human mammal which lacks a functional WIP gene due to a homozygous disruption of the WIP gene.

The present invention also relates to constructs or vectors (for example, a WIP targeting construct) designed to disrupt a wild-type mammalian WIP gene. In one embodiment, the invention provides a construct which comprises, in a 5' to 3' direction, about 4.5 kb of a WIP genomic DNA sequence which is upstream of exon 2 of the WIP DNA sequence and which includes an ATG start codon of the WIP DNA sequence, and about 3.5 kb of a WIP genomic DNA sequence which is downstream of exon 5 of the WIP DNA sequence and which includes a TGA stop codon of the WIP DNA sequence. In a particular embodiment, the construct also comprises a reporter gene between the genomic DNA sequence which is upstream of exon 2 and the genomic DNA sequence which is downstream of exon 5 of WIP. More specifically, the invention provides a WIP gene replacement vector in which the genomic nucleotide sequence of the WIP gene from exon 2 to exon 5 is removed and/or replaced with a neomycin resistance gene (Neo).

The present invention also provides isolated cells, cell lines, tissues, cellular extracts, organelles and organs, which lack a functional WIP gene. In one embodiment, the cells are T cells. In another embodiment, the cells are B cells.

Also included in the invention is a method for determining whether an agent inhibits WIP activity. In one embodiment, an amount of a TD antigen and the agent to be tested are administered to a non-human mammal that has wild-type expression of WIP and to a corresponding non-human mammal whose genome comprises a disruption of a WIP gene. The phenotype of cells from the treated non-human mammal that has wild-type expression of WIP with cells from a similarly treated WIP knockout non-human mammal of the invention are determined and compared. If the phenotype of the cells from non-human mammal that has wild-type expression of WIP is about the same as the phenotype of the cells from the WIP knockout non-human mammal, then the agent inhibits WIP. In a preferred embodiment, the cells are T cells. In an alternative embodiment, the cells are B cells. In another preferred embodiment, the cells are derived from hematopoietic stem cells, including, and without limitation, monocytes, macrophages and mast cells. Inhibitors of WIP that are identified by this method are included in this invention.

The present invention also relates to a method for determining whether an agent inhibits WIP activity by contacting a cell whose genome has a wild-type WIP gene, with an amount of a TD antigen, and the agent to be tested, and determining and comparing the phenotype of the treated cell that has wild-type expression of WIP with a similarly treated cell isolated from a WIP knockout non-human mammal of the invention, such that if the phenotype of the cell that has wild-type expression of WIP is about the same as the phenotype of the cell isolated from the WIP knockout non-human mammal, then the agent inhibits WIP. In a preferred embodiment, the cells are T cells. In an alternative embodiment, the cells are B cells. In another preferred embodiment, the cells are derived from hematopoietic stem cells, including, and without limitation, monocytes, macrophages and mast cells. Inhibitors of WIP that are identified by this method are included in this invention.

The invention also provides a method for identifying an agent that exhibits, (for example, mimics), WIP activity. In one embodiment, an amount of a TD antigen and the agent to be tested are administered to a non-human mammal that has wild-type expression of WIP and to a corresponding non-human mammal whose genome comprises a disruption of a WIP gene. The phenotype of cells from the treated non-human mammal that has wild-type expression of WIP with cells from a similarly treated WIP knockout non-human mammal of the invention are determined and compared. If the phenotype of the cells from WIP knockout non-human mammal, is about the same as the phenotype of the cells from the non-human mammal that has wild-type expression of WIP, then the agent exhibits WIP activity or is a mimic of WIP. In a preferred embodiment, the cells are T cells. In an alternative embodiment, the cells are B cells. In another preferred embodiment, the cells are derived from hematopoietic stem cells, including, and without limitation, monocytes, macrophages and mast cells. Mimics of WIP activity identified by this method are also included in the invention.

A further method for identifying an agent that exhibits WIP activity by contacting a cell whose genome has a wild-type WIP gene, with an amount of a TD antigen, and the agent to be tested, and determining and comparing the phenotype of the treated cell that has wild-type expression of WIP with a similarly treated cell isolated from a WIP knockout non-human mammal of the invention, such that if the phenotype of the cell isolated from the WIP knockout non-human mammal is about the same as the phenotype of the cell that has wild-type expression of WIP, then the agent exhibits WIP activity or is a mimic of WIP. In a preferred embodiment, the cells are T cells. In an alternative embodiment, the cells are B cells. In another preferred embodiment, the cells are derived from hematopoietic stem cells, including, and without limitation, monocytes, macrophages and mast cells. Mimics of WIP activity identified by this method are also included in the invention.

Also provided in the invention is a method for inhibiting an increase in F-actin content in a T cell in response to T cell receptor ligation by contacting the T cell with an effective amount of a WIP inhibitor in the presence of a T-dependent antigen.

In addition, a method for inhibiting an increase in F-actin content in a mammal in response to T cell receptor ligation by administering to the mammal an effective amount of a WIP inhibitor in the presence of a T-dependent antigen is provided.

A method for stimulating an increase in F-actin content in a T cell in response to T cell receptor ligation by contacting the T cell with an effective amount of a WIP agonist in the presence of a T cell receptor stimulant is also included in the invention.

Furthermore, a method for stimulating an increase in F-actin content in a mammal in response to T cell receptor ligation by administering to the mammal an effective amount of a WIP agonist in the presence of a T-dependent antigen is provided.

The present invention also relates to a method of enhancing T cell receptor-mediated T cell activation in a mammal, by administering to the mammal a therapeutically-effective amount of an agent that enhances WIP activity.

Additionally, a method of inhibiting T cell receptor-mediated T cell activation in a mammal, by administering to the mammal a therapeutically-effective amount of an agent that inhibits WIP activity, is also provided.

Also, a method of enhancing B cell proliferation in a mammal, by administering to the mammal a therapeutically-effective amount of an agent that inhibits WIP activity.

Furthermore, a method of inhibiting or suppressing B cell proliferation in a mammal, by administering to the mammal a therapeutically-effective amount of an agent that enhances WIP activity, is also provided.

BRIEF DESCRIPTION OF THE DRAWINGS

FIGS. 1A–1B are the nucleotide sequence of WIP cDNA (SEQ ID NO: 1).

FIG. 1C is a schematic representation of full length WIP, WIP2, WIP4 and Prp12 cDNAs. The open box in Prp12 represents the 7 aa that replace the C-terminal 17 aa in WIP.

FIG. 1D is the deduced amino acid (aa) sequence of WIP (SEQ ID NO.: 2). The two APPPPP (SEQ ID NO: 3) motifs implicated in profilin binding are denoted by asterisks. A line is drawn over the KLKK (SEQ ID NO: 4) motif implicated in acting binding.

FIG. 1E is the sequence alignment of the N terminal regions of WIP (SEQ ID NO.: 5) and verprolin (SEQ ID NO.: 6). The two verprolin homology regions are boxed.

FIG. 1F is the sequence alignment of GRSGPXPPXP (SEQ ID NO: 7) motifs in WIP 352–361 (SEQ ID NO: 8), WIP 374–383 (SEQ ID NO: 9), WIP 410–419 (SEQ ID NO: 10), WASP 338–347 (SEQ ID NO: 11) and WASP 376–385 (SEQ ID NO: 12). Numbers refer to aa positions.

FIG. 3A is a diagram of the genomic structure of the wip gene and predicted structure of the targeted allele after homologous recombination. Exons are represented by black boxes. Neo: neomycin resistance gene. The 650 bp SacI/EcoRI hybridization probe is shown as a patterned box. B: BamHI, E: EcoRI, S: SacI, and X: XbaI (not all restriction sites are shown).

FIG. 3B is a Southern blot analysis of tail DNA. Genomic DNA was digested by EcoRI and probed with the 650 bp fragment immediately 3' to the targeted locus, shown in A. The WT allele is represented by the 4 kb band. The knockout allele is represented by the 5.8 kb band.

FIG. 3C is a Western blot analysis of WIP from thymocytes using rabbit antibody against a ESRSGSNR-RERGAP WIP peptide (SEQ ID NO: 27).

FIG. 4A is a graph demonstrating the results of a proliferation assay: Purified spleen B cells from 6–9-week-old mice were cultured in medium alone or in the presence of stimuli and proliferation was measured by [$^3$H]-thymidine incorporation. Error bars represent SDs of triplicate values. Similar results were obtained in 4 experiments.

FIG. 4B is the result of a FACS analysis detecting activation markers: Splenic B cells from 6–9-week-old mice were incubated for 20 hrs with the indicated stimuli, then analyzed by FACS for expression of CD69 and B220. Similar results were obtained in two other experiments.

FIG. 4C is a western blot analysis of protein tyrosine phosphorylation: Splenic B cells from 6–9-week-old mice were incubated a 37° C. for the indicated times (minutes) with anti-IgM, lysed, run on SDS-PAGE, transferred to nitrocellulose and developed with anti-phosphotyrosine antibody. The membrane was stripped and re-probed with anti-PLCγ2 as a loading control. Identical results were obtained in two other experiments.

FIG. 5A is a scatter plot of serum immunoglobulin levels from nonimmunized 6–8-week-old WIP$^{-/-}$ (open circles) mice and WT littermates (filled circles) as determined by isotype-specific ELISA.

FIG. 5B are graphs depicting IgM and IgG antigen-specific antibody responses of 12–15-week-old mice to KLH following immunization with the TD antigen TNP-KLH as determined by ELISA.

FIG. 5C are graphs depicting IgG antigen-specific antibody responses of 12–15-week-old mice to TNP following immunization with the TI type I (TNP-LPS) or TI type II (TNP-Ficoll) antigens as determined by ELISA.

FIG. 6A is a bar graph depicting the results of thymidine incorporation in purified L.N. T cells from 6–10-week-old WT mice and littermates WIP$^{-/-}$ stimulated in wells coated with increasing concentrations of anti-CD3ε or in the presence of PMA and ionomycin. T cells were cultured for 48 hr, pulsed with 1 μCi [$^3$H]-thymidine for an additional 16 hr, then collected and scintillation counted. Error bars represent SDs of triplicate values. Displayed are the results of one experiment representative of the four performed with similar results.

FIG. 6B is a bar graph depicting thymidine incorporation in purified L.N. T cells from from 6–10-week-old WT mice and littermates WIP$^{-/-}$ stimulated in wells coated with 10 μg/ml anti-CD3 in the presence of plate-bound anti-CD28 (10 μg/ml) or soluble IL-2 (40 ng/ml). Experimental conditions are as described in FIG. 6A. Error bars represent SDs of triplicate values. Displayed are the results of one experiment representative of the three performed with similar results.

FIG. 6C is the result of a FACS analysis of CD25 surface expression on purified CD4$^+$/CD8$^+$T cells from 6–10-week-old mice, before and after stimulation in wells coated with 10 μg/ml anti-CD3 with or without addition of plate-bound anti-CD28 (10 μg/ml) or IL-2 (40 ng/ml) for 20 hrs.

FIG. 6D is a bar graph of thymidine incorporation results of purified L.N. T cells from 6–10-week-old WT mice and littermates WIP$^{-/-}$ were stimulated in wells coated with 10 μg/ml anti-CD3 with or without addition of anti-CD28 (10 μg/ml) for 96 hrs. Supernatants were then collected and assayed for IL-2 by examining their capacity to induce the proliferation of the IL-2 dependent cell line CTLL2.

FIG. 6E is a panel of western blots of purified L.N. T cells from 12–14-week-old mice were stimulated on anti-CD3+ anti-CD28 coated plates for the indicated times. Cell lysates were blotted with anti-phosphoERK and anti-ERK as loading control and with anti-phosphoJNK and anti-JNK as loading control.

FIG. 7A is a graph depicting FACS analysis of purified L.N. T cells from 9–14-week-old WT or WIP$^{-/-}$ mice stimulated with anti-CD3 followed by cross-linking with a secondary anti-rat antibody. After 20 min. the cells were fixed, permeabilized, stained with phalloidin-TRITC and analyzed by FACS. Similar data were obtained in three other experiments.

FIG. 7B is a panel of photographs of purified T lymphocytes stimulated on anti-CD3 coated glass coverslips. After 20 min. the cells were fixed, stained with phalloidin-TRITC and examined by fluorescent microscopy.

FIG. 7C is a series of frames from a videotape of purified T cells from WT and WIP$^{-/-}$ mice added to anti-CD3 coated glass coverslips and allowed to sediment for 30 min at 4° C. After washing off unattached cells, warm (37° C.) medium was added and the cells were videotaped for 20 min. The indicated time frames were processed using Adobe Photoshop software. Arrowheads point to protrusions. Bar is 10 μm.

FIG. 8A, left panels: WIP$^{+/-}$ T cells.

FIG. 8A, right panels: WIP$^{-/-}$ T cells.

FIG. 8A, upper panels: organization of F-actin in a representative membrane fragment derived from an adhered but not spread cell at time zero. Actin filaments are present on the adherent membrane, but in a less dense network than after 15 min of stimulation (see FIG. 8A, bottom panels).

FIG. 8A, bottom left panel: organization of actin filaments within a protrusion made by a representative WIP$^{+/-}$ T cell after 15 min of incubation at 37° C. WIP$^{+/-}$ lymphocytes extend large blunt protrusions having convoluted surfaces.

FIG. 8A, inset, bottom, left panel: Representative morphology of an intact WIP$^{+/-}$ lymphocyte allowed to spread for 15 min. Protrusions from WIP$^{+/-}$ cells are larger than those made by WIP$^{-/-}$ cells (compare to FIG. 8A, inset, right panel) and are filled with a dense matrix of F-actin.

FIG. 8A, upper right panel: Adherent WIP$^{-/-}$ T cell at time zero. A sparse coat of actin filaments decorate the membrane.

FIG. 8A, bottom right panel: After 15 min of stimulation, the actin filament density in the membrane of the protrusions remain sparse and similar to that found in the adherent cell at time zero.

FIG. 8A, bottom right panel, inset: Activated WIP$^{-/-}$ lymphocytes only extend small protrusions. Bar is 200 nm.

FIG. 8B, left panels, WIP$^{+/-}$ B cells: unstimulated (FIG. 8B upper left panel) and stimulated (FIG. 8B bottom left panel) B cells show a similar density of actin filaments associated with the membrane.

FIG. 8B right panels, WIP$^{-/-}$ B cells: before (FIG. 8B upper right panel) and after stimulation (FIG. 8B bottom right panel), WIP-deficient B cells show sparse actin filaments associated with the membrane. Bar is 200 nm.

DETAILED DESCRIPTION OF THE INVENTION

Figure 2A:
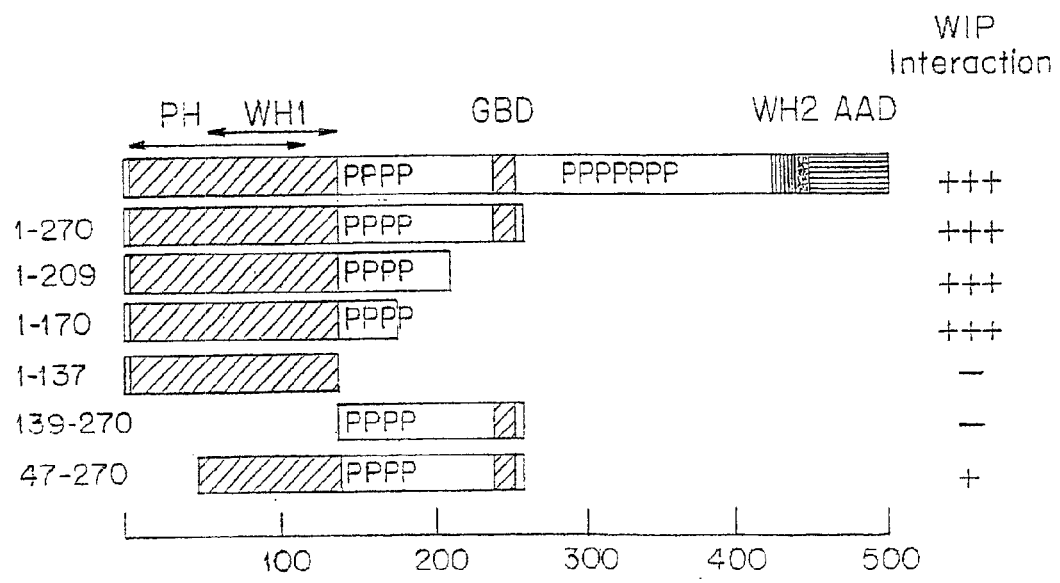
FIG. 2A is a mapping of the WIP binding site of WASP. The domains of WASP are indicated. PH: Pleckstrin homology domain (aa 6–105); WH1: WH1 domain (aa 47–137); pppppp (SEQ ID NO: 13): proline rich region; GBD: GTPase binding domain (aa 238–257); WH2: WH2 domain (aa 423–449); AAD: actin association domain (aa 443–502). The numbers under the bar at the bottom of the diagram represent the aa of WASP. Truncation mutants of WASP, generated either by PCR or by cleavage with appropriate restriction enzymes, were cloned into the pGBT9 vector and examined for WIP binding in the yeast two hybrid system. Blue color development by β-galactosidase activity was used to score the interaction of WIP with WASP truncations. +++ represents color change in 30 min. or less, + represents color change in 3 h and – indicates no color change and lack of growth in His⁻ medium. For each mutant at least three independent colonies were tested in the β-galactosidase assay.

Described herein is a novel gene and its product, WIP, which associates with WASP. The subject invention relates to the isolated WIP gene or cDNA (see FIGS. 1A–1B); nucleic acid probes, which can be fragments of the WIP gene or WIP cDNA or full-length; nucleic acid primers, which are fragments of WIP cDNA or the WIP gene; methods of assessing cells (for example, for diagnostic purposes) for the presence of WIP DNA, (for example, wildtype or mutated) or for the absence or occurrence of a reduced level of WIP DNA; WIP mRNA; WIP or WIP fragments, such as those which are useful to generate antibodies which bind WIP; and antibodies which bind WIP. Also the subject of this invention are methods of treating conditions in which WIP and/or WASP DNA or protein is deficient (in quantity) and/or defective (for example, mutated/altered) such that an individual is adversely affected (for example, has Wiskott-Aldrich Syndrome); methods of altering or regulating WASP and its functions; and methods of altering actin content, actin polymerization or both in cells, such as human lymphoid cells (for example, β lymphocytes). A further subject of this invention is an assay to identify drugs which alter (for example, enhance) the activity of WIP or expression of WIP DNA.

Isolated WIP DNA comprises DNA whose sequence is represented herein (for example, SEQ ID NO.: 1), DNA which is the complement of WIP DNA of SEQ ID NO.: 1; DNA which encodes a WIP (for example, DNA which encodes WIP as represented in SEQ ID NO.: 2) and DNA which hybridizes to WIP DNA or to a WIP DNA complement. WIP RNA is also the subject of this invention. Isolated WIP is another subject of this invention and includes the amino acid sequence SEQ ID NO.: 2, shown in FIG. 1D, and other amino acid sequences which are sufficiently similar to that of SEQ ID NO.: 2 that they have substantially the same characteristics and functions as described herein for WIP. DNA, RNA and protein are referred to herein as "isolated", which is intended to include DNA, RNA and protein obtained from (isolated from) sources in which they occur in nature, as well as DNA, RNA and protein produced by recombinant or chemical synthetic methods. The WIP DNA, RNA and protein can be of vertebrate, including mammalian, such as human, origin.

The present invention relates to isolated (for example, purified, essentially pure) WIP gene which is involved in actin polymerization and redistribution in mammals. In particular, the present invention relates to nucleic acids (for example, DNA, RNA, oligonucleotides, polynucleotides) or characteristic portions thereof as described herein, obtained from natural sources, recombinantly produced or chemically synthesized which encode a WIP or functional portion thereof.

Nucleic acids referred to herein as "isolated" are nucleic acids substantially free of (separated away from) the nucleic acids of the genomic DNA or cellular RNA of their biological source of origin (for example, as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis or by combinations of biological and chemical methods, and recombinantly produced nucleic acids which are isolated (see for example, Daugherty, B. L. et al., *Nucleic Acids Res.*, 19(9):2471–2476 (1991); Lewis, A. P. and J. S. Crowe, *Gene*, 101: 297–302 (1991)). Nucleic acids referred to herein as "recombinant" are nucleic acids which have been produced by recombinant DNA methodologies (recombinantly produced). Recombinant DNA methodologies include, for example, expression of WIP in a host cell containing or modified to contain DNA or RNA encoding WIP or expression of WIP using polymerase chain reaction (PCR) techniques.

This invention includes characteristic portions of the nucleic acids described herein. As used herein, a "characteristic portion" of nucleic acids described herein refers to portions of a nucleotide sequence which encode a protein or polypeptide having at least one property, function or activity characteristic of WIP (for example, the ability of WIP a) to bind WASP, profilin and/or Nck; b) increase F-actin content in lymphocytes; c) increase cellular content of polymerized actin; d) increase appearance of cerebriform projections the on cell surface containing F-actin). In addition, the term includes a nucleotide sequence which, through the degeneracy of the genetic code, encodes the same peptide as a peptide whose sequence is presented herein (for example, SEQ ID NO: 1). The nucleic acids described herein may also contain a modification of the molecule such that the resulting gene product is sufficiently similar to that encoded by the unmodified sequence that it has essentially the same activity as the unmodified sequence. An example of such a modification would be a "silent" codon substitution or an amino acid substitution, for instance, substitution of one codon encoding a hydrophobic amino acid to another codon encoding the same hydrophobic amino acid or substitution of one acidic amino acid for another acidic amino acid. See Ausubel, F. M., et al, *Current Protocols in Molecular Biology*, Greene Publ. Assoc. and Wiley-Interscience 1989.

In one embodiment, the nucleic acid or characteristic portion thereof encodes a protein or polypeptide having at least one property, activity or function characteristic of a WIP (as defined herein), such as activity or function characteristic of a WIP (as defined herein), such as the ability of WIP to a) bind WASP, profilin and/or Nck; b) increase F-actin content in lymphocytes; c) increase cellular content of polymerized actin; d) increase appearance of cerebriform projections on the cell surface containing F-actin. In a particular embodiment the characteristic portion which encodes a protein or polypeptide having at least one property, activity or function characteristic of WIP comprises at least 10 consecutive nucleotides in the coding region of SEQ ID NO: 1 which are 5' of nucleotide 380 of SEQ ID NO: 1.

The present invention also relates more specifically to isolated nucleic acids or a characteristic portion thereof, which encode mammalian WIP or variants thereof.

The invention relates to isolated nucleic acids that:

(1) hybridize to (a) a nucleic acid encoding a WIP (for example, human), such as a nucleic acid having a nucleotide sequence as set forth or substantially as set forth in FIGS. 1A–1B (SEQ ID NO:1); (b) the complement of the sequence of (a); or (c) characteristic portions of either of the foregoing (for example, a portion comprising the open reading frame);

(2) encode a protein or polypeptide having at least one property, activity of function characteristic of a WIP protein (for example, the ability of WIP to a) bind WASP, profilin and/or Nck; b) increase F-actin content in lymphocytes; c) increase cellular content of polymerized actin; d) increase appearance of cerebriform projections on the cell surface containing F-actin)

(3) encode a polypeptide having the amino acid sequence of a mammalian WIP (for example, SEQ ID NO:2); or (4) have a combination of these characteristics.

In one embodiment, the nucleic acid shares at least about 75% nucleotide sequence similarity, preferably 80%–85% nuc;eotide sequence similarity and more preferably, at least about 90% nucleotide sequence similarity, to the sequence shown in FIGS. 1A–1B (SEQ ID NO:1). Isolated nucleic acids meeting these criteria include nucleic acids having sequences identical to sequences of naturally occurring mammalian WIP.

The present invention also relates to variants of the naturally occurring sequences which encode WIP (for example, mammalian, such as human). Such variants include mutants differing by the addition, deletion or substitution of one or more residues, modified nucleic acids in which one or more residues are modified (for example, DNA or RNA analogs), and mutants comprising one or more modified residues.

Nucleic acids of the present invention may be RNA or DNA (for example, cDNA, genomic DNA, and synthetic DNA). The DNA may be double-stranded or single-stranded and, if single stranded, may be the coding strand or non-coding (anti-sense) strand. The coding sequence which encodes the polypeptide may be identical to the coding sequence shown in FIGS. 1A–1B (SEQ ID NO:1) or may be a different coding sequence which, as a result of the redundancy or degeneracy of the genetic code, encodes the same polypeptide as the polypeptide encoded by the DNA of FIGS. 1A–1B.

The nucleic acid (polynucleotide) which encodes a WIP polypeptide encoded by the WIP cDNA may include: only the coding sequence of a polypeptide; the coding sequence for a polypeptide and additional coding sequence such as a leader or secretory sequence; the coding sequence for a polypeptide (and optionally additional coding sequence) and non-coding sequence, such as introns or non-coding sequence 5' and/or 3' of the coding sequence.

Nucleic acids of the present invention, including those which hybridize to a selected nucleic acid as described above, can be detected or isolated under high stringency conditions or moderate stringency conditions, for example. "High stringency conditions" and "moderate stringency conditions" for nucleic acid hybridizations are explained at pages 2.10.1–2.10.16 (see particularly 2.10.8–11) and pages 6.3.1–6 in *Current Protocols in Molecular Biology* (Ausubel, F. M. et al., eds., Vol. 1, Suppl. 26, 1991), the teachings of which are hereby incorporated by reference. Factors such as probe length, base composition, percent mismatch between the hybridizing sequences, temperature and ionic strength influence the stability of nucleic acid hybrids. Thus, high or moderate stringency conditions can be determined empirically, and depend in part upon the characteristics of the known nucleic acid (for example, DNA) and the other nucleic acids to be assessed for hybridization thereto.

Nucleic acids of the present invention that are characterized by their ability to hybridize (for example, under high or moderate stringency conditions) to (a) a nucleic acid encoding a WIP (for example, the nucleic acid depicted in FIGS. 1A–1B (SEQ ID NO: 1) or characteristic portions thereof); (b) the complement of the nucleic acids of (a); or (c) a portion thereof, can also encode a protein or polypeptide having at least one property, activity or function characteristic of a mammalian WIP as defined herein, such as the ability of WIP to a) bind WASP, profilin and/or Nck; b) increase F-actin content in lymphocytes; c) increase cellular content of polymerized actin; c) increase appearance of cerebriform projections on the cell surface containing F-actin. In one embodiment the nucleic acid encodes a polypeptide which retains substantially the same biological function or activity as the polypeptide encoded by the DNA of FIGS. 1A–1B (SEQ ID NO:1). In another embodiment, the nucleic acid encodes a WIP and hybridizes under stringent conditions with at least 10 consecutive nucleotides in the coding region of the complement strand of SEQ ID NO: 1 which are 5' of nucleotide 380 of the complement of SEQ ID NO:1.

Nucleic acids of the present invention can be used in the production of proteins or polypeptides. For example, a nucleic acid (for example, DNA) encoding a mammalian WIP can be incorporated into various constructs and vectors created for further manipulation of sequences or for production of the encoded polypeptide in suitable host cells as described above.

A further embodiment of the invention is antisense nucleic acid, which is complementary, in whole or in part, to a WIP sense strand, and can hybridize with it. The antisense strand hybridizes to DNA, or its RNA counterpart (i.e., wherein T residues of the DNA are U residues in the RNA counterpart). When introduced into a cell, antisense nucleic acid hybridizes to and inhibits the expression of the sense strand. Antisense nucleic acids can be produced by standard techniques.

In another embodiment, the antisense nucleic acid is wholly or partially complementary to and can hybridize with a target nucleic acid which encodes a mammalian WIP. For example, antisense nucleic acid can be complementary to a target nucleic acid having the sequence shown as the open reading frame in FIGS. 1A–1B (SEQ ID NO:1) or to a portion thereof sufficient to allow hybridization.

The nucleic acids can also be used as probes (for example, for in situ hybridization) to assess the presence of levels of WIP in a host. The nucleic acids can also be used as probes to detect and/or isolate (for example, by hybridization with RNA or DNA) polymorphic or allelic variants, for example, in a sample (for example, blood, such as peripheral blood mononuclear cells (PMBC)) obtained from a host (for example, a human). Moreover, the presence or level of a particular variant in a sample(s) obtained from an individual, as compared with the presence or level in a sample(s) from normal individuals, can be indicative of an association between a disease or condition and a particular variant, which in turn can be used in the diagnosis of the disease or condition.

The present invention also relates to isolated (for example, pure, essentially pure) proteins or polypeptides designated WIP and variants of WIP. In a preferred embodiment, the isolated proteins of the present invention have at least one property, activity or function characteristic of a WIP (as defined herein), such as the ability of WIP to a) bind WASP, profilin and/or Nck; b) increase F-actin content in lymphocytes; c) increase cellular content of polymerized actin; d) increase appearance of cerebriform projections on the cell surface containing F-actin.

Proteins or polypeptides referred to herein as "isolated" are proteins or polypeptides purified to a state beyond that in which they exist in mammalian cells. "Isolated" proteins or polypeptides include proteins or polypeptides obtained by methods described herein, similar methods or other suitable methods. They include essentially pure proteins or polypeptides, proteins or polypeptides produced by chemical synthesis (for example, synthetic peptides), or by combinations of biological and chemical methods, and recombinant proteins or polypeptides which are isolated. The proteins can be obtained in an isolated state of at least about 50% by weight, preferably at least about 75% by weight, and more preferably, in essentially pure form. Proteins or polypeptides referred to herein as "recombinant" are proteins or polypeptides produced by the expression of recombinant nucleic acids.

As used herein, "WIP" protein refers to naturally occurring or endogenous WIPs, proteins having an amino acid sequence which is the same as that of a naturally occurring or endogenous corresponding WIP (for example, recombinant proteins).

In addition, the present invention relates to functional variants of each of the foregoing (for example, functional fragments and/or mutants produced via mutagenesis and/or recombinant techniques). Accordingly, the present invention relates to WIP, glycosylated or unglycosylated WIP, polymorphic or allelic variants, and other isoforms of WIP (for example, produced by alternative splicing or other cellular processes), and functional fragments.

Naturally occurring or endogenous WIPs include wild type proteins such as WIP, polymorphic or allelic variants and other isoforms which occur naturally in mammals (for example, primate, preferably human, murine, bovine). Such proteins can be recovered from a source in which WIP is naturally produced, for example. These mammalian proteins have the same amino acid sequence as naturally occurring or endogenous corresponding mammalian WIP.

"Functional variants" of WIP include functional fragments, functional mutant proteins, and/or functional fusion proteins. Generally, fragments or portions of WIP encompassed by the present invention include those having one or more amino acid deletions relative to the naturally occurring WIP (such as N-terminal, C-terminal or internal deletions). Fragments or portions in which only contiguous amino acids have been deleted or in which non-contiguous amino acids have been deleted relative to naturally occurring WIP are also encompassed by the invention.

Generally, mutants or derivatives of WIP, encompassed by the present invention include natural or artificial variants differing by the addition, deletion and/or substitution of one or more contiguous or non-contiguous amino acid residues, or modified polypeptides in which one or more residues is modified, and mutants comprising one or more modified residues. For example, mutants can be natural or artificial variants of WIP which differ from naturally occurring WIP by the addition, deletion and/or substitution of one or more contiguous or non-contiguous amino acid residues.

A "functional fragment or portion", "functional mutant" and/or "functional fusion protein" of a WIP refers to an isolated protein or oligopeptide which has at least one property, activity or function characteristic of a mammalian WIP, such as the ability of WIP to a) bind WASP, profilin and/or Nck; b) increase F-actin content in lymphocytes; c) increase cellular content of polymerized actin; d) increase appearance of cerebriform projections on the cell surface containing F-actin.

Suitable fragments or mutants can be identified by screening. For example, the N-terminal, C-terminal, or internal regions of the protein can be deleted in a step-wise fashion and the resulting protein or polypeptide can be screened using a suitable assay, for example, by measuring the ability of the fragment or mutant to bind WASP, profilin and/or Nck; increase F-actin content in lymphocytes; increase cellular content of polymerized actin; increase appearance of cerebriform projections on cell surface containing F-actin. Where the resulting protein displays activity in the assay, the resulting protein ("fragment") is functional.

The invention also encompasses fusion proteins, comprising a WIP as a first moiety, linked to a second moiety not occurring in the WIP found in nature. Thus, the second moiety can be, for example, an amino acid, oligopeptide or polypeptide. The first moiety can be in an N-terminal location, C-terminal location or internal location of the fusion protein. In one embodiment, the fusion protein comprises a WIP or portion thereof as the first moiety, and a second moiety comprising an affinity ligand (for example, an enzyme, an antigen, epitope tag) joined to the first moiety. Optionally, the two components can be joined by a linker.

Examples of "human WIP" include proteins having an amino acid sequence as set forth or substantially as set forth in FIG. 1D (SEQ ID NO: 2) and functional portions thereof. In preferred embodiments, a human WIP or a variant thereof has an amino acid sequence which has at least about 75% identity, preferably at least about 85% identity and more preferably at least about 90% identity, to the protein shown in FIG. 1D (SEQ ID NO: 2).

Another aspect of the invention relates to a method of producing a WIP or variant (for example, portion) thereof. Recombinant protein can be obtained, for example, by the expression of a recombinant DNA molecule encoding a WIP or variant thereof in a suitable host cell.

Constructs suitable for the expression of a WIP or variant thereof are also provided. The constructs can be introduced into a suitable host cell, and cells which express a recombinant WIP or variant thereof, can be produced and maintained in culture. Such cells are useful for a variety of purposes, and can be used in the production of protein for characterization, isolation and/or purification, (for example, affinity purification), and as immunogens, for instance. Suitable host cells can be procaryotic, including bacterial cells such as *E. Coli B. subtilis* and or other suitable bacteria (for example, *Streptococci*) or eucaryotic, such as fungal or yeast cells (for example, *Pichia pastoris, Aspergillus species, Saccharomyces cerevisiae, Schizosaccharomyces pombe, Neurospora crassa*), or other lower eucaryotic cells, and cells of higher eucaryotes such as those from insects (for example, Sf9 insect cells) or mammals (for example, Chinese hamster ovary cells (CHO), COS cells, HuT 78 cells, 293 cells). (See, for example, Ausubel, F. M. et al., eds. *Current Protocols in Molecular Biology*, Greene Publishing Associates and John Wiley & Sons Inc., (1993)).

Host cells which produce a recombinant WIP or variants thereof can be produced as follows. For example, nucleic acid encoding all or part of the WIP or a functional portion thereof can be inserted into a nucleic acid vector, for example, a DNA vector, such as a plasmid, virus or other suitable replicon for expression. A variety of vectors is available, including vectors which are maintained in single copy or multiple copy, or which become integrated into the host cell chromosome.

The transcriptional and/or translational signals of a mammalian WIP gene can be used to direct expression. Alternatively, suitable expression vectors for the expression of a nucleic acid encoding all or part of the desired protein are available. Suitable expression vectors can contain a number of components, including, but not limited to, one or more of the following: an origin of replication; a selectable marker gene; one or more expression control elements, such as a transcriptional control element (for example, a promoter, an enhancer, terminator), and/or one or more translation signals; a signal sequence or leader sequence for membrane targeting or secretion (of mammalian origin or from a heterologous mammal or non-mammalian species). In a construct, a signal sequence can be provided by the vector, the WIP coding sequence, or other source.

A promoter can be provided for expression in a suitable host cell. Promoters can be constitutive or inducible. The promoter is operably linked to nucleic acid encoding the WIP or variant thereof, and is capable of directing expression of the encoded polypeptide in the host cell. A variety of suitable promoters for procaryotic (for example, lac, tac, T3, T7 promoters for *E. coli*) and eucaryotic (for example, yeast alcohol dehydrogenase (ADH1), SV40, CMV) hosts is available.

In addition, the expression vectors typically comprise a selectable marker for selection of host cells carrying the vector, and in the case of a replicable expression vector, also comprise an origin of replication. Genes encoding products which confer antibiotic or drug resistance are common selectable markers and may be used in procaryotic (for example, β-lactamase gene (ampicillin resistance), Tet gene for tetracycline resistance) and eucaryotic cells (for example, neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (for example, LEU2, URA3, HIS3) are often used as selectable markers in yeast. Use of viral (for example, baculovirus) or phage vectors, and vectors which are capable of integrating into the genome of the host cell, such as retroviral vectors, are also contemplated. The present invention also relates to cells carrying these expression vectors.

For example, a nucleic acid encoding a mammalian WIP or variant thereof is incorporated into a vector, operably linked to one or more expression control elements, and the construct is introduced into host cells which are maintained under conditions suitable for expression, whereby the encoded polypeptide is produced. The construct can be introduced into cells by a method appropriate to the host cell selected (for example, transformation, transfection, electroporation, infection). For production of a protein, host cells comprising the construct are maintained under conditions appropriate for expression, (for example, in the presence of inducer, suitable media supplemented with appropriate salts, growth factors, antibiotic, nutritional supplements, etc.). The encoded protein (for example, human WIP) can be isolated from the host cells or medium.

Fusion proteins can also be produced in this manner. For example, some embodiments can be produced by the insertion of a WIP cDNA or portion thereof into a suitable expression vector, such as Bluescript®II SK+/−(Stratagene), pGEX-4T-2 (Pharmacia), pcDNA-3 (Invitrogen) and pET-15b (Novagen). The resulting construct can then be introduced into a suitable host cell for expression. Upon expression, fusion protein can be isolated or purified from a cell lysate by means of a suitable affinity matrix (see for example, *Current Protocols in Molecular Biology* (Ausubel, F. M. et al., eds., Vol. 2, Suppl. 26, pp. 16.4.1–16.7.8 (1991)). In addition, affinity labels provide a means of detecting a fusion protein. For example, the cell surface expression or presence in a particular cell fraction of a fusion protein comprising an antigen or epitope affinity label can be detected by means of an appropriate antibody.

As described in the Examples, a cDNA library constructed from a human lymphoma T cell line was screened using full-length WASP cDNA obtained from peripheral blood T cells to identify novel WASP interacting protein(s). This resulted in identification of six clones. The two largest cDNAs, designated WIP2 (1.7 kb) and WIP4 (1.6 kb), were further characterized. See Example 1. WIP2 and WIP4 cDNAs were shown to be the products of the same gene; the WIP4 protein coding sequence was completely contained within WIP2. FIG. 1C is a schematic representation of full-length WIP, WIP2, WIP4 cDNAs, as well as Prp12 cDNA, which is a partial human cDNA isolated from tonsillar B cells whose function is unknown.

The amino acid sequence of WIP is represented in FIG. 1D. The predicted WIP protein product is a 503 aa long proline-rich protein with a calculated molecular weight of approximately 52 kd. Analysis of the WIP protein product showed that the N-terminal region contains two stretches (28 and 17 amino acid residues in length) that are highly homologous to corresponding stretches in the N-terminal region of the yeast protein verprolin, which is involved in cytoskeletal organization. The first WIP verprolin homology domain includes the motif KLKK (SEQ ID NO: 4), which was originally identified in thymosin-β4 as a motif critical for actin binding. This further supports direct interaction of WIP with actin. WIP also contains two APPPPP (SEQ ID NO: 3) sequences (denoted by asterisk in FIG. 1D) which have been shown to bind profilin, a protein that regulates actin polymerization.

Further analysis showed that WIP contains putative SH3 binding motifs with the sequence PPPYXP and a unique proline-rich motif, GRSGPXPPXP (SEQ ID NO: 7), which is repeated three times in WIP. (See FIG. 1F) The latter motif occurs twice in WASP and has been implicated in binding of WASP to the SH3 domain-containing proteins fyn, fgr and phospholipase. The presence of conserved SH3 binding domains in WIP suggests WIP may link the signal transduction machinery to the cytoskeleton.

Work also described herein showed that WIP associates with WASP in vitro and in vivo. (See Example 2) The WIP binding site was identified by examining truncations of WASP, as also described in Example 2. Results show that the WIP binding region lies within the N-terminal 170 amino acid residues of WASP (FIG. 2A). This region lacks the GBD domain (amino acids 238–257) and, thus, the WIP binding site on WASP is distinct from the Cdc42 binding site. Both the WHI domain and the proline-rich amino acid 139–270 region were shown to be necessary, but not sufficient, for WIP binding. The affinity of WASP for WIP was sharply reduced when the N terminal 46 amino acids were deleted (resulting in disruption of the PH domain but not the WHI domain). This suggests that amino acid residues 1–46 are required for optimal binding of WASP to WIP.

Also described in Example 2 is identification of the WASP binding region of WIP. The carboxy terminal amino acid residue of WIP (in WIP4, amino acid residues 321–503) are sufficient for WASP binding. Initial analysis showed that WASP binding region lies within amino acid residues 377–503 of WIP. Further analysis showed that the WASP binding region lies within amino acid residues 415 to 488.

As described in Example 3, expression of WIP transcripts in human tissues was assessed, using full-length WIP cDNA as probe. Results show that three species of mRNA (estimates sizes 2.4 kb, 3.5 kb, 5 kb) are present in all tissues tested. The different mRNA species appear to be splice variants. WASP is not expressed in non-hematopoietic tissues, suggesting WIP has interactions with partners other than WASP.

Expression of WIP has been shown to cause actin polymerization, as described in Example 4. There was an increase in baseline F-actin content in β lymphocytes that overexpressed full length WIP, but not in control transfected cells. The N-terminal region of WIP was required for the effect of WIP overexpression on F-actin content. Overexpression of WIP4 which lacks the first 320 amino acid residues and, therefore, lacks the actin binding KLKK (SEQ ID NO: 4) motif and one of two profilin binding ABM-2 sequences, did not cause an increase in F-actin content. WIP has also been shown to bind profilin, which has a critical role in actin polymerization. (See Example 5).

WIP mRNA is expressed in many tissues, although its level of expression varies between tissues. The finding that WASP is expressed only in hematopoietic cells suggests that WIP may interact with partners other than WASP, for example N-WASP, which we recently showed to interact with WIP. Overexpression of WIP exerts powerful effects on the actin cytoskeleton. These include increase in the cellular content of polymerized actin and appearance of cerebriform projections on the cell surface containing F-actin. The effects of WIP overexpression on the actin cytoskeleton required the N-terminal end of the molecule (aa 320), which contains the actin binding KLKK (SEQ ID NO: 4) motif. A number of proteins have been shown to assemble into a spatial actin monomer delivery system. These proteins, which include Mena and VASP, bind profilin via a proline rich ABM-2 motif, XPPPPP (SEQ ID NO: 14), where X denotes G, A, L or S (Gertler, F. B., Niebuhr, K., Reinhard, M., Wehland, J. & Soriano, P. (1996) Cell, 87: 227–239; Purich, D. L. and Southwick, F. S. (1997) Biochem. Biophys. Res. Comm., 231:686–691; Reinhard, M., Giehl, K., Abel, K., Haffner, C., Jarchau, T., Hoppe, V., Jockusch, B. M. & Walter, U. (1995) EMBO J., 14 1583–1589). The sequence APPPPP (SEQ ID NO: 3) is represented twice in WIP, once at the N-terminal end and once in the C-terminal region (FIG. 1D). Immobilized WIP bound profilin from cell lysates, suggesting a direct interaction of WIP with profilin. Recombinant profilin was affinity precipitated from bacterial cell lysates by MBP-WIP, further indicating that WIP interacts directly with profilin. Thus, WIP may modulate actin dynamics by direct interaction with actin, via the KLKK (SEQ ID NO: 4) motif, as well as with profilin, and possibly with other proteins that regulate actin polymerization, such as WASP.

The platelet and lymphocyte structural abnormalities in WAS support a functional link between WASP and the actin cytoskeleton. In addition, T lymphocytes from WAS patients fail to proliferate to immobilized anti-CD3 (Molina, I. J., Sancho, J., Terhorst, C., Rosen, F. S. & Remold-O'Donnell, E. (1993) J. Immunol., 151: 4383–4390), a response which depends on actin cytoskeleton rearrangement (Parsey, M. V. & Lewis, G. K. (1993) J. Immunol., 151: 1881–1893; Phatak, P. D. & Packman, C. H. (1994) J. Cell. Physiol., 159: 365–370). The mechanism by which WASP modulates the actin cytoskeleton is unclear. Although WASP overexpression induces the actin clusters that contain WASP (Symons, M., Derry, J. M. J., Kariak, B., Jiang, S., Lemahieu, V., McCormick, F., Francke, U. & Abo, A. (1996) Cell, 84: 723–734), no evidence exists for direct interaction between WASP and actin; however, N-WASP has been shown to interact with actin in vitro (Symons, M., Derry, J. M. J., Kariak, B., Jiang, S., Lemahieu, V., McCormick, F., Francke, U. & Abo, A. (1996) Cell, 84: 723–734). WIP binds WASP and overexpression of WIP induces actin cytoskeletal changes. Therefore, WIP may play an important role in linking WASP to the actin cytoskeleton. The actin binding KLKK (SEQ ID NO: 4) motif and one of the two profilin binding ABM-2 motifs in WIP are located in proximity to each other, just as they are in members of the Ena/VASP family. Simultaneous binding of profilactin by WIP may promote actin polymerization by increasing the local concentration of actin monomers. Actin polymerization by a WASP-WIP complex may further be enhanced by the recruitment of profilin to the ABM-2 motifs in WASP.

Cytoskeletal rearrangement is triggered by a variety of signaling pathways induced by external stimuli, such as growth factors, stress and adhesion through integrins (Zigmond, S. H. (1996) Curr. Opin. Cell. Biol., 8: 66–73), and is mediated by small GTPases. WIP does not contain any discernable GBD domain; thus direct interaction of WIP with GTpases is unlikely. However, WASP may bridge Cdc42 to WIP, allowing Cdc42 to regulate WIP function. The WASP-WIP complex may be targeted by stimuli that activate Cdc42 to locate to the actin cytoskeleton via interactions between the WH1 domain of WASP and the proline rich ABM-1 motifs of structural proteins such as zyxin and vinculin (Purich, D. L. and Southwick, F. S. (1997) Biochem. Biophys. Res. Comm., 231:686–691). The presence of SH3 binding motifs in both WIP and WASP suggests that the WASP-WIP complex couples additional signaling pathways to the actin cytoskeleton.

WIP also binds to Nck, an adaptor protein, and induces actin clusters after PDGF stimulation (see Example 6). Nck is a ubiquitous adaptor molecule composed of three Src homology 3 (SH3) domains followed by a single SH2 domain. Via its SH2 domain, Nck links tyrosine phosphorylated receptors to effector proteins that contain SH3 domain binding proline-rich sequences. Recombinant Nck has been demonstrated to have precipitated endogenous WIP, which is a proline-rich protein, from BJAB cell lysates. Nck binds to WIP, through its second SH3 domain, at a site (aa 321 to 415) different from the WASP binding site (aa 416 to 488). As discussed herein, WIP has been shown to associate with the actin polymerization regulatory protein, profilin, and to induce actin polymerization and cytoskeletal reorganization in lymphoid cells. PDGF stimulation induces ruffles formation mediated by activation of the small GTPase Rac. The over-expression of WIP in 3T3 fibroblasts has been demonstrated to induce actin clustering after PDGF stimulation. The presence of profilin in Nck precipitates indicates that Nck couples extracellular signals to the cytoskeleton via its interaction with WIP and profilin.

WIP has also been demonstrated to complement verprolin function in yeast cells. The ability of WIP to complement verprolin is dependent on the actin-binding amino terminal region of the molecule. WIP shows moderate homology to the yeast protein verprolin. However, the N-terminal region of WIP and verprolin are highly conserved. Verprolin is involved in cytoskeletal organization because vrp1 conditional mutants fail to grow at the restrictive temperature of 37° C., have abnormal actin cytoskeletal organization, show defective bud formation, and have defects in endocytosis. Both WIP and verprolin affect the actin based cytoskeleton. It is likely that WIP is the functional equivalent of verprolin as WIP has been shown to complement the growth, the endocytotic function, and the induction of bipolar budding in vrp1 mutant yeast cells.

The WIP nucleic acids (DNA, RNA) and protein can be used in a variety of ways. It is known that 13% of WAS patients who survive beyond infancy are susceptible to lymphoreticular malignancies (Ochs, H. D., 1998. The Wiskott-Aldrich Syndrome. *SpringerSemin. Immunopathol.*, 19:435–458) suggesting that WASP and by extension WIP has a role in the etiology of some cancers. Since WIP has the potential to bind many cellular signaling molecules (for example, SH3 containing proteins as exemplified by Nck binding), it is likely that WIP participates in the coordination of processes such as gene transcription adhesion motility, etc. Many of these essential processes display impaired regulation in cancer. Therefore, it is likely that WIP plays a role in cancer and therefore, agents which alter the effect of WIP can be used in the treatment of cancer.

Furthermore, WIP nucleic acids and proteins can be used to identify agents (for example, molecules) that alter or modulate (enhance, inhibit) WIP expression and/or function. For example, WIP can be expressed in a host cell and effects of test compounds on the ability of WIP to bind WASP, profilin and/or Nck; increase F-actin content in lymphocytes; increase cellular content of polymerized actin; and/or increase appearance of cerebriform projections on cell surface containing F-actin in the host cell could be assessed using the methods described herein.

In one embodiment, the present invention relates to a method of identifying an agent which alters WIP activity, wherein a nucleic acid construct comprising nucleic acid which encodes a WIP is introduced into a host cell(s). The host cells produced are maintained under conditions appropriate for expression of the encoded WIP, whereby the nucleic acid is expressed. The host cells are then contacted with a compound to be assessed (an agent) and the ability of WIP to bind WASP, profilin and/or Nck; increase F-actin content in lymphocytes; increase cellular content of polymerized actin; increase appearance of cerebriforn projections on cell surface containing F-actin in the cells is detected in the presence of the compound to be assessed.

A control can be used in the methods of detecting agents which alter WIP activity. For example, the control sample includes the same reagents but lacks the compound or agent being assessed; it is treated in the same manner as the test sample.

Also encompassed by the present invention is an agent which interacts with WIP directly or indirectly, and inhibits or enhances WIP expression and/or function. In one embodiment, the agent is an inhibitor which interferes with WIP directly (for example, by binding WIP) or indirectly (for example, by blocking the ability of WIP to function). In a particular embodiment, an inhibitor of WIP is an antibody specific for WIP or a functional portion of WIP; that is, the antibody binds the WIP protein. For example, the antibody can be specific for the protein encoded by the amino acid sequence of human WIP (SEQ ID NO: 2) or portions thereof. Alternatively, the inhibitor can be an agent other than an antibody (for example, small organic molecule, protein or peptide) which binds WIP and blocks its activity. For example, the inhibitor can be an agent which mimics WIP structurally, but lacks its function. Alternatively, it can be an agent which binds to or interacts with a molecule which WIP normally binds with or interacts with, thus blocking WIP from doing so and preventing it from exerting the effects it would normally exert.

In another embodiment, the agent is an enhancer of WIP which increases the activity of WIP (increases the effect of a given amount or level of WIP), increases the length of time it is effective (by preventing its degradation or otherwise prolonging the time during which it is active) or both either directly or indirectly. For example, WIP nucleic acids and proteins can be used to identify agents which enhance the ability of WIP to bind WASP, profilin and/or Nck; increase F-actin content in lymphocytes; increase cellular content of polymerized actin; increase appearance of cerebriform projections on the cell surface containing F-actin.

In another embodiment, the sequences described herein can be used to detect WIP or DNA encoding WIP in a sample. For example, a labeled nucleic acid probe having all or a functional portion of the nucleotide sequence of WIP can be used in a method to detect WIP in a sample. In one embodiment, the sample is treated to render the nucleic acids in the sample available for hybridization to a nucleic acid probe, which can be DNA or RNA. The resulting treated sample is combined with a labeled nucleic acid probe having all or a portion of the nucleotide sequence of WIP, under conditions appropriate for hybridization of complementary sequences to occur. Detection of hybridization of nucleic acids from the sample with the labeled nucleic probe indicates the presence of WIP in a sample. The presence of WIP mRNA is indicative of WIP expression. Such a method can be used, for example, as a screen for normal or abnormal expression of WIP, which can be associated with a disease caused by the abnormal expression of WIP.

Alternatively, a method of detecting WIP in a sample can be accomplished using an antibody directed against WIP or a portion of WIP. Detection of specific binding to the antibody indicates the presence of WIP in the sample (for example, ELISA). This could reflect a pathological state associated with WIP or a deficiency of WIP, and thus, can be used diagnostically.

The sample for use in the methods of the present invention includes a suitable sample from, for example, a mammal, particularly a human. For example, the sample can be blood (for example, PMBC), tissue and lymph and/or urine.

The WIP sequences of the present invention can also be used to generate nonhuman gene knockout animals, such as mice, which lack WIP and transgenically overexpress WIP. For example, such WIP gene knockout mice can be generated and used to obtain further insight into the function of WIP as well as assess the specificity of WIP activators and inhibitors. Also, overexpression of WIP (for example, human WIP) in transgenic mice can be used as a means of creating a test system for WIP activators and inhibitors (for example, against human WIP). In addition, the WIP gene can be used to clone the WIP promoter/enhancer in order to identify regulators of WIP transcription. WIP gene knockout animals include animals which completely or partially lack the WIP gene and/or WIP activity or function.

The present invention also provides a transgenic non-human mammal which lacks a functional WIP gene referred to herein as a "transgenic non-human WIP knockout mammal" or a "WIP knockout mammal". In a particular embodiment, the genome of the WIP knockout mammal comprises at least one non-functional allele for the endogenous WIP gene. Thus, the invention provides a source of cells (for example, tissue, cells, cellular extracts, organelles) and animals useful for elucidating the function of WIP in intact animals whose genomes comprise a wild-type WIP gene. Further aspects of the invention provide a method for the identification of agents (for example, diagnostic or therapeutic agents) which inhibit or mimic WIP activity; and a method of treating diseases or conditions associated with WIP function.

Any suitable non-human mammal can be used to produce the WIP knockout mammal described herein. For example, a suitable mammal can be, a mouse (mice), a rat, a rabbit, a pig, a sheep, a goat or a cow.

As used herein, the term "gene" refers to DNA sequences which encode the genetic information (for example, nucleic acid sequence) required for the synthesis of a single protein (for example, polypeptide chain). The term "WIP gene" refers to a particular mammalian gene which comprises a DNA sequence which encodes WIP. An "allele" is an alternative from of gene found at the same locus of a homologous chromosome. Homologous chromosomes are chromosomes which pair during meiosis and contain identical loci. The term locus connotes the site (for example, location) of a gene on a chromosome.

As used herein the terms "transgenic non-human WIP knockout mammal" and "WIP knockout mammal" refer to a mammal whose genome comprises a disrupted or inactivated WIP gene. Those of skill in the art will recognize that the term "knockout" refers to the functional inactivation of the gene. The disruption introduces a chromosomal defect (for example, mutation or alteration) in the WIP gene at a point in the nucleic acid sequence that is important to either the expression of the WIP gene or the production of a functional WIP protein (for example, polypeptide). Thus, the introduction of the disruption inactivates the endogenous target gene (for example, WIP gene).

As used herein the terms "disruption", "functional inactivation", "alteration" and "defect" connote a partial or complete reduction in the expression and/or function of the WIP polypeptide encoded by the endogenous gene of a single type of cell, selected cells (for example, T cells or B cells) or all of the cells of a non-human transgenic WIP knockout animal. Thus, according to the instant invention the expression or function of the WIP gene product can be completely or partially disrupted or reduced (for example, by 50%, 75%, 80%, 90%, 95% or more) in a selected group of cells (for example, a tissue or organ) or in the entire animal. As used herein, the term "a functionally disrupted WIP gene" includes a modified WIP gene which either fails to express any polypeptide product or which expresses a truncated protein having less than the entire amino acid polypeptide chain of a wild-type protein and is non-functional (partially or completely non-functional).

Disruption of the WIP gene can be accomplished by a variety of methods known to those of skill in the art. For example, gene targeting using homologous recombination, mutagenesis (for example, point mutation) and anti-sense technology can be used to disrupt a WIP gene.

More specifically, the invention provides a transgenic knockout mammal whose genome comprises either a homozygous or heterozygous disruption of its WIP gene. A knockout mammal whose genome comprises a homozygous disruption is characterized by somatic and germ cells which contain two nonfunctional (disrupted) alleles of the WIP gene while a knockout mutant whose genome comprises a heterologous disruption is characterized by somatic and germ cells which contain one wild-type allele and one nonfunctional allele of the WIP gene.

As used herein, the term "genotype" refers to the genetic makeup of an animal with respect to the WIP chromosomal locus. More specifically the term genotype refers to the status of the animal's WIP alleles, which can either be intact (for example, wild-type or +/+); or disrupted (for example, knockout) in a manner which confers either a heterozygous (for example, +/−); or homozygous (−/−) knockout genotype.

The present invention also provides methods of producing a transgenic non-human mammal which lacks a functional WIP gene. Briefly, the standard methodology for producing a transgenic embryo requires introducing a targeting construct, which is designed to integrate by homologous recombination with the endogenous nucleic acid sequence of the targeted gene, into a suitable ES cells. The ES cells are then cultured under conditions effective for homologous recombination between the recombinant nucleic acid sequence of the targeting construct and the genomic nucleic acid sequence of the host cell chromosome. Genetically engineered stem cell that are identified as comprising a knockout genotype which comprises the recombinant allele is introduced into an animal, or ancestor thereof, at an embryonic stage using standard techniques which are well known in the art (for example, by microinjecting the genetically engineered ES cell into a blastocyst). The resulting chimeric blastocyst is then placed within the uterus of a pseudo-pregnant foster mother for the development into viable pups. The resulting viable pups include potentially chimeric founder animals whose somatic and germline tissue comprise a mixture of cells derived from the genetically-engineered ES cells and the recipient blastocyst. The contribution of the genetically altered stem cell to the germline of the resulting chimeric mice allows the altered ES cell genome which comprises the disrupted target gene to be transmitted to the progeny of these founder animals thereby facilitating the production of transgenic "knockout animals" whose genomes comprise a gene which has been genetically engineered to comprise a particular defect in a target gene.

In a particular embodiment of the present invention, a transgenic WIP knockout mammal is produced by introducing a targeting vector which disrupts the WIP gene into an ES cell thereby producing a transgenic stem cell. A transgenic ES cell which includes the disrupted WIP gene due to the integration of the targeting vector into its genome is selected and introduced into a blastocyst, thereby forming a chimeric blastocyst. The chimeric blastocyst is introduced into the uterus of a pseudo-pregnant mammal wherein the pseudo-pregnant mammal gives birth to a transgenic non-human mammal which lacks a functional WIP gene.

As a result of the disruption of the WIP gene, the WIP knockout mammal of the present invention can manifest a particular phenotype. The term phenotype refers to the resulting biochemical or physiological consequences attributed to a particular genotype. In one embodiment, the WIP knockout mammal has altered subcortical actin networks; disrupted TCR clustering and interaction between T lymphocytes (T cells) and antigen presenting cells (APCs), sometimes referred to as a supramolecular activation cluster (SMAC) or immunological synapse, such a disruption in the interaction can include the breadth and angle of the interaction; proliferation; altered B cell response to TD antigen stimulation, for example IgG isotype switching and proliferation; IL-2 secretion; F-actin content; polarization; and extension of cell protrusions.

One of skill in the art will easily recognize that the WIP gene can be disrupted in a number of different ways, any one of which may be used to produce the WIP knockout mammals of the present invention. For example, a transgenic knockout animal according to the instant invention can be produced by the method of gene targeting. As used herein the term "gene targeting" refers to a type of homologous recombination which occurs as a consequence of the introduction of a targeting construct (for example, vector) into a mammalian cell (for example, an ES cell) which is designed to locate and recombine with a corresponding portion of the nucleic acid sequence of the genomic locus targeted for alteration (for example, disruption) thereby introducing an exogenous recombinant nucleic acid sequence capable of conferring a planned alteration to the endogenous gene. Thus, homologous recombination is a process (for example, method) by which a particular DNA sequence can by replaced by an exogenous genetically engineered sequence. More specifically, regions of the targeting vector which have been genetically engineered to be homologous (for example, complimentary) to the endogenous nucleotide sequence of the gene which is targeted for disruption line up or recombine with each other such that the nucleotide sequence of the targeting vector is incorporated into (for example, integrates with) the corresponding position of the endogenous gene.

One embodiment of the present invention provides a vector construct (for example, a WIP targeting vector or WIP targeting construct) designed to disrupt the function of a wild-type (endogenous) mammalian WIP gene. In general terms, an effective WIP targeting vector comprises a recombinant sequence that is effective for homologous recombination with the WIP gene. For example, a replacement targeting vector comprising a genomic nucleotide sequence which is homologous to the target sequence operably linked to a second nucleotide sequence which encodes a selectable marker gene exemplifies an effective targeting vector. Integration of the targeting sequence into the chromosomal DNA of the host cell (for example, an ES cell) as a result of homologous recombination introduces an intentional disruption, defect or alteration (for example, insertion, deletion) into the sequence of the endogenous gene. One aspect of the present invention is to replace all or part of the nucleotide sequence of a non-human mammalian gene which encodes the WIP polypeptide. In a particular embodiment, exons 2, 3, 4, and/or 5 of the WIP gene are disrupted. In another embodiment, a segment including exons 2 to 5, including the start codon of the WIP gene, is removed.

One of skill in the art will recognize that any WIP genomic nucleotide sequence of appropriate length and composition to facilitate homologous recombination at a specific site that has been preselected for disruption can be employed to construct a WIP targeting vector. Guidelines for the selection and use of sequences are described for example in Deng and Cappecchi, *Mol. Cell. Biol.*, 12:3365–3371 (1992) and Bollag, et al., *Annu. Rev. Genet.*, 23:199–225 (1989). For example, a wild-type WIP gene can be mutated and/or disrupted by inserting a recombinant nucleic acid sequence (for example, a WIP targeting construct or vector) into all or a portion of the WIP gene locus. For example, a targeting construct can be designed to recombine with a particular portion within the enhancer, promoter, coding region, start codon, non-coding sequence, introns or exons of the WIP gene. Alternatively, a targeting construct can comprise a recombinant nucleic acid which is designed to introduce a stop codon after exon 2, 3, 4, or 5 of the WIP gene.

Suitable targeting constructs of the invention can be prepared using standard molecular biology techniques known to those of skill in the art. For example, techniques useful for the preparation of suitable vectors are described by Maniatis, et al., Molecular Cloning: A Laboratory Manual, Cold Spring Harbor Laboratory, Cold Spring Harbor, N.Y. Appropriate vectors include a replacement vector such as the insertion vector described by Capecchi, M. R., *Science*, 244:1288–92 (1989); or a vector based on a promoter trap strategy or a polyadenylation trap, or "tag-and-exchange" strategy as described by Bradley, et al., *Biotechnology*, 10:543–539 (1992); and Askew, et al., *Mol. Cell. Biol.*, 13:4115–5124 (1993).

One of skill in the art will readily recognize that a large number of appropriate vectors known in the art can be used as the basis of a suitable targeting vector. In practice, any vector that is capable of accommodating the recombinant nucleic acid sequence required to direct homologous recombination and to disrupt the target gene can be used. For example, pBR322, pACY164, pKK223-3, pUC8, pKG, pUC19, pLG339, pR290, pKC101 or other plasmid vectors can be used. Alternatively, a viral vector such as the lambda gt11 vector system can provide the backbone (for example, cassette) for the targeting construct.

According to techniques well known to those of skill in the art, genetically engineered (for example, transfected using electroporation or transformed by infection) ES cells, are routinely employed for the production of transgenic non-human embryos. ES cells are pluripotent cells isolated from the inner cell mass of mammalian blastocyst. ES cells can be cultured in vitro under appropriate culture conditions in an undifferentiated state and retain the ability to resume normal in vivo development as a result of being combined with blastocyst and introduced into the uterus of a pseudo-pregnant foster mother. Those of skill in the art will recognize that various stem cells are known in the art, for example AB-1, HM-1, D3. CC1.2, E-14T62a, RW4 or JI (Teratomacarcinoma and Embryonic Stem Cells: A Practical Approach, E. J. Roberston, ed., IRL Press).

It is to be understood that the WIP knockout mammals described herein can be produced by methods other than the ES cell method described above, for example by the pro-nuclear injection of recombinant genes into the pronuclei of one-cell embryos or other gene targeting methods which do not rely on the use of a transfected ES cell, and that the exemplification of the single method outlined above is not intended to limit the scope of the invention to animals produced solely by this protocol.

The transgenic WIP knockout mammals described herein can also be bred (for example, inbred, outbred or crossbred) with appropriate mates to produce colonies of animals whose genomes comprise at least one non-functional allele of the endogenous gene which naturally encodes and expresses functional WIP. Examples of such breeding strategies include but are not limited to: crossing of heterozygous knockout animals to produce homozygous animals; outbreeding of founder animals (for example, heterozygous or homozygous knockouts), or with a mouse whose inbred genetic background has altered TCR or BCR activation and/or signal transduction, for example, a TCR transgenic mouse.

In an alternative embodiment of the instant invention, transgenic ES cells can be engineered to comprise a genome which comprises disruptions of more than one gene whose polypeptide product has been implicated in WIP signaling.

The WIP knockout mammals, cell lines, primary tissue or cell cultures, cellular extracts or cell organelles isolated from the WIP knockout mammals of the instant invention are useful for a variety of purposes. In one embodiment of the present invention the transgenic WIP knockout mammals produced in accordance with the present invention are utilized as a source of cells for the establishment of cultures or cell lines (for example, primary, or immortalized), which are useful for the elucidation of the roles in WIP in cellular function. Such cells, which can be isolated from mammalian tissues, include lymphocytes, for example T cells or B cells.

The primary cell cultures, or cell lines, can be derived from any desired tissue or cell-type which normally express high levels of WIP mRNA, including but not limited to lymphocytes.

For example, it is desirable to produce panels of cell lines which differ in their expression of one of more genes. Thus, the present invention encompasses a cell line in which an endogenous WIP gene has been disrupted (for example, WIP knockout cells or cell lines such as a B cell or a T cell line). The resulting WIP-functionally disrupted cell comprises a genotype which differs from its parental wild-type cell in a defined manner and thereby allows for the elucidation of the effects of WIP-deficiency on TD antigen stimulation, particularly in T cells and/or B cells. In another embodiment, a WIP knockout cell or cell line can be engineered using skills known in the art. For example, cells which do not possess an endogenous WIP gene or which normally do not express WIP can be engineered to do so. For example, an exogenous WIP gene can be introduced into a cell which does not possess an endogenous WIP gene wherein the cell expresses WIP due to the presence of the exogenous WIP gene. Alternatively, exogenous nucleic acid can be spliced into the genome of a cell which does not normally express WIP in order to "turn on" the normally silent WIP gene. The agent can be for example, a nucleic acid molecule, a polypeptide, an organic molecule, an inorganic molecule, a fusion protein etc. silent, endogenous WIP gene. Subsequently the WIP gene in the engineered cells can be disrupted using the methods described herein and known to those of skill in the art for use in the methods and compositions of the present invention.

The availability of WIP knockout cells and mammals (for example, homozygous, heterozygous) facilitate the genetic dissection of WIP-mediated signaling pathways and allow for the identification of WIP specific inhibitors. For example, an agent which alters one or more functions of WIP equally in a knockout cell line and its wild-type parental cell line would be recognized as a non-WIP-specific inhibitor, while an agent which inhibits a WIP-dependent function in a wild-type cell line which has no effect in the knockout cell line would be recognized as a WIP-specific inhibitor. Further, the use of cell lines which have disruptions in more than one WIP signaling genes have been disrupted could facilitate the identification of agents with potential therapeutic value for the treatment of diseases in which altered WIP function plays a role.

Other embodiments of the invention provide in vitro and in vivo methods of identifying an agent that inhibits the activity (function) of mammalian WIP (for example, an antagonist, a partial antagonist). An inhibitor of WIP includes any agent that inhibits WIP gene expression (partial or complete) or function (partial or complete) of the WIP protein. According to the instant invention, the agent can be combined with a cell (for example, lymphocytes), a primary tissue, and/or administered to a whole animal. As demonstrated in the following examples, administration can be accomplished in various ways such as the addition to culture media, tissue perfusion, by expressing it from a vector, or by injection.

In one embodiment, a suitable in vitro screening method comprises combining cells which comprise a wild type WIP gene (wild-type cells), with an amount of TD antigen sufficient to stimulate TCR ligation and the agent; and combining cells which lack a functional WIP gene (WIP knockout cells), with an amount of TD antigen sufficient to stimulate TCR ligation and the agent. The cells are maintained under appropriate conditions. The phenotype of the wild type cells (i.e. a TCR ligation-induced response) is compared to the phenotype of the WIP knockout cells, wherein if the phenotype of the wild type cells in the presence of the agent is about the same when compared to the phenotype of the knockout cells, then the agent inhibits WIP.

The in vitro screening method can further comprise the use of any suitable control. For example, in one embodiment, the in vitro screening method can further comprise combining the wild type cells with an amount of TD antigen sufficient to stimulate TCR ligation in the absence of the agent; and combining WIP knockout cells with an amount of TD antigen sufficient to stimulate TCR ligation in the absence of the agent. The cells are maintained under appropriate conditions. The phenotype of the wild type cells in the presence of the agent is compared to the phenotype of the wild type cells in the absence of the agent; and the phenotype of the WIP knockout cells in the presence of the agent is compared to the phenotype of the WIP knockout cells in the absence of the agent. If the phenotype of the WIP knockout cells in the presence of the agent is similar to the phenotype of the knockout cells in the absence of the agent, then the agent inhibits Wip. According to the instant invention, an appropriate cell-based assay (for example, lymphocytes such as T cells or B cells) for the identification of agents which inhibit WIP-mediated regulation of TCR ligation-induced responses can be practiced with cells characterized by a disruption of the WIP gene selected from the group consisting of: a homozygous disruption and a heterozygous disruption.

Another embodiment of the present invention provides an in vivo screening method for determining whether an agent inhibits WIP. In one embodiment, a suitable in vivo screening method comprises administering to a non-human mammal which comprise a wild type WIP gene (wild-type mammal), an amount of TD antigen sufficient to stimulate TCR ligation and the agent; and administering to a transgenic non-human mammal which lacks a functional WIP gene (WIP knockout mammal), an amount of TD antigen sufficient to stimulate TCR ligation and the agent. The phenotype of the mammals is measured. The phenotype of the wild type mammal compared to the phenotype of the WIP knockout mammal, wherein if the phenotype of the wild type mammal is the about same when compared to the phenotype of the knockout mammal, then the agent inhibits WIP.

The in vivo screening method can further comprise the use of any suitable control. For example, in one embodiment, the in vivo screening method can further comprise administering to a wild type non-human mammal an amount of TD antigen sufficient to stimulate TCR ligation in the absence of the agent; and administering to a WIP knockout non-human mammal an amount of TD antigen sufficient to TCR ligation in the absence of the agent. The phenotype of the mammals is measured. The phenotype of the wild type mammal in the presence of the agent is compared to the phenotype of the wild type mammal in the absence of the agent; and the phenotype of the WIP knockout mammal in the presence of the agent is compared to the phenotype of the WIP knockout mammal in the absence of the agent. If the phenotype the WIP knockout mammal in the presence of the agent is similar to the phenotype of the knockout mammal in the absence of the agent, then the agent inhibits WIP.

An alternative embodiment of the invention provides a method of identifying a WIP mimic, or an agent that exhibits WIP activity (for example, a recombinant peptide, polypeptide, fusion protein or small molecule). According to this embodiment of the invention the transgenic WIP knockout mammals or their isolated cells, tissues, cellular extracts or organelles provide a starting material, or control material, in which the function of potential WIP mimics can be evaluated. Also encompassed by the present invention is an method of identifying an agent which mimics WIP activity. In one embodiment, the method comprises introducing the agent into cells which lack a functional WIP gene and determining whether a WIP-mediated cellular function (one or more) occurs in the presence of the agent. If WIP-mediated cellular function occurs in the cells which lack a functional WIP gene in the presence of the agent, then the agent is a WIP mimic.

In another embodiment, the method of identifying an agent which mimics WIP activity comprises introducing the agent into a transgenic non-human mammal which lacks a functional WIP gene and determining whether a WIP-mediated cellular function (one or more) occurs in the presence of the agent. If WIP-mediated cellular function occurs in the transgenic non-human mammal which lacks a functional WIP gene in the presence of the agent, then the agent is a WIP mimic.

In the method of identifying a WIP mimic, a WIP-mediated cellular function includes, for example, determining the phenotype of the cells, such as, proliferation, F-actin formation, and/or TD antigen-dependent lymphocyte responses, compared to that of the WIP knockout cell or mammal.

In the methods of identifying agents as described herein, the phenotype of cells and non-human mammals described herein can be determined using a variety of methods as will be recognized by one of skill in the art. For example, and without limitation, immunofluorescence staining of cells, western blotting, videomicroscopy, ELISA, and FACS analysis. In proliferation assays, for example, the use of thymidine incorporation, BrdU uptake, and cell counting are suitable techniques; F-actin formation can be assayed using immunofluorescence staining of cells, electron microscopy (EM) techniques, western blotting and the like; cell protrusions and immunological synapse formation can be assessed by time-lapse videomicroscopy and/or immunofluorescence techniques, as will be appreciated by one of skill in the art.

One of skill in the art will know of appropriate techniques for the introduction and/or expression of potential mimics. For example, a library of nucleotide sequences (for example, cDNA sequences) encoding potential mimics could be introduced (for example, transfected or transduced in the context of an expression vector) and expressed into an appropriate host cell isolated from the knockout non-human mammals provided herein, or into a host cell which has been produced via homologous recombination using a WIP targeting vector according to the instant invention, and screened for the restoration of a WIP-dependent cellular function. For example a potential WIP mimic includes recombinant nucleic acid sequences which encode a truncated WIP polypeptide in combination with a nucleic acid comprising coding sequence derived from another protein (for example a fusion protein), for example nucleic acid sequence which encodes a domain of another WIP-related protein, or nucleic acid sequence which provides for example an inducible promoter sequence or which introduces a cis-acting regulatory sequence. Thus, potential mimics can include portions of a recombinant or naturally occurring WIP polypeptide derived from the same mammalian species or from a different mammalian species.

The present invention also relates to methods of treatment or prevention of conditions or diseases (for example, lymphoma (such as a B cell lymphoma or a T cell lymphoma), leukemia, (such as a T cell leukemia or a B cell leukemia) or AIDS) associated with aberrant WIP function (for example, aberrant TD antigen-induced responses). For example the invention provides a method of treating (for example, alleviating the symptoms of) or preventing (for example, in a individual who is predisposed to develop) a condition or disease associated with aberrant WIP expression. In one embodiment the invention provides a method of increasing WIP function in an individual comprising administering to the individual an agent which exhibits WIP activity, or is a WIP mimic. In a second embodiment the invention provides a method of decreasing WIP function in an individual comprising administering to the individual an agent which inhibits WIP activity.

The agent for use in the methods of the present invention can be for example, a nucleic acid molecule (for example, DNA, RNA, anti-sense DNA, anti-sense RNA), a protein, a peptide, a polypeptide, a glycoprotein, a polysaccharide, an organic molecule, an inorganic molecule, a fusion protein etc.

The agents (for example, therapeutic agents such as WIP inhibitors or WIP mimics) can be administered to a host in a variety of ways. Potential routes of administration include intradermal, transdermal (for example, utilizing slow release polymers), intramuscular, intraperitoneal, intravenous, inhalation, subcutaneous or oral routes. Any convenient route of administration can be used, for example, infusion or bolus injection, or absorption through epithelial or mucocutaneous linings. The agent can be administered in combination with other components such as pharmaceutically acceptable excipients, carriers, vehicles or diluents.

In the treatment methods designed to inhibit the function of WIP, an "effective amount" of the agent is administered to an individual. As used herein the term "effective amount" an amount that inhibits (or reduces) the activity of WIP, and results in a significant (for example, a statistically significant) difference (for example, increase, decrease) in a cellular function which is normally subject to regulation (for example, negative regulation) by WIP. The amount of agent required to inhibit WIP activity will vary depending on a variety of factors including the size, age, body weight, general health, sex and diet of the host as well as the time of administration, and the duration or stage of the particular condition or disease which is being treated. Effective dose ranges can be extrapolated from dose-response curves derived in vitro or an in vivo test system which utilizes the transgenic non-human WIP mammals described herein.

The present invention is illustrated by the following examples, which are not intended to be limiting in any way.

EXAMPLES

The materials and methods described below were used in Examples 1–6, which follow.

Molecular Cloning of WIP Using Yeast Two Hybrid System

Full length WASP cDNA, obtained by reverse transcription polymerase chain reaction (RT-PCR) from peripheral blood T cells, sequence verified, cloned into the bait vector pGBT9 (Clontech, Palo Alto, Calif.) was used to screen a cDNA library constructed from the human lymphoma T cell line KT3 in the activation domain vector pGAD424 (Wright, D. A., Futcher, B., Ghosh, P. & Geha, R. S. (1996) *J. Biol. Chem.*, 271: 31037–31043). Double transformants were selected on Leu$^-$, Trp$^-$, His$^-$ plates containing 20 mM aminotriazole to suppress non-specific background.

Rapid Amplification of cDNA Ends (RACE)

The 5' end of WIP cDNA was obtained by RACE. Two nested antisense primers corresponding to nucleotides 487–510 (5'-GCGGCATTCGGTTCCTCTGAGGCT (SEQ ID NO: 15), WIP-out) and 452–476 (5'-ACTTCTGTGGCCTGGAGAAGGCACA (SEQ ID NO: 16), WIP-in) of the WIP cDNA were constructed and used to PCR a RACE ready library from human peripheral blood mononuclear cells (PBMC) (Marathon library, Clontech, Palo Alto, Calif.) along with the anchor primers supplied by the vendor and LA Taq enzyme (Panvera, Milwaukee, Wis.). The PCR parameters were as follows: denaturation at 94° C. for 30 seconds, annealing at 65° C. for 1 minute, and extension at 68° C. for 4 minutes. Five independent clones derived from three independent PCR reactions were sequenced to verify the sequence of WIP cDNA. Sequence analysis was performed using the GCG version 8.1 package (Genetics Computer Group). The BLAST and the FASTA programs were used to search the GenBank databases at the National Center for Biotechnology Information (NCBI).

Northern Blot Analysis of WIP mRNA Expression

Human multiple tissue Northern blots were purchased from Clontech (Palo Alto, Calif.). After overnight hybridization with radiolabeled full length WIP cDNA, the blots were washed with 0.5× SSC containing 0.1% SDS at 65° C. for 1 hour with two changes of buffer, dried and autoradiographed.

Multiple tissue Northern blots containing 2 mg of human mRNA per lane were hybridized with $^{32}$P labeled full length WIP cDNA probe. The filter was exposed for 12 hr. As a control for loading, the blot was reprobed for GAPDH transcript.

Glutathione S-transferase (GST) and Maltose Binding Protein (MBP) Fusion Proteins To obtain the GST-WASP$_{1-270}$ construct, cDNA coding for amino acids (aa) 1–270 of WASP was amplified by PCR using Pfu polymerase (Stratagene, San Diego, Calif.) and oligonucleotides with EcoRI (5' end) or Sal I (3' end) recognition sequence and cloned into EcoRI-Sal I digested pGEX4T1 (Pharmacia, Piscataway, N.J.). MBP fusion construct of WIP 4 (MBP-WIP4) was made by ligating WIP4 (a clone of WIP obtained by two hybrid screen, see results) cDNA excised from pGAD424 by digestion with EcoRI and Bgl II to EcoRI-Bam HI digested pMAL-c2 expression vector (New England Biolabs, Beverly, Mass.). GST-WIP2 construct was made by ligating WIP2 cDNA excised from the yeast vector pGAD424 by EcoRI-Bgl II digestion to EcoRI-Bam HI digested pGEX4T1. All expression constructs were verified by DNA sequence analysis, and transformed into E. coli BL21 for the expression of the fusion proteins.

WASP$_{1-270}$, WIP4 and the control protein M were expressed in E. coli as fusion proteins with GST or MBP. Soluble extracts from induced bacteria were mixed and the fusion proteins were affinity precipitated using GSH beads, or amylose resin, run on 4–15% gradient SDS-PAGE and examined for the presence of MBP fusion proteins by Western blotting with rabbit anti-MBP antiserum. The blots were developed using protein A conjugated to horseradish peroxidase followed by ECL. The molecular weight of MBP-WIP and of the control MBP-M proteins were similar. The lower molecular bands represented degradation products of the fusion proteins. The presence of GST-WASP$_{1-270}$ and of GST was confirmed by Western blotting with anti-GST mAb.

Expression of fusion proteins was induced as follows: GST-WASP$_{1-270}$ expression was induced for 2 hours with 0.075 mM isopropyl-thio-β-D-galactopyranoside (IPTG). After induction, the bacterial cells were collected by centrifugation, suspended in GST-lysis buffer (20 mM Tris pH 8.0, 150 mM NaCl, 1 mM EDTA, 1 mM DTT, 0.5% NonidetP-40, protease inhibitor mixture (Complete, Boehringer Mannheim, Indianapolis, Ind.) and 0.1% lysozyme) and lysed by sonication (3×15 second). The lysate was clarified by centrifugation at 10,000×g for 5 minutes at 4° C. GST expression was induced by addition of 0.1 mM IPTG and the cells were processed as above.

MBP-WIP4 was induced with 0.3 mM IPTG for 16 hours at 30° C. MBP-M was induced with 0.3 mM IPTG for 2 hours at 37° C. Bacteria were collected by centrifugation and suspended in 1/20 growth volume in E. coli lysis buffer (20 mM Tris, pH 7.4, 200 mM NaCl, 1 mM EDTA with protease inhibitors) and frozen at −20° C. for 2 hours. The suspensions were thawed, sonicated (3×15 sec), and centrifuged for 20 minutes at 10,000×g and 4° C. The supernatants were used in affinity precipitation experiments.

Lysates of BJAB cells were incubated with GSH-Sepharose beads coupled to GST-WIP2 or GST. Bound proteins were eluted, run on 10% SDS-PAGE and examined for the presence of WASP by immunoblotting with rabbit anti-WASP peptide antibody. The blots were developed as described above.

Expression of FLAG-WIP4 protein in clone I was demonstrated by the presence of a specific band corresponding to FLAG-WIP4 in immunoblots of anti-FLAG immunoprecipitates developed with anti-FLAG mAB followed by peroxidase labeled goat anti-mouse Ig and ECL. This band was absent in the control clone A.11 transfected with pcDNA3 alone. The heavy (H) and light (L) chains of the immunoprecipitating mAb were visualized. Full length FLAG-WIP did not transfer in immunoblotting. Expression of FLAG-WIP protein in clone 3 transfected with FLAG-WIP was inferred by the presence of a specific band corresponding to WASP in immunoblots of anti-FLAG immunoprecipitate developed with rabbit anti-WASP followed by protein A and ECL. This band was absent in the control clone A.11.

In Vitro Binding Assay Using GST and MBP Fusion Proteins

Supernatant of bacterial cell lysates containing GST or GST-WASP$_{1-270}$ fusion protein was mixed with supernatant of bacterial cell lysates containing MBP-WIP4 or MBP-M for 20 minutes at 4° C. One half of the mixture was tumbled with glutathione (GSH)-beads and the other with amylose resin at 4° C. for 40 minutes. The beads were washed thrice with tris-buffered saline containing 0.5% Tween 20, and the beads were suspended in 1× Laemmli PAGE buffer and subjected to Western blot analysis.

Generation of WIP Expressing BJAB Cells

WIP and WIP4 cDNAs were cloned into modified pcDNA3 vector that expresses cloned cDNA as a N-terminal FLAG fusion protein (gift of Dr. V. Ramesh, Massachusetts General Hospital, Boston, Mass.). Twenty μg of plasmid were used to transfect 30×10$^6$ BJAB cells by electroporation (1600 μF, 200 V) and cells were selected in medium containing 1.5 mg/ml G418 (GIBCO-BRL, Rockville, Md.). The surviving cells were cloned by plating at 0.3 cells/well in a 96 well plate. The clones were checked for WIP4 expression by Western blotting with anti-FLAG. Because fall length WIP-FLAG did not transfer for immunoblotting, expression of WIP-FLAG was ascertained by PCR and by the presence of WASP in anti-FLAG immunoprecipitates.

Affinity Precipitation of WASP and Profilin from Cell Lysates by WIP

BJAB cells were washed twice with serum free RPMI 1640 medium and suspended on ice for 30 minutes in lysis buffer (50 mM Tris pH 7.4, 150 mM NaCl, 1 mM EDTA, 30% glycerol, 0.4 mM sodium orthovanadate, 10 mM NaF, 10 mM sodium pyrophosphate, protease inhibitor cocktail and 1% Brij 96, Sigma, St. Louis, Mo.) at 40×10$^6$ cells/ml. Lysates were centrifuged at 16,000×g for 15 min. at 4° C. and pre-cleared for 1 hour with 25 µl of GST-Sepharose (Pharmacia). Supernatants were tumbled for 16 hours with ~1 µg of GST-WIP2 immobilized on GSH beads. The beads were washed 3 times with modified lysis buffer containing 10% glycerol and 0.2% Brij 96 (wash buffer), suspended in Laemmli loading buffer and subjected to PAGE on 10% (WASP) or 4–15% (profilin) gradient gels and Western blotting. The blots were developed with rabbit anti-WASP peptide antiserum and protein A-horseradish peroxidase (HRP) or with anti-profilin rabbit antibody.

Immunoprecipitation of FLAG-WIP from BJAB Cells.

FLAG-tagged full length WIP cDNA was transfected into BJAB cells and the cell lysates were immunoprecipitated with M2 anti-FLAG mAb, blotted and probed with anti-WASP peptide antibody.

BJAB cells transfected with WIP or with pcDNA3 vector were washed twice with serum free RPMI 1640 medium and lysed (40×10$^6$ cells/ml) in ice-cold lysis buffer (10 mM Tris pH 7.4, 150 mM NaCl, 1 mM EDTA, 1% Triton X-100, 1% sodium deoxycholate, 0.1% SDS, 1 mM sodium orthovanadate, 50 mM NaF, and 1 mM phenylmethylsulfonylfluoride). The lysates were incubated at 4° C. overnight with 7 µg of anti-FLAG M2 antibody (Kodak-IBI) pre-adsorbed onto 40 µl of protein G Sepharose (Pharmacia, Piscataway, N.J.). The precipitates were washed 4× with wash buffer, eluted in Laemmli loading buffer and subjected to SDS-PAGE on 4–15% gradient gels and Western blot analysis with anti-FLAG mAb or anti-WASP antiserum.

Determination of Polymerized Actin Content

F-actin content was estimated by flow cytometry using fluorescein isothiocyanate (FITC)-phalloidin (Hartwig, J. H., Bokoch, G. M., Carpenter, C. L., Janmey, P. A., Taylor, L. A., Toker, A. & Stossel, T. P. (1995) *Cell*, 82: 643–653). The fluorescence of FITC-phalloidin in this assay is proportional to the amount of F-actin. Cells were fixed with 2% paraformaldehyde, permeabilized with 0.1% Triton X-100 and labeled with FITC-phalloidin for 30 min. at room temperature. The samples were immediately read in a Becton-Dickinson Excalibur flow cytometer. The samples were gated for live lymphocytes according to forward and side scatter profiles.

Untransfected cells (control), a pcDNA3 transfected clone (A.11) and representative clones expressing WIP (clone 3) and WIP4 (clone I) were permeabilized, stained with rhodamine-conjugated phalloidin and examined by immunofluorescence microscopy.

Immunofluorescence Microscopy

Cells were fixed with 3.7% paraformaldehyde in PBS at room temperature for 30 minutes, washed twice with PBS and permeabilized with 0.1% Triton X-100 in PBS at room temperature for 20 minutes. The cells were incubated with 2 µM tetramethylrhodamine B isothiocyanate (TRITC) conjugated phalloidin (Sigma, St. Louis, Mo.) for 1 hour at 37° C. The cells were washed twice with PBS, examined and photographed in a fluorescent microscope (Olympus).

Example 1

Molecular Cloning of WIP

The yeast two hybrid system was used to search for novel WASP interacting protein(s). A cDNA library from the human lymphoma T cell line KT3 was constructed in the activation domain vector pGAD424 (17 Wright, D. A., Futcher, B., Ghosh, P. & Geha, R. S. (1996) *J. Biol. Chem.*, 271: 31037–31043) and was screened in the yeast two-hybrid system using full length WASP cDNA. Six clones that grew on Leu$^-$ Trp$^-$ His$^-$ plates also tested positive for β-galactosidase with blue color developing in less than 30 minutes. The two largest cDNAs, designated WIP2 (1.7 kb) and WIP4 (1.6 kb), were chosen for further detailed characterization. DNA sequence analysis revealed that WIP2 and WIP4 cDNAs are products of the same gene because the WIP4 protein coding sequence was completely contained within WIP2 (FIG. 1C). The 3'-untranslated region of WIP4 was 0.5 kb larger than that of WIP2. Genebank database search revealed that WIP is virtually identical to Prp12, a partial human cDNA isolated from tonsillar B cells whose function is unknown (accession number X86019). The last seven amino acids (aa) of the predicted Prp12 protein are replaced in WIP by seventeen aa of a different sequence (FIG. 1C). In addition, there is a deletion of one aa (aa 270 of the Prp12 sequence). Both of these differences are unlikely to be cloning artifacts since they are found in both WIP2 and WIP4 which were isolated during independent screenings. The 5' end of the WIP mRNA was obtained by RACE, using a peripheral blood leukocyte cDNA library. FIG. 1D shows the deduced aa sequence of WIP. The predicted protein product is a 503 aa long proline-rich protein with a calculated molecular weight of ~52 kD. The N-terminal region contains two stretches, 28 and 17 aa residues in length, that are highly homologous to corresponding aa stretches in the N-terminal region of the yeast protein verprolin (FIG. 1E). Verprolin is involved in cytoskeletal organization because vrp1$^-$ conditional mutants fail to grow at the restrictive temperature of 37° C., have abnormal actin formation and chitin deposition and are defective in bud formation (19 Donnelly, S. F. H., Pocklington, M. J., Pallotta, D. & Orr, E. (1993) *Mol. Microbiol*, 10: 585–596). Of note is the presence of the KLKK (SEQ ID NO: 4) motif in the first WIP verprolin homology domain. This motif was originally identified in thymosin-β4 as a motif which is critical for actin binding (van Troys, M., Dewitte, D., Goethas, M., Carlier, M. F., Vanderkerckhove, J. & Ampe, C. (1996) *EMBO J.*, 15: 201–210.21). Identical, or similar (KLRK (SEQ ID NO: 17), KLRR (SEQ ID NO: 18)), motifs are present in the putative actin binding protein members of the Ena/VASP family (Gertler, F. B., Niebuhr, K., Reinhard, M., Wehland, J. & Soriano, P. (1996) *Cell*, 87: 227–239), raising the possibility that WIP may interact directly with actin. In addition, WIP contains two APPPPP (SEQ ID NO: 19) sequences (denoted by asterisk in FIG. 1D) which have been shown to bind profilin (Purich, D. L. and Southwick, F. S. (1997) *Biochem. Biophys. Res. Comm.*, 231:686–691), a protein that regulates actin polymerization.

WIP contains a number of putative SH3 binding motifs with the sequence PPPψXP (SEQ ID NO:20). A unique proline rich motif, GRSGPXPPXP (SEQ ID NO: 7) is repeated three times in WIP (FIG. 1F). This motif recurs twice in WASP and has been implicated in the binding of WASP to the SH3 domain containing proteins fyn, fgr and phospholipase Cγ1 (Finan, P. M., Soames, C. J., Wilson, L., Nelson, D. L., Stewart, D. M., Truong, O., Hsuan, J. J. & Kellie, S. (1996) *J. Biol. Chem.*, 271: 26291–26295). The presence of conserved SH3 binding motifs in WIP suggests that WIP may link the signal transduction machinery to the cytoskeleton.

Example 2

WIP Associates with WASP Both in Vitro and in Vivo

The association of WASP and WIP was confirmed by several experiments. First, the interaction of WASP and WIP expressed as recombinant bacterial fusion proteins with glutathione S transferase (GST) and maltose binding protein (MBP), respectively, was examined. GSH-Sepharose retained MBP-WIP following incubation with a mixture of MBP-WIP and GST-WASP, indicating binding of WIP to WASP and suggesting that posttranslational modification of these proteins is not necessary for their interaction. Endogenous WASP from the human B cell line BJAB was also shown to bind to purified recombinant GST-WIP2. More importantly, WIP and WASP were shown to associate in cells. A protein band corresponding to WASP was detected in anti-FLAG immunoprecipitates from BJAB cells transfected with full length FLAG-WIP cDNA, but not in anti-FLAG immunoprecipitates from cells transfected with empty vector. WASP was not detected in control MOPC21 (mouse IgG1) immunoprecipitates from FLAG-WIP transfected BJAB cells.

Figure 2B:
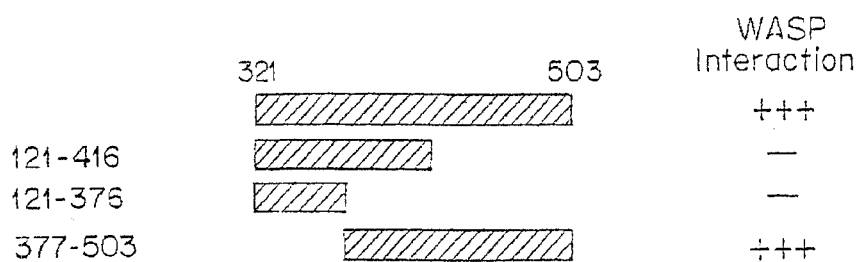
FIG. 2B is a map of the WASP binding site of WIP. Truncation mutants of WIP4 (aa 321–503), generated by cleavage with appropriate restriction enzymes were cloned into the pGAD424 vector and examined for WASP binding in the yeast two hybrid system. Interactions were scored as indicated above in FIG. 2A.

WASP binds to activated Cdc42 at a conserved GBD domain (aa 238–257) (Aspenstrom, P., Lindberg, U. & Hall, A. (1996) Curr. Biol., 6: 70–75; Kolluri, R., Tolias, K. F., Carpenter, C. L., Rosen, F. S. & Kirchhausen, T. (1996) Proc. Natl. Acad. Sci. (USA), 93: 5615–5618; Symons, M., Derry, J. M. J., Kariak, B., Jiang, S., Lemahieu, V., McCormick, F., Francke, U. & Abo, A. (1996) Cell, 84: 723–734). To map the WIP binding site, truncations of WASP were examined for WIP binding in the yeast two hybrid system. The results show that the WIP binding region lies within the N-terminal 170 aa of WASP (FIG. 2A). Since this region lacks the GBD domain (aa 238–257), the WIP binding site on WASP is distinct from the Cdc42 binding site. Neither the WASP 1–137 truncation mutant which contains the WH1 domain nor the proline-rich aa 139–270 region were able to bind WIP. Thus, both of these regions are necessary, but not sufficient, for WIP binding. Deletion of the N terminal 46 aa, which disrupts the pleckstrin homology (pH) domain, but not the WH1 domain, sharply reduced the affinity of WASP for WIP suggesting that aa 1–46 are required for optimal binding to WIP. Curiously, the majority of point mutations in patients with WAS are located in the WH1 domain, although this domain makes up only 18% of the WASP sequence (Schwarz, K., Nonoyama, S., Peitsch, M., de Saint Basile, G., Espanol, T., Fasth, A., Fischer, A., Freitag, K., Friedrich, W., Fugmann, S., Hossle, H.-P., Jones, A., Kinon, C., Meindl, A., Notaranagelo, L., Weschler, A., Weiss, M. & Ochs, H. (1996) Immunol. Today, 17: 496–502). Mutations in the WH1 domain could potentially disrupt the association of WASP with WIP, raising the possibility that interaction of WASP with WIP may be critical for WASP function. The carboxy terminal 183 aa of WIP, i.e., WIP4 (aa 321–503), are sufficient for WASP binding. To further localize the binding site of WASP on WIP, truncation mutants of WIP4 were constructed and examined for binding to WASP in the yeast two hybrid system (FIG. 2B). The results show that the WASP binding region lies within aa 377–503 of WIP. Further analysis showed that the WASP binding region lies within amino acid residues 415 to 488.

Example 3

Assessment of Expression of WIP

The expression of WIP transcripts in human tissues was analyzed by Northern blot analysis of poly A$^+$ RNA from a panel of tissues using full length WIP cDNA as probe. Results showed that WIP is expressed in hematopoietic and non-hematopoietic tissues. Three species of mRNA with estimated sizes of 2.4 kb, 3.5 kb and 5 kb are present in all tissues tested. The different RNA species could represent a family of proteins or differently spliced/polyadenylated mRNA. Since the RNA bands are evident even when washed at relatively stringent conditions (0.5×SSC, 0.5% SDS), it suggests that the different bands are probably splice variants. The level of expression of the WIP transcripts is highest in PBMC, in which the 2.4 kb species is expressed at a higher level than the other two species. Expression of WIP in non-hematopoietic tissues, which do not express WASP, suggests that WIP may have other interaction partners than WASP.

Example 4

Expression of WIP Causes Actin Polymerization

WIP contains the highly charged KLKK (SEQ ID NO: 4) sequence (aa 45–48) in its N-terminal verprolin homology domain, immediately preceded by a region that could fold as an α-helix. This motif mediates contact between G-actin and thymosin β4 (van Troys, M., Dewitte, D., Goethas, M., Carlier, M. F., Vanderkerckhove, J. & Ampe, C. (1996) EMBO J., 15: 201–210.21). WIP also contains two copies of the actin based motility sequence ABM-2, APPPPP (SEQ ID NO: 19), which has been implicated in binding to profilin in VASP and Mena (Gertler, F. B., Niebuhr, K., Reinhard, M., Wehland, J. & Soriano, P. (1996) Cell, 87: 227–239; Reinhard, M., Giehl, K., Abel, K., Haffner, C., Jarchau, T., Hoppe, V., Jockusch, B. M. & Walter, U. (1995) EMBO J., 14: 1583–1589). One of the two profilin binding motifs in WIP (aa 8–13) is located in relative proximity to the G-actin binding motif as found in the Ena/VASP family of proteins. Simultaneous binding of G-actin and profilin by Ena/VASP is thought to promote actin polymerization (Gertler, F. B., et al., Cell, 87:227–239 (1996)). To examine the role of WIP on actin polymerization, the effect of overexpression of WIP on F-actin content was examined in B lymphocytes. FLAG-tagged full length WIP and FLAG-tagged WIP4 (aa 321–503) were cloned into pcDNA3 and transfected into BJAB cells. Transfected cells were selected using the antibiotic G418 and cloned. To ascertain the expression of FLAG-WIP proteins, cell lysates were immunoblotted with anti-FLAG mAb M2. The FLAG-WIP4 product was readily detectable in cell lysates and in immunoprecipitates with anti-FLAG M2 mAb. Despite multiple attempts using a number of immunoblotting conditions, the full length FLAG-WIP product could not be immunoblotted, possibly because of its very high proline content. However, for the representative clone 3, the presence of WASP was demonstrated in anti-FLAG immunoprecipitates from FLAG-WIP transfected cells, providing evidence for expression of tagged WIP protein that interacted with WASP. Expression of FLAG-WIP mRNA was also ascertained in several clones by RT-PCR.

F-actin content was assessed by staining permeabilized cells with FITC-conjugated phalloidin followed by flow cytometry analysis. Table 1 shows that there was an increase in baseline F-actin content in BJAB cell clones that overexpressed full length WIP, but not in control transfected cells. The effect of WIP overexpression on F-actin content was dependent on the N-terminal region of WIP. Overexpression of WIP4 which lacks the first 320 aa and thus lacks the actin binding KLKK (SEQ ID NO: 4) motif and one of two profilin binding ABM-2 sequences did not cause an increase in F-actin content.

TABLE 1

Effect of Overexpression of WIP on F-Actin Content in BJAB cells

| Transfection | Cells | Relative F-actin content |
| --- | --- | --- |
| Untransfected | BJAB | 1.0 |
| pcDNA3 | Clone A.11 | 0.96 ± 0.25 |
| FLAG-WIP | Clone 2 | 1.40 ± 0.25 |
|  | Clone 3 | 1.79 ± 0.11 |
|  | Clone 4 | 1.55 ± 0.01 |
| FLAG-WIP4 | Clone I | 1.10 ± 0.17 |

F-actin content was determined by measuring mean fluorescence intensity in permeabilized cells stained with FITC-phalloidin. The F-actin content represents the mean ratio of the F-actin content in transfected cells to that in untransfected BJAB cell in 4 experiments. t tests revealed that FLAG-WIP clones 2, 3 and 4 were significantly higher $p \leq 0.001$). There was no significant difference between Clone A.11 and Clone I ($p=0.20$).

It was previously shown that overexpression of WASP causes the formation of cytosolic aggregates containing F-actin and WASP (Symons, M., Derry, J. M. J., Kariak, B., Jiang, S., Lemahieu, V., McCormick, F., Francke, U. & Abo, A. (1996) Cell, 84: 723–734). The effect of WIP overexpression on F-actin distribution was assessed by immunofluorescence microscopy of permeabilized BJAB cells stained with TRITC-phalloidin. Results showed that F-actin is uniformly distributed around the cortex in untransfected cells (control) and in cells transfected with pcDNA3. In contrast, in clone 3, which overexpresses full length FLAG-tagged WIP, the cell surface was covered with cerebriform projections containing actin. The cerebriform nature of the projections is reflected in the lacy staining pattern. Formation of surface projections and the increase in F-actin content were dependent on the N-terminal region of WIP, because F-actin staining in clones which overexpress WIP4 was indistinguishable from that of control cells.

Example 5

GST-WIP Affinity Precipitates Endogenous Profilin

In light of the capacity of WIP to increase F-actin content, the critical role of profilin in actin polymerization (Pantaloni, D. & Carlier, M.-F. (1993) Cell, 75: 1007–1014; Theriot, J. A. & Mitchison, T. J. (1993) Cell, 75: 835–838), and the presence of profilin binding motifs in WIP, the capacity of WIP to bind profilin was examined. Profilin was readily detected in lysates of BJAB cells by immunoblotting with rabbit anti-profilin antibody. GST-WIP2, but not GST, retained endogenous profilin following incubation with BJAB cell lysate.

Example 6

WIP Binds to Adaptor Protein Nck

Yeast Two-hybrid System

Full-length Nck cDNA was cloned in-frame into the bait vector pGBT9 (CLONTECH). The sequence of the clone was confirmed by DNA sequence analysis, and the clone was designated Nck-GBT9.

WIP4 is a truncation of WIP cDNA that encodes the carboxyl-terminal portion of WIP (amino acids 321–503) (Ramesh, N. A., et al., Proc. Natl. Acad. Sci. USA, 94:14671–14676 (1997)). WIP4 cDNA cloned in the yeast two-hybrid vector pGAD was used to construct the WIP4 deletion mutants. Deletions were obtained by digestion with the appropriate restriction enzymes followed by Klenow treatment and religation. pGAD-WIP-(321–415) was obtained by digestion with StuI and PstI, and pGAD-WIP-(321–376) was obtained by digestion with SfiI and PstI, and pGAD-(377–503) was obtained by SfiI digestion, Klenow treatment, EcoRI digestion, and a second Klenow treatment. WIP inserts for pGAD-WIP-(415–503) and pGAD-WIP-(416–488) constructs were obtained by polymerase chain reaction. All constructs were confirmed by sequencing.

Yeast transformation and colony analysis were performed according to the manufacturer's instructions (Matchmaker Two-Hybrid System Protocol, CLONTECH).

GST Fusion Proteins

Glutathione S-transferase (GST) fusion proteins of Nck and of each of its three SH3 domains were generated as described previously (Lu, W. et al., Curr. Biol., 7:85–93 (1997)). All expression constructs were verified by DNA sequence analysis. Expression of fusion proteins in transformed Escherichia coli l was induced for 2 h with 0.1 mM isopropyl-thio-β-D-galactopyranoside. Fusion proteins were purified as described previously (Ramesh, N. A., et al., Proc. Natl. Acad. Sci. USA, 94:14671–14676 (1997)).

Generation of WIP Expressing BJAB Cells

WIP4 cDNA was cloned into a modified pcDNA3 vector that expressed cloned cDNA as an amino-terminal FLAG fusion protein and was transfected into the human B lymphoma cell line BJAB as described (Ramesh, N. A., et al., Proc. Natl. Acad. Sci. USA, 94:14671–14676 (1997)). The culture medium for BJAB-transfected cells was supplemented with 1.5 mg/ml G418 (Calbiochem).

Affinity Precipitation of WIP by GST Fusion Proteins

Lysates of BJAB cells transfected with pcDNA3 or with pcDNA-WIP4 were obtained as described previously (Ramesh, N. A., et al., Proc. Natl. Acad. Sci. USA, 94:14671–14676 (1997)) and precleared for 1 h with 25 µl of GST-Sepharose (Amersham Pharmacia Biotech). Supernatants were tumbled for 16 h with 2 µg of GST or GST fusion proteins immobilized on GSH beads. The beads were washed, suspended in Laemmli loading buffer and subjected to PAGE on 4–15% gradient gels and Western blotting. The blots were developed with rabbit anti-WIP followed by protein A conjugated to horseradish peroxidase or with anti-FLAG M2 mAb followed by goat anti-mouse conjugated to horseradish peroxidase and enhanced chemiluminescent detection (ECL).

Immunoprecipitation of FLA G-WIP from BJAB Cells

BJAB cells or BJAB cells transfected with pcDNA-WIP were washed twice with phosphate-buffered saline and lysed ($46 \times 10^6$ cells in 0.35 ml) in ice-cold lysis buffer (50 mM Tris, pH 7.4, containing 150 mM NaCl, 5 mM $MgCl_2$, 30% glycerol, 0.4 mM $Na_3VO_4$, 10 mM NaF, 10 mM $Na_3P_2O_7$, protease inhibitor mixture (Complete, Boehringer Mannheim) and 1% Brij 96) for 30 min. Lysates were centrifuged at 16,000×g for 15 min at 4° C. and precleared for 1 h at 4° C. with 5 µl of normal mouse serum bound to protein G-Sepharose (Amersham Pharmacia Biotech) and then incubated overnight at 4° C. with 8 µg of anti-FLAG M2 monoclonal antibody (mAb) or of isotype-matched control MOPC21 mAb preadsorbed onto 40 µl of protein G-Sepharose. The precipitates were washed 4× with modified lysis buffer containing 10% glycerol and 0.2% Brij-95, eluted in Laemmli loading buffer, and subjected to SDS-PAGE on 4–15% gradient gels and Western blot analysis with anti-FLAG mAb or anti-Nck mAb (Transduction Laboratories). The blots were developed by ECL as described above.

Results and Discussion of Examples 1–6

Nck Interacts with WIP in the Yeast Two-Hybrid System

WIP contains several proline-rich sequences including three repeats of the sequence GRSGPXPPXP (SEQ ID NO: 7). This sequence is repeated twice in WASP and is involved in the binding of WASP to the SH3.3 domain of Nck (Finan, P. M. et al., *J. Biol. Chem.*, 271:26291–26295 (1996)). Therefore, it is likely that WIP maybe a candidate for binding to Nck. Since all the three GRSGPXPPXP (SEQ ID NO: 7) sequences were present within WIP4, a truncation of WIP that contains amino acids 321–503, the interaction of WIP4 with Nck by the yeast two-hybrid system was tested. Table 2 shows that Nck interacts specifically with WIP4. Nck did not interact with human TRAF1 (tumor necrosis factor receptor-associated factor 1) used as a control, and WIP4 did not with laminin (Table 2). As expected, WIP4 interacted with WASP (Ramesh, N. A., et al., *Proc. Natl. Acad. Sci. USA*, 94:14671–14676 (1997)).

TABLE 2

Interaction of Nck and WIP by the yeast two-hybrid system

| pGBT9 | pGAD424 | | |
|---|---|---|---|
| | None | WIP4 | TRAF1 |
| None | ND | — | — |
| Nck | — | ++ | — |
| WASP | — | +++ | — |
| Laminin | — | — | ND |

Two-hybrid assay results for HF7c clones containing the Gal 4 binding (pGBT9) or activation (pGAD424) domain vectors with the indicated fusion protein insert are shown. WIP4 represents amino acids 321–503 of WIP. TRAF1 represents amino acids 62–416 of human TRAF1. A—indicates no growth on Leu/Trp/His negative SD synthetic medium in the presence of 20 mM S-aminotriazole. A ++ denotes growth both on the selective medium and β-galactosidase activity with color development in 2 h, and +++ indicates growth on the selective medium and color change in 30 min. ND, not done.

Endogenous Nck Co-immunoprecipitates with WIP from BJAB Cells

To demonstrate the Nck-WIP associated in vivo, whether Nck and WIP co-immunoprecipitate from cells was examined. To this purpose, the presence of Nck in anti-FLAG immunoprecipitates of lysates from human B cells BJAB transfected with FLAG-tagged WIP4 cloned in pcDNA3 was examined.

Nck was present in anti-FLAG immunoprecipitates from FLAG-WIP4 transfected cells. Nck was not detected in MOPC21 mAb immunoprecipitates of WIP4-transfected cells nor in M2 immunoprecipitates of untransfected BJAB cells. To ascertain the presence of FLAG-tagged WIP in the immunoprecipitates, the membrane was stripped and reblotted with anti-FLAG M2 mAb. FLAG-tagged WIP4 is detected in M2 immunoprecipitates from BJAB cells transfected with FLAG-WIP4 and, as expected, in total lysates from FLAG-WIP4-transfected cells. FLAG-WIP4 was neither detected in MOPC21 immunoprecipitates from WIP4-transfected cells nor in M2 immunoprecipitates from untransfected cells.

Treatment of cells with phorbol 12-myristate 13-acetate for 15, 30, or 60 minutes did not alter the capacity of Nck and WIP to co-immunoprecipitate suggesting that Nck phosphorylation induced by phorbol 12-myristate 13-acetate (Park, D. and Rhee, B. G., *Mol. Cell. Biol.*, 12:5816–5823 (1992)) does not regulate WIP-Nck interaction.

WIP Binds to the Second SH3 Domain of Nck

To confirm Nck interaction with full-length WIP, GST-Nck fusion protein was used to affinity precipitate endogenous WIP from BJAB cells. The precipitates were run on SDS-PAGE and Western-blotted with anti-WIP rabbit antibody. WIP was present in GST-Nck precipitates but not in control GST precipitates.

Since proteins that bind to Nck have a preference for one of its three SH3 domains, which of the three SH3 domains of Nck preferentially interacts with WIP was determined. GST fusion proteins of Nck and of each of its individual SH3 domains were used to affinity precipitate WIP from BJAB cells transfected with FLAG-tagged WIP4 or with empty pcDNA3 vector, and the precipitates were run on SDS-PAGE and Western-blotted with anti-FLAG M2 antibody. WIP bound to the SH3.2 domain of Nck but not to the SH3.1 and SH3.3 domains of Nck. No bands were detected in precipitates of lysates from BJAB cells transfected with empty vector. With longer exposures, WIP binding to SH3.1 and SH3.3 domains of Nck but not to GST was detected. As a control for fusion protein loading, the gels were stained with Coomassie Blue. The small differences in the amounts of fusion protein used (<2-fold) are unlikely to account for the difference in the ability of the Nck SH3 domains to bind WIP.

Two copies of the sequence GRSGPXPPXP (SEQ ID NO: 7) which has been implicated in the binding of WASP to SH3.3 of Nck are present in the shortest truncation of WIP that binds Nck (WIP-(321–415)). Yet WIP bound poorly to SH3.3 of Nck. This suggests that residues other than those in the above sequence determine binding to individual SH3 domains of Nck. The SH3.3 domain of Nck mediates its binding to the serine/threonine kinase CKI-γ2 (Lussier, G. and Larose, L., *J. Biol. Chem.*, 372:2688–2694 (1997)).

Mapping of the Nck-binding Site of WIP

As discussed above, WASP binds to the carboxyl-terminal region of WIP, amino acids 377–503 (Ramesh, N. A., et al., *Proc. Natl. Acad. Sci. USA*, 94:14671–14676 (1997)). To determine whether the WASP- and Nck-binding sites on WIP overlap, the interaction of WIP deletion mutants with WASP and Nck was examined using the yeast two-hybrid system. WIP-(416–488) bound to WASP but not to Nck. In contrast, the WIP deletion mutated WIP-(321–415) binds to Nck but not to WASP. Taken together, these results show that the WASP and Nck binding domains of WIP differ.

Since WIP and WASP bind preferentially to distinct SH3 domains of Nck, Nck may simultaneously engage WIP and WASP, thereby increasing the local concentration of both proteins and enhancing their interaction. Since different domains of Nck bind to WIP and WASP, different sites on WASP bind to WIP and Nck, and different sites on WIP bind to Nck and WASP; it is likely that trimolecular complexes of Nck, WIP, and WASP exist in which each of the proteins could contact the two others.

WIP May Bridge Nck to Profilin and the Cytoskeleton

WIP interacts with profilin (Ramesh, N. A., et al., *Proc. Natl. Acad. Sci. USA*, 94:14671–14676 (1997)). The two profilin binding consensus sequences in WIP (APPPPP) (SEQ ID NO: 19) are located at positions 8–13 and 427–432 and are outside the Nck-binding (amino acids 321–415). This raised the possibility that WIP may couple Nck to profilin. Whether profilin co-precipitates with Nck was examined. Endogenous profilin from lysates of BJAB cells was bound to GST-Nck but not to GST. Nck lacks proline-rich sequences, including profilin binding consensus sequences (A, G, L or S followed by PPPPP) (SID NO: 21) (Purich, D. L. and Southwick, F. B., *Biochem. Biophys. Res.*

Commun., 231:686–691 (1997)) and fails to interact with profilin in the yeast two-hybrid system. These results suggests that the binding of profilin to Nck is indirect and is likely mediated by WIP.

The Drosophila homolog of Nck, Dock, has been shown to be involved in the photorecptor cell (R cell) axon guidance, suggesting that it plays a role in cytoskeletal reorganization (Garrity, P. A. et al., Cell, 85:639–650 (1996)). In addition to binding profilin, WIP contains the actin-binding KLKK sequence, and its overexpression increases the cell content of F-actin. Furthermore, via its interaction with WASP (Ramesh, N. A., et al., Proc. Natl. Acad. Sci. USA, 94:14671–14676 (1997)) and N-WASP, WIP may modulate cytoskeletal reorganization. Therefore, it is likely that WIP links Nck to the actin cytoskeleton. Since Nck is recruited to RTKs following their tyrosine phosphorylation subsequent to ligand binding, the Nck-WIP interaction provides an important link between extracellular signaling via RTKs and reorganization of the cytoskeleton.

The materials and methods described below were used in Example 7, which follow.

Generation of WIP-deficient Mice (Transgenic WIP Knockout Mice)

DNA encoding the murine wip gene was isolated by hybridizing a BAC library made from the 129/SvJ mouse strain (Genome Systems, Inc.) with a fragment of mouse WIP cDNA. High-resolution restriction mapping yielded the genomic map of the wip gene. The targeting construct was assembled in the pLNTK targeting vector using a 4.5 kb EcoRI/XbaI blunted fragment and a 3.5 kb EcoRI/SacI blunted fragment. The construct (20 $\mu$g) was transfected by electroporation into ES cells (TC-1), which were then selected in medium containing 0.4 mg/ml of G418 and 10 $\mu$g/ml of gancyclovir. One of 97 clones found to contain both a normal and a disrupted allele and no random integration of the neo gene was injected into 3.5 day old C57BL/6 blastocysts, and WIP$^{-/-}$ mice were obtained by standard methods (Tsitsikov et al. (1997) Proc. Nat. Acad. Sci. USA 94: 10844–10849).

Antibodies and Flow Cytometry Analysis

Mabs mouse antigens were purchased from PharMingen and used for FACS as previously described in Hollander et al., (1996) Proc. Nat. Acad. Sci. USA 93: 4994–4998).

Serum Ig Levels and Antibody Responses to Antigen

Serum Ig levels were determined by ELISA (Tsitsikov et al. (1997) Proc. Nat. Acad. Sci. USA 94: 10844–10849). The antibody response to KLH, TNP- and TNP-Ficoll was examined as previously described (Tsitsikov et al. (1997) Proc. Nat. Acad. Sci. USA 94: 10844–10849).

Proliferation of B and T Cells and Interleukin-2 Assay

Purified spleen B cells (>80% B220$^+$ cells) were cultured at 1×10$^5$/well in medium alone or in the presence of various stimuli and 48 hr later were pulsed with 1 $\mu$Ci [$^3$H]-thymidine and counted.

Purified T cells (>95% CD3$^+$ cells) were cultured at 1×10$^5$/well for 64 hrs in wells coated with 10 (g/ml anti-CD3 mAb (KT3, Serotec) with or without 10 (g/ml anti-CD28 mAb (37.51, BD Pharmingen). Recombinant murine IL-2 (R&D Systems) was used at 40 ng/ml. PMA was used at 15 ng/ml and ionomycin at 0.5 $\mu$M. Proliferation was assessed by the incorporation of [$^3$H]-thymidine. IL-2 in supernatants was measured by quantifying the proliferation of the IL-2-dependent cell line CTLL-2 (American Type Culture Collection) and by ELISA.

MAPK Kinase Assay

T cell activation was performed as previously described (Sun, Z., et al., (2000) Nature 404:402–407). Cell lysates were probed sequentially with anti-phospho-Erk, anti-Erk (both from SantaCruz Biotechnology), anti-phospho-SAPK/JNK, and anti-SAPK/JNK antibodies (Cell Signaling).

Determination of Cellular F-actin

Purified T cells (4×10$^6$ cells/ml) were incubated with rat anti-mouse CD3 mAb (KT3, 10 $\mu$g/ml) for 30 min. on ice followed by cross-linking with goat anti-rat Ig (20 $\mu$g/ml) for 5 min at 37 C., microspun, then fixed in 4% formalin, washed and then permeabilized and stained in a single step with 0.1% Triton X-100 and 5 $\mu$g/ml Phalloidin-TRITC.

Fluorescence Microscopy and Time Lapse Videomicroscopy

Glass coverslips were coated with anti-CD3 mAb (KT3, 20 $\mu$g/ml in PBS) for 1 hr. at 37° C. and blocked with BSA. Purified T cells (1×10$^6$ cells/ml) were allowed to sediment on the coverslips for 30 min at 4° C. After washing off unattached cells, warm medium at 37° C. was added and cell movements were followed for 20 min on an IM-35 Zeiss microscope with a warm-stage. Images were acquired with an Orca-II cooled CCD camera driven by Metamorph software. Frames were taken every 5 sec. After 20 min. the cells were fixed and stained for F-actin.

Lipid Bilayers

Purified lymph node T cells were loaded onto bilayers containing biotinylated 0.2% biotin-caproyl-phosphatidylethanolamine, egg lecithin and Cy5 conjugated GpI-linked ICAM-1 (Pharmacia), ICAM-1 alone (control) or lecithin alone (control) in a flow cell chamber. Avidin-FITC (10(g/ml) was added and the bilayers washed as described (Grakoui, A., et al., (1999) Science 285:221–227). Biotinylated anti-CD3 epsilon (145-2C11, BD Biosciences, 10 (g/ml) was added and the bilayers washed. Cells at 37° C. were added to the chamber at various time points, were fixed with 4% paraformaldehyde and stained with CtxB-cy5 (Cholera Toxin B, Molecular Probes), then with rhodamine phalloidin (10%, Molecular Probes). There were no interactions on the lecithin bilayer. Cells were imaged using a Zeiss LSM 510 confocal on an Axiovert 200 microscope. Analysis was performed using Zeiss LSM software. Backgrounds were subtracted and averages and standard deviations taken. Two-tailed t-test was used to determine statistical significance between WIP KO and WT counterparts in the same experiment.

T cell-A20 B Lymphoma Interactions

Purified splenic T cells were labeled at 4° C. with Fab fragments of Cy5-labeled anti-TCR H57 mAb and Cy3-labeled anti-LFA-1 H155 mAb, then loaded at 37° C. 3:1 onto A20 B lymphoma cells expressing I-E$^k$GFP (gift of M. Davis, Stanford University), and incubated at 37° C. with medium or SEA superantigen (1 $\mu$M, Sigma). The cells were gently pelleted (200 rpm, 2 min), fixed with 4% paraformaldehyde and imaged using a Zeiss LSM 510 confocal on an Axiovert 200 microscope. Analysis was performed using IP Lab. Statistical significance was determined using averages and standard deviations and 2-tailed T-Test.

Electron Microscopy

WIP$^{+/-}$ and WIP$^{-/-}$ T and B lymphocytes were allowed to adhere respectively to anti-CD3 coated and anti-IgM coated 5 mm glass coverslips. Coverslips were then warmed to 37° C. for 0 or 15 min, then mechanically unroofed by attaching and removing a polylysine-coated coverslip to the apical cell surface after placing the cells in PHEM buffer (60 mM Pipes, 25 mM Hepes, 10 mM MgCl$_2$, and 10 mM EGTA) containing 1 $\mu$M phallacidin and protease inhibitors. Unroofed cells were washed once in PHEM buffer and fixed with 1% glutaraldehyde in PHEM buffer for 10 min. The coverslips were washed into distilled water and cytoskeletons on the surface frozen by slamming them into a liquid helium-cooled copper block. Some coverslips were fixed without unroofing in 1% glutaraldehyde in PBS. All specimens were freeze-dried in a Cressington CFE-50 apparatus (Cressington, Watford, England) at −90° C. and rotary coated with 1.4 nm of platinum and 3.0 nm of carbon without rotation. They were photographed in a JEOL 1200 EX electron microscope using a 100 kV accelerating voltage.

Example 7

WIP Deficiency Reveals a Differential Role for WIP and the Actin Cytoskeleton in T and B Cell Activation Generation of WIP-deficient mice.

Figure 3A:
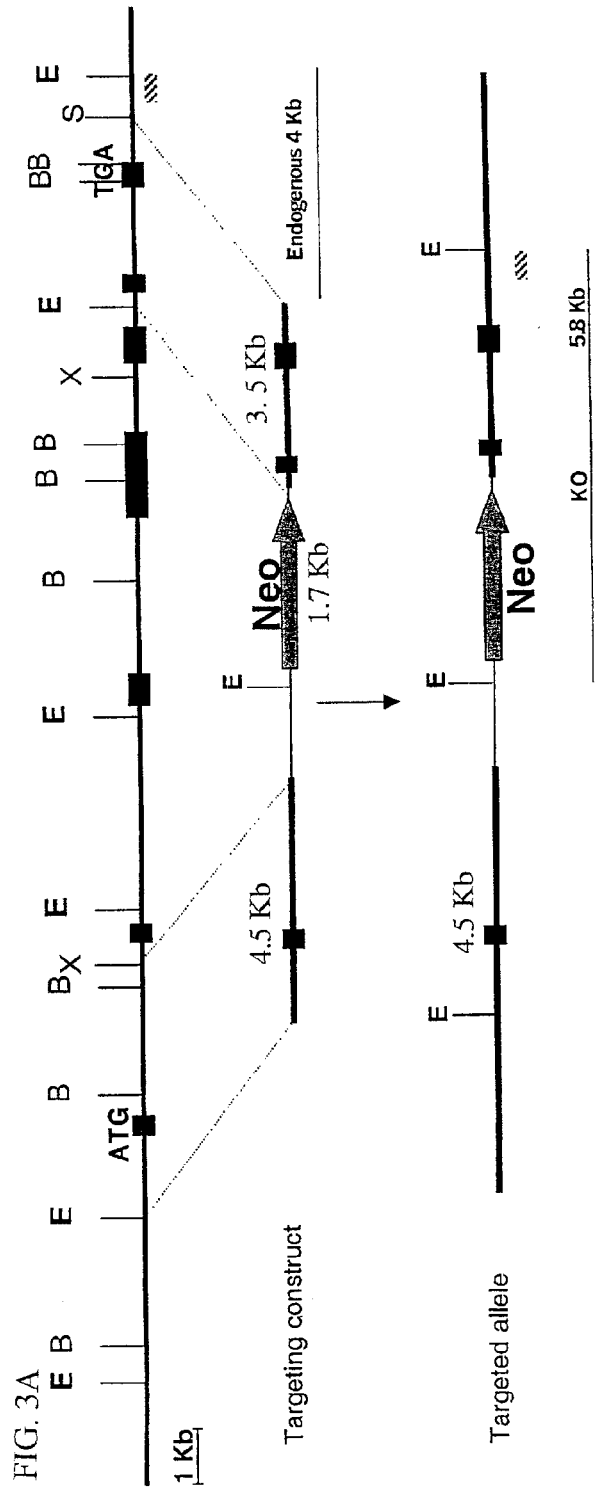
FIGS. 3A–C is an outline of the generation of WIP-deficient mice.
Figure 3C:
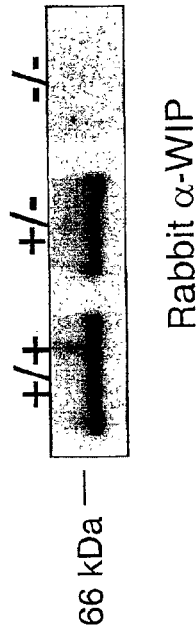
Figure 3B:
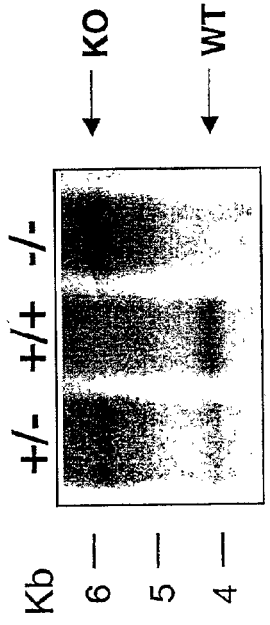

A targeting construct in which coding exons 2 to 5 of the murine wip gene were replaced with a neomycin-resistant gene was introduced in ES cells (FIG. 3A). ES clones with targeted disruption of one wip allele were identified in Southern blots by the presence of a novel 5.8 kb fragment derived from the targeted allele in addition to the 4 kb fragment derived from the WT allele. Of 97 ES clones analyzed, one was found to have a disrupted allele and was used to generate WIP$^{-/-}$ mice, which were identified by Southern blot analysis (FIG. 3B). Western blot analysis of lysates from thymocytes, lymph nodes (L.N.) and splenocytes confirmed the absence of WIP expression in WIP$^{-/-}$ mice (FIG. 3C). WIP$^{-/-}$ mice did not display apparent differences from WT littermates in growth, weight, or health.

Normal lymphoid development in WIP-deficient mice.

Thymus cellularity in WIP$^{-/-}$ mice 6–10 weeks of age was significantly reduced compared to WT littermates ($106\pm66\times10^6$ cells in KO versus $220\pm94\times10^6$ cells in WT, n=6 p=0.03. Detailed FACS analysis of thymocytes at 6–10 weeks of age revealed no obvious differences in the percentages of CD4$^+$ and CD8$^+$ cells, or of CD3, TCRαβ, TCRγδ, and CD2 positive cells. There were no obvious differences between spleen and L.N. from 6–8 week old WIP$^{-/-}$ and WT littermates as to or percentages of CD4$^+$, CD8$^+$, B220$^+$, IgM$^+$, IgD$^+$ and Thy1$^+$ cells. Bone marrow cells from the same WIP$-/-$ mice had a normal profile of staining for B220, IgM and CD43 and the numbers of B220$^+$, CD5$^+$ B1 cells in the peritoneum of WIP$^{-/-}$ mice were normal. These results indicate that WIP is not essential for the development of B and T lymphocytes.

Increased proliferation and IL-2 receptor expression in B Cells from WIP$^{-/-}$ mice in response to stimulation.

Figure 4A:
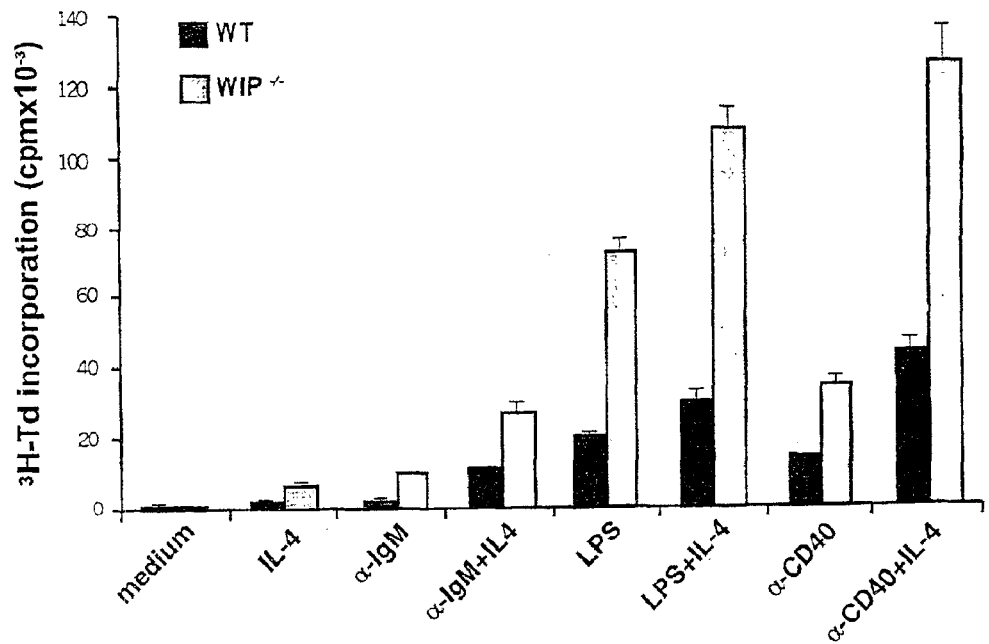
FIGS. 4A–C are the results of three analyses of B cell activation in WIP$^{-/-}$ mice.
Figure 4B:
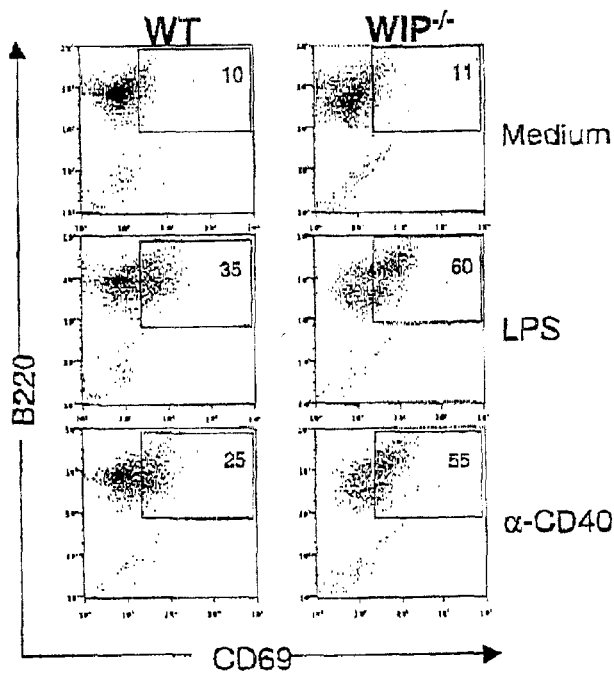

Pure B cells (>80% B220$^+$) from WIP$^{-/-}$ mice showed markedly increased proliferation in response to anti-IgM, lipopolysaccharide (LPS), and anti-CD40 mAb with or without IL-4 (FIG. 4A). Activated B cells express increased levels of CD69. There was increased expression of CD69 (Risso, A., et al., (1989) *Eur. J. Immunol.* 19:323–328) on B cells from WIP$^{-/-}$ mice following stimulation with LPS, anti-CD40, LPS+IL-4 and anti-CD40+IL-4 compared to B cells from WT littermates (FIG. 4B). The enhanced response of WIP$^{-/-}$ B cells to BCR ligation was not simply due to failure of internalization of the BCR which terminates signaling, because they internalized their BCR normally following anti-IgM crosslinking, as assessed by FACS.

Figure 4C:
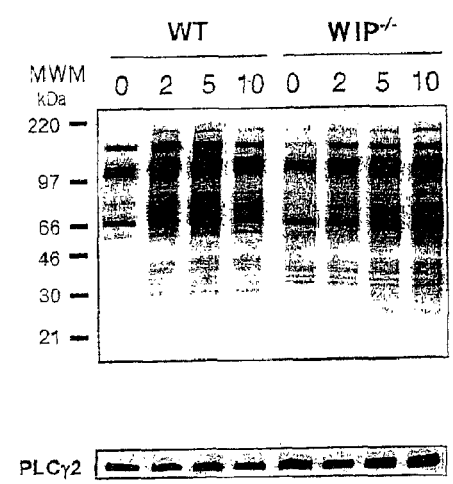

BCR ligation results in tyrosine phosphorylation of several proteins (reviewed in Benschop and Cambier (1999) *Curr. Op. Immunol.* 6: 70–75 and Kurosaki et al., (2000) *Immunol. Rev.* 176: 19–29). Following anti-IgM stimulation, tyrosine phosphorylation of proteins <50 kDa in mol. wt. was enhanced in WIP$^{-/-}$ B cells (FIG. 4C).

Serum immunoglobulins and antibody responses in WIP$^{-/-}$ mice.

Figure 5A:
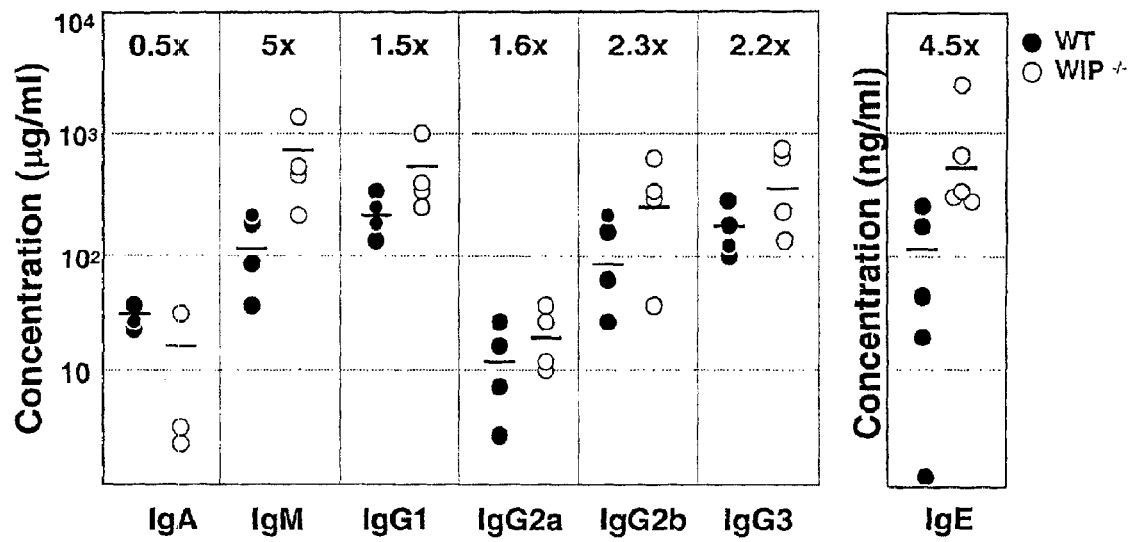
FIGS. 5A–C are the results of tests of antibody production in WIP$^{-/-}$ mice.

Serum IgM and IgE levels were significantly elevated in 6–8-week-old WIP$^{-/-}$ mice compared to WT littermates, while serum IgG subclasses and serum IgA were not significantly different (FIG. 5A).

Figure 5B:
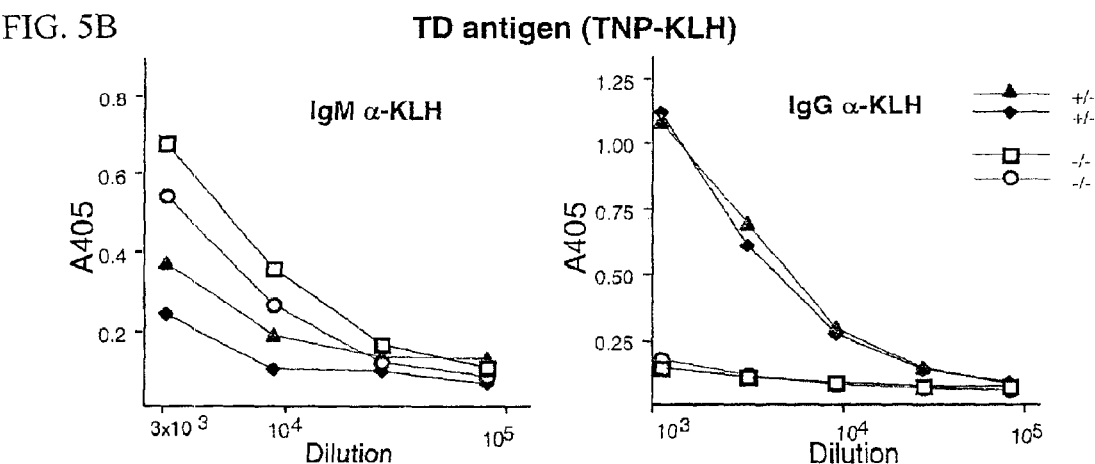
Figure 5C:
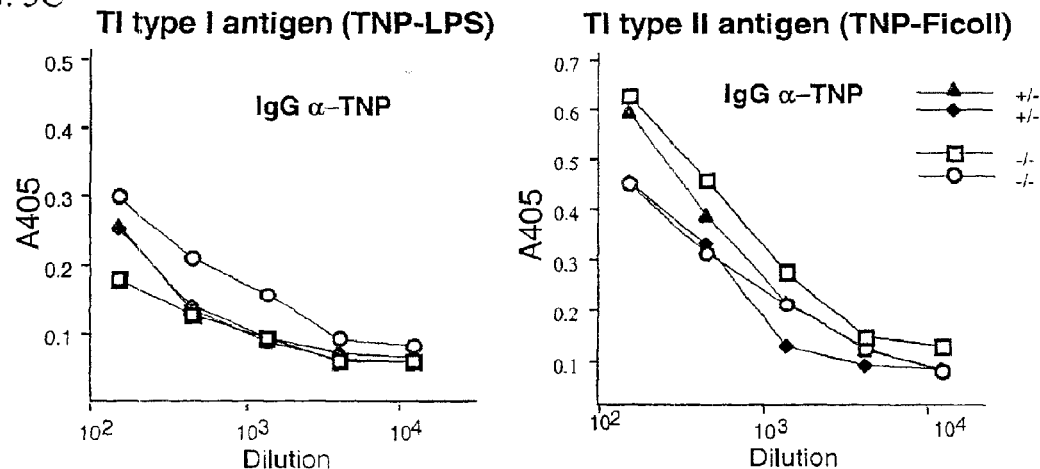

To determine the role of WIP in antibody immune responses, WT, WIP$^{-/-}$ mice and WIP$^{+/-}$ littermates were immunized with the T-dependent (TD) antigen TNP-KLH and T-independent (TI) antigens. WIP$^{+/-}$ mice had serum immunoglobulins and antibody responses indistinguishable from those of WT controls. WIP$^{-/-}$ mice had normal or slightly increased IgM antibody responses, but virtually undetectable IgG responses, to both, KLH (FIG. 5B) and TNP. Both IgG and IgM antibody responses of WIP$^{-/-}$ mice to the type I TI antigen TNP-LPS and to the type II TI antigen TNP-Ficoll were normal (FIG. 5C).

WIP is essential for T Cell activation via the TCR/CD3 complex.

Figure 6A:
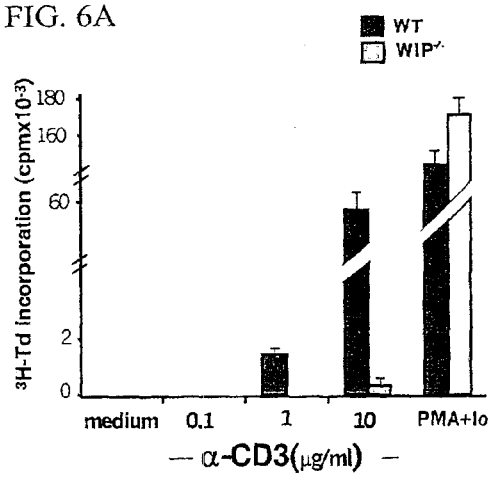
FIGS. 6A–E are the results of antigen receptor-induced proliferation and activation in purified T WIP$^{-/-}$ T cells.

Proliferation in response to plate-bound anti-CD3 was abolished in WIP$^{-/-}$ T lymphocytes at all coating concentrations tested (FIG. 6A). In contrast, proliferation to PMA + ionomycin, which bypass receptor signaling, was normal.

Figure 6B:
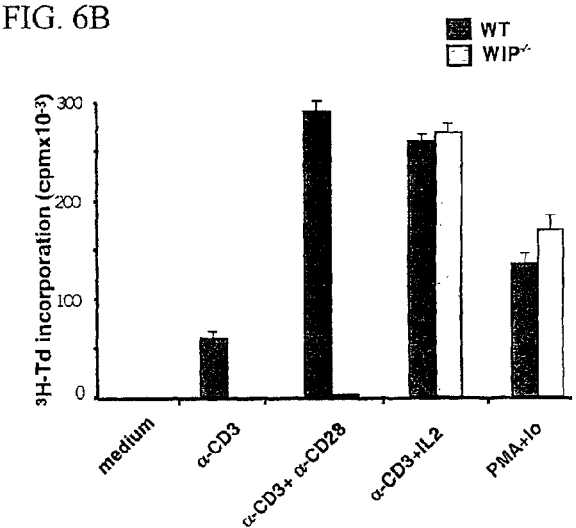
Figure 6C:
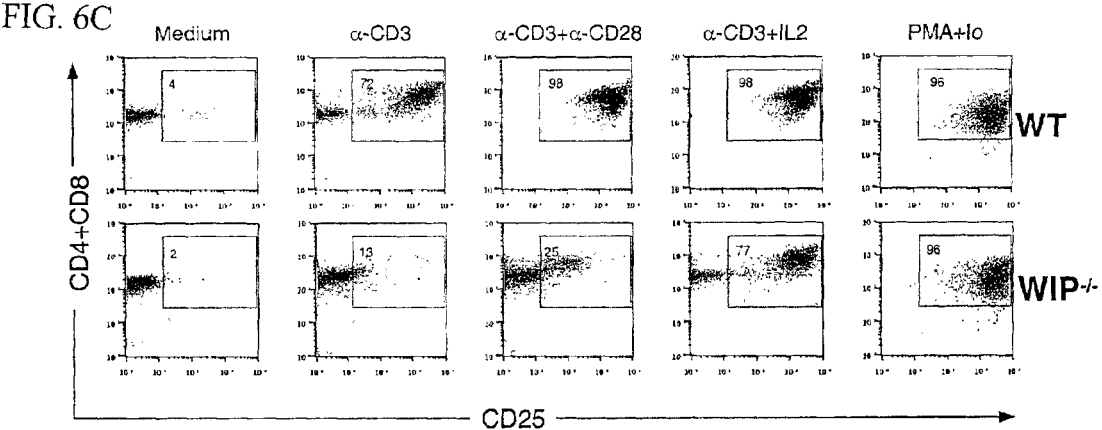
Figure 6D:
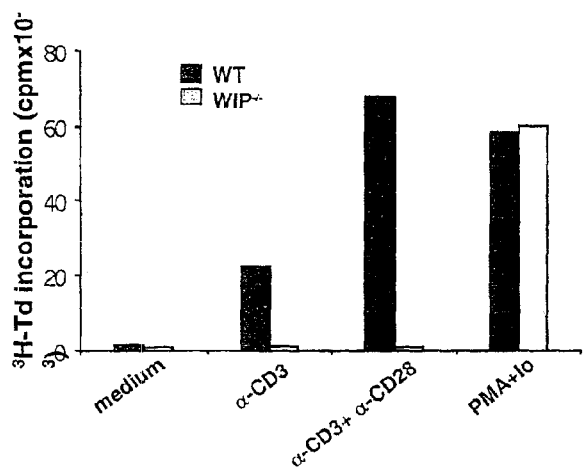

Interactions between IL-2 and IL-2 R play an important role in T cell proliferation and optimal production of IL-2 by T cells requires co-stimulation via CD28 (Rudd, C. E. (1996) *Immunity* 4:527–534). The failure of WIP$^{-/-}$ T cells to proliferate to anti-CD3 was corrected by addition of IL-2, but not by co-stimulation with anti-CD28 mAb (FIG. 6B). WIP$^{-/-}$ T cells poorly up-regulated IL-2Ra chain expression following anti-CD3 stimulation (FIG. 6C). This was only modestly enhanced by co-stimulation with anti-CD28 and almost completely corrected by addition of IL-2. Similar results were obtained for CD69 expression. WIP$^{-/-}$ T cells failed to secrete detectable IL-2 after CD3 ligation, even upon co-stimulation with anti-CD28, as determined by bioassay (FIG. 6D) and ELISA.

Figure 6E:
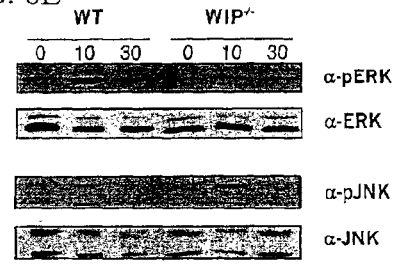

TCR/CD3 ligation causes rapid activation of a number of tyrosine kinases, resulting in tyrosine phosphorylation of several proteins that play important roles in TCR signal transduction (reviewed in Acuto and Cantrell (2000) *Ann. Rev. Immunol.* 18: 165–184). Following anti-CD3 stimulation, protein tyrosine phosphorylation was grossly intact in WIP$^{-/-}$ T cells, and calcium fluxes were only slightly decreased (~15% decrease, n=4 experiments). Erk phosphorylation was also slightly decreased, whereas JNK phosphorylation was normal (FIG. 6E). Furthermore, there was no detectable impairment in the nuclear translocation of NFkB and NFATc as assessed by immunofluoresence.

WIP$^{-/-}$ T Cells Do Not Increase F Actin Content or Form Protrusions and Pseudopodia Following TCR/CD3 Ligation.

Figure 7A:
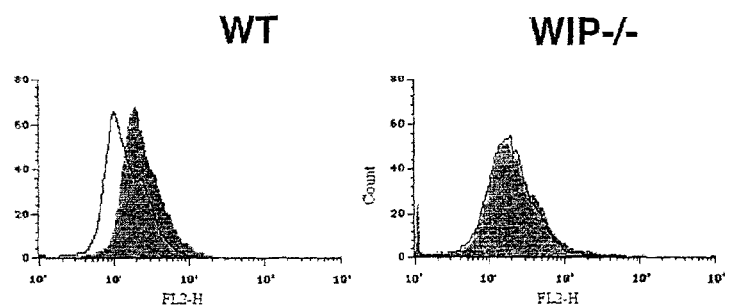
FIGS. 7A–C are the results of analyses of F-actin content and distribution and time lapse videomicroscopy of T cells after stimulation with anti-CD3.

TCR/CD3 ligation causes an increase in the cellular F-actin of normal T cells (Phatak, P. D., and Packman, O. H. (1994) *J. Cell. Physiol.* 159:365–370). The effect of TCR/CD3 ligation on cellular F-actin content was examined by staining permeabilized cells with TRITC-labeled phalloidin. In 4 experiments the amount of F-actin in unstimulated WT and WIP$^{-/-}$ T cells was similar. However, in contrast to T cells from WT littermates, T cells from WIP$^{-/-}$ mice failed to increase their F-actin content following stimulation with anti-CD3 (FIG. 7A).

Figure 7B:
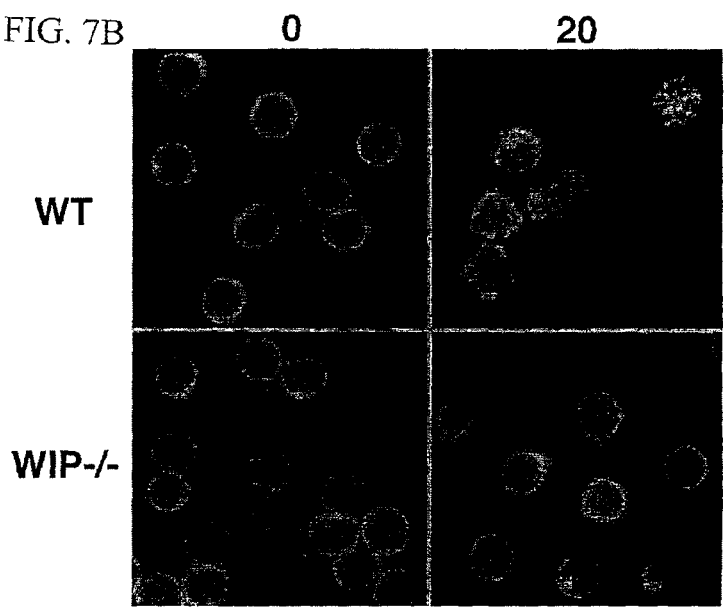
Figure 7C:
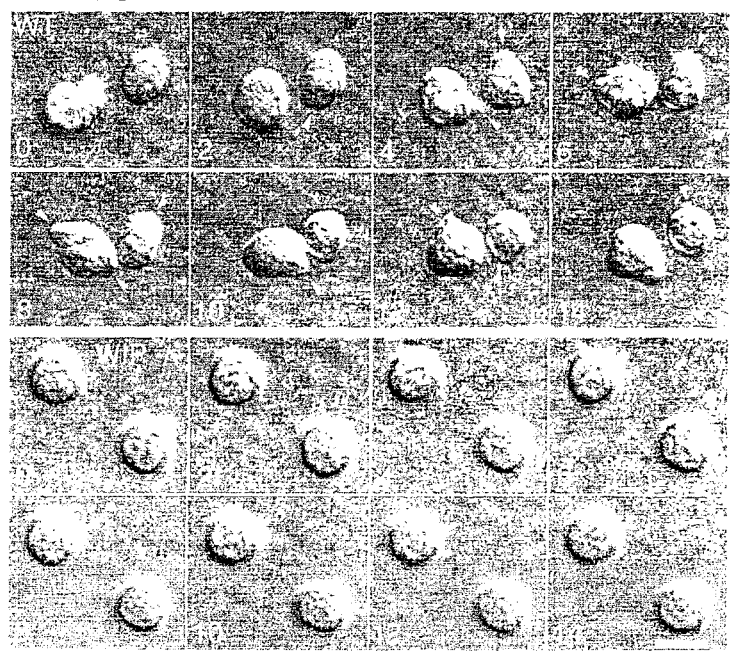

Engagement of the TCR/CD3 complex triggers a distinct pattern of reorganization of cellular F-actin (Bunnell, S. C., et al., (2001) *Immunity* 14:315–329; Parsey, M. V. and Lewis, G. K. (1993) *J. Immunol.* 151:1881–1893). Cytoskeletal reorganization was examined in T cells activated using coverslip-bound anti-CD3 antibody. This system closely mimics T cell activation by MHC class II-peptide complexes arrayed on the surface of APCs by creating a polarized stimulus that induces T cells to undergo the morphological changes necessary to maximize the contact between their antigen receptors and the activating surface (Bunnell, S. C., et al., (2001) *Immunity* 14:315–329). Unstimulated T cells from WT and WIP$^{-/-}$ mice exhibited a similar staining pattern with prominent actin rings, as previously described (Parsey, M. V. and Lewis, G. K. (1993) *J. Immunol.* 151:1881–1893). After incubation for 20 min over anti-CD3 coated glass coverslips, T cells from WT mice acquired a polarized shape, had less prominent actin rings and spread by making microspikes and blunt pseudopodia enriched in F-actin (FIG. 7B and video frames in FIG. 7C). The surface projections were visualized by fluorescence microscopy, although they were difficult to detect by differential interference contrast used in the time lapse videomicroscopy. In contrast, T cells from WIP$^{-/-}$ mice maintained a round shape with persistence of a strong actin ring. More importantly, they spread very poorly on anti-CD3 coated surface and had markedly reduced ability to make cortical protrusions (FIG. 7B and video frames in FIG. 7C). However, actin cap formation following stimulation with immobilized anti-CD3 for 20 min. was similar in WIP$^{-/-}$ T cells and controls (52% versus 54% capped cells).

The failure of T cells from WIP$^{-/-}$ mice to spread and to develop projections following TCR/CD3 ligation prompted examination of their dynamics when exposed to an anti-CD3 coated surface. Purified T cells were plated on anti-CD3 coated or anti-B220 coated glass coverslips and observed with videomicroscopy for 20 minutes. T cells from WT and WIP$^{-/-}$ mice attached to a similar extent to the anti-CD3 coated surface, but did not attach to the anti-B220 coated control surface. The change in shape and polarized appearance of T cells from WT mice after incubation with bound anti-CD3 for the indicated times from 0–14 min. are illustrated in FIG. 7C. During the course of the video, 90% of tracked T cells from WT mice cells extended protrusions that later retracted only to appear again in other areas of the cell. In contrast, T cells from WIP$^{-/-}$ mice did not acquire a polarized shape; only 9% of them exhibited protrusions at some point and the number and the movement of these protrusions were drastically reduced.

Contact formation with anti-CD3 bilayers and conjugate formation with APCs are impaired in WIP$^{-/-}$ T cells.

The poor response of WIP$^{-/-}$ T cells to anti-CD3 could be related to defects in TCR clustering. This hypothesis was tested using a planar bilayer substrate in which fluorescently labeled anti-CD3 mAb is laterally mobile and ICAM-1 provides adhesion. Equivalent clustering of anti-CD3 in contacts of WT and WIP$^{-/-}$ T cells was observed by 4 minutes. By 20 minutes the WT cells displayed extensive contact areas with the planar bilayer and co-localization of F-actin and GM1 in the contact area. Total GM1 in WT and WIP$^{-/-}$ cells was similar in level, but the amount of GM1 in the contact areas was greater in WT cells. The mobility of the WT cells on the surface resulted in dispersion of the clustered anti-CD3, but the total amount of clustered anti-CD3 in WT contacts remained the same when integrated over the large contact areas. After 20 minutes, WIP$^{-/-}$ T cells formed smaller contacts areas with lower levels of F-actin and GM1 than WT cells, but still contained clustered anti-CD3 mAb. The difference in contact area was statistically significant, while the trends in F-actin and GM-1 localization were consistently observed, but were not statistically significant upon quantification.

In summary, WIP$^{-/-}$ T cells cluster the TCR/CD3 complex, but display a significant defect in contact area expansion and fail to form an expanded interface with APC. Wild-type cells and WIP knockout cells tested for TCR clustering using a planar bilayer substrate in which fluorescently labeled anti-CD3 mAb is laterally mobile and ICAM-1 provides adhesion. At 20 minutes WT LN T cells interact with ICAM-1- and anti-CD3 FITC—containing bilayers. The cells were fixed and stained using phalloidin-rhodamine (for F-actin) and CtxB-cy5 (for GM1). The CD3 antibody is laterally mobile in the bilayer so accumulations indicate CD3-Ab interaction. The motility of WT cells results in some shedding of CD3 clusters that appear around the contact areas. Control bilayers lacking anti-CD3 showed no contact formation. At 20 minutes, WIP$^{-/-}$ lymph node T cells also interacted with the same type of bilayer, and were fixed and stained as WT cells. Statistical analysis used students t-test with an n=94. WIP$^{-/-}$ T cells polarize LFA-1, but fail to form an expanded interface with the APC. The contact angle is greater than 90° for WT and less than 90° for the WIP$^{-/-}$.

These results suggested that WIP$^{-/-}$ T cells might have defects in forming an immunological synapse upon interaction with APCs. An I-E$^k$ positive APC and the superantigen Staphylococcal Enterotoxin A (SEA) to were used to trigger the initial stages of synapse formation (Wulfing, C., et al., (1998) *Proc. Natl. Acad. Sci. USA* 95:6302–6307). An early actin-dependent stage in immunological synapse formation has been identified as an extensive interface between the T cell and APC (Negulescu, P. A., et al., (1996) *Immunity* 4:421–430; Wulfing, C., et al., (1998) *Proc. Natl. Acad. Sci. USA* 95:6302–6307). Formation of this broad interface with pseudopod extension is most prominent at 2 min., and is actin dependent. WT cells formed a classical extended interface in which clustering of the integrin LFA-1 was observed. The extension of pseupopodia resulted in a contact angle greater than 90° with the APC in all WT cells conjugates observed. At this time point, TCR redistribution was not detectable, although SEA was required to observe conjugates providing evidence of TCR-SEA-MHC interactions. WIP$^{-/-}$ T cells displayed 2 fold fewer conjugates and a significantly smaller interface both at the 2 min and 5 min time points. The contact angle was also always smaller than 90° indicating that the WIP$^{-/-}$ T cells remained round, a situation that was never observed with WT cells at that time. Despite the overall defect in contact formation, LFA-1 was still accumulated to a similar extent as in the WT T cell conjugates.

Figure 8A:
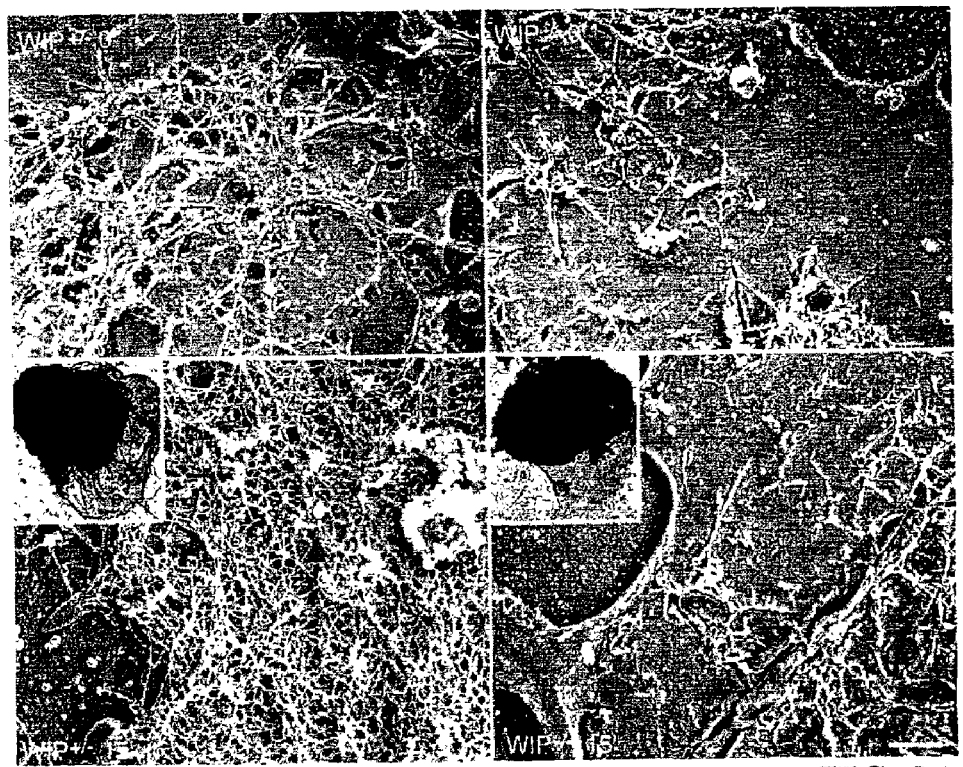
FIG. 8A are electron micrographs of purified T lymphocytes from 8–10-week-old mice adhered at 4° C. to anti-CD3 coated coverslips and then allowed to spread for 0 to 15 min at 37° C. The cells were mechanically unroofed and cytoskeletal-membrane fragments prepared. Also, at the 15 min time point, intact cells were photographed.

The cortical actin network is disrupted in WIP-deficient lymphocytes. WIP stabilizes actin filaments (Ramesh, N., et al. (1997) *Proc. Natl. Acad. Sci. USA* 94:14671–14676). This prompted examination of the architecture of the actin network in WIP$^{-/-}$ lymphocytes. Purified T and B cells were adhered to anti-CD3 and anti-IgM coated coverslips respectively, and their actin network was directly visualized by electron microscopy by unroofing pseudopods to reveal the basal cell membrane. The cytoplasmic surface of the plasma membrane of adherent unstimulated WT T cells was decorated with a loose network of F-actin (FIG. 8A left upper panel). Activation over anti-CD3 coated coverslips for 15 min, led to recruitment of additional F-actin (FIG. 8A left bottom panel) and formation of prominent protrusions (FIG. 8A inset in left bottom panel). In marked contrast, although the total basal F-actin content was similar in WT and WIP$^{-/-}$ T cells (FIG. 7A), the plasma membrane of adherent WIP$^{-/-}$ T cells was sparsely coated with F-actin and activation did little to alter this coating (FIG. 8A, right upper and bottom panels), and resulted in less prominent protrusions than in WIP$^{+/-}$ cells (FIG. 8A inset in right bottom panel). These findings indicate that WIP is essential for the integrity of the actin cytoskeleton in T cells and for its reorganization following TCR engagement.

Figure 8B:
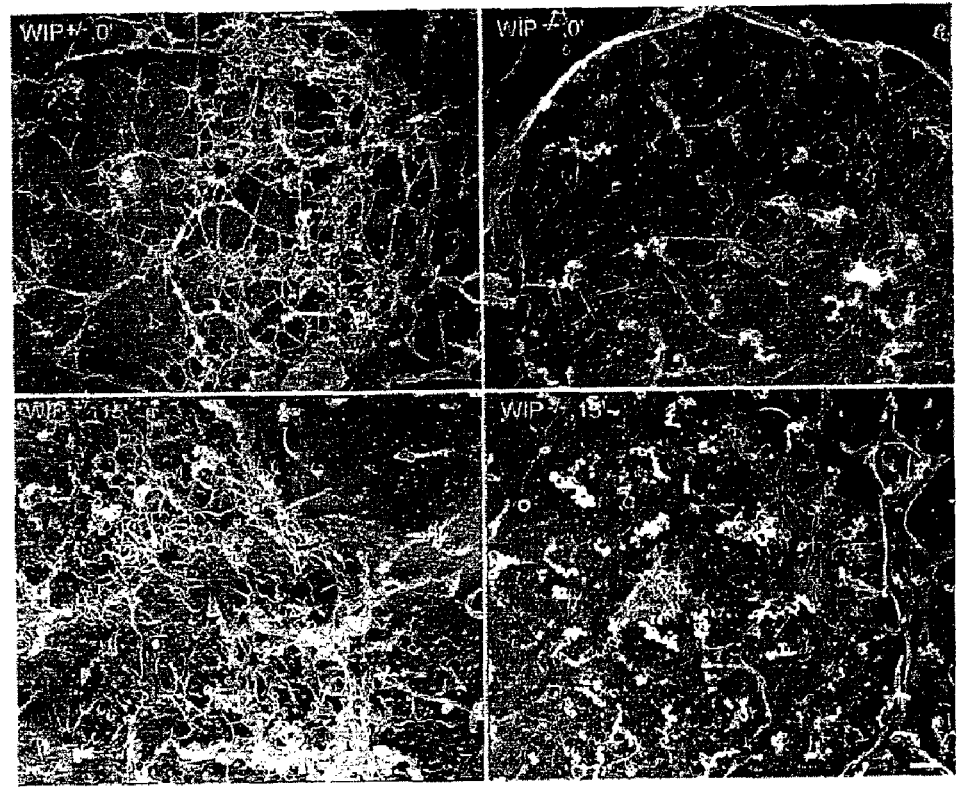
FIG. 8B are electron micrographs of purified B lymphocytes from 17-week-old mice adhered at 4° C. to anti-IgM coated coverslips, allowed to spread for 0 to 15 min at 37° C. and processed as above.

A similar defect in the actin network was also found in WIP-deficient B cells. The cytoplasmic surface of the plasma membrane of B cells from WIP$^{+/-}$ mice was decorated with a loose network of F-actin (FIG. 8B left upper panel) and there was no increase in the density of the actin network following anti-IgM stimulation (FIG. 8B left bottom panel). This was consistent with the observation that anti-IgM stimulation caused a marginal increase in F-actin content of B cells. The plasma membrane of adherent WIP$^{-/-}$ B cells is sparsely coated with F-actin (FIG. 8B right upper panel) and like the others was not changed following anti-IgM stimulation (FIG. 8B right bottom panel). These findings indicate that WIP is also important for the integrity of the actin cytoskeleton in B cells.

Results and Discussion of Example 7

The results indicate that WIP is critical for the integrity of the actin cytoskeleton in both T and B lymphocytes and is essential for T cell, but not necessarily essential for B cell, activation.

Although WIP is widely expressed, WIP$^{-/-}$ mice appear normal and show no gross abnormalities. Moreover, except for a modest reduction in thymocyte numbers in WIP$^{-/-}$ mice, WIP is dispensable for T and B lymphocyte development, but is essential for T cell activation and proliferation in response to ligation of the TCR/CD3 complex. T cells from WIP$^{-/-}$ mice completely failed to proliferate and secrete IL-2 in response to anti-CD3 (FIG. 6). Correction of the proliferation defect and upregulation of CD25 expression by anti-CD3, suggest residual CD3 signaling in WIP$^{-/-}$ T cells. The failure of anti-CD28 co-stimulation to correct the proliferative defect of WIP$^{-/-}$ T cells may reflect a requirement for a higher threshold of signaling via CD3 and/or a requirement for WIP in CD28 signaling. CD28 may be linked to WIP by Vav (Klasen, S., et al., (1998) *Int. Immunol.* 10:481–489), which synergizes with WIP in inducing NFAT activity and IL-2 production (Savoy, D. N., et al., (2000) *J. Immunol.* 164:2866–2670).

Failure of WIP$^{-/-}$ mice to undergo IgG isotype switching in vivo following immunization with the TD antigen TNP-KLH (FIG. 5B) reflects deficient T cell help, rather than an intrinsic abnormality in the B cells, since IgG isotype switching in response to type I and type II TI antigens was normal (FIG. 5C).

WIP was not essential for the early biochemical events that follow TCR engagement since calcium mobilization and total protein tyrosine phosphorylation, JNK phosphorylation and nuclear translocation of NFκB and NFAT were all essentially normal in WIP$^{-/-}$ T cells. However, T cells from WIP$^{-/-}$ mice failed to increase their F-actin content following TCR/CD3 ligation (FIG. 7A). Inhibition of actin polymerization with cytochalasin D blocks both calcium flux and IL-2 secretion induced by cross-linking of the TCR/CD3 complex (Valitutti, S., et al., (1995) *J. Exp. Med.* 181:577–584). Furthermore, TCR ligation induces association of tyrosine-phosphorylated CD3ζ with the actin cytoskeleton. Disruption of this association results in reduced IL-2 production, but preserved tyrosine phosphorylation (Rozdzial, M. M., et al., (1995) *Immunity* 3:623–633). The failure of T cells from WIP$^{-/-}$ mice to secrete IL-2 is consistent with their failure to increase F-actin content. The well preserved calcium flux in these cells could be explained by a less stringent requirement for actin polymerization and by residual actin polymerization activity in WIP$^{-/-}$ T cells, compared to its complete inhibition caused by cytochalasin D.

Activation of Jurkat T cells with immobilized anti-CD3 antibodies provokes a distinctive pattern of F-actin reorganization and characteristic changes in cell shape (Bunnell, S. C., et al., (2001) *Immunity* 14:315–329). This includes progressive dissolution of actin rings followed by cellular spreading and formation of pseudopods (Parsey, M. V. and Lewis, G. K. (1993) *J. Immunol.* 151:1881–1893). As shown herein, similar results were found when WT murine T cells were stimulated with coverslip-bound anti-CD3 antibody: the actin ring attenuates, actin-rich microspikes appear on the cell surface and pseudopodia form and attach to the stimulating surface. In contrast, T cells from WIP$^{-/-}$ mice conserve their actin rings and fail to form protrusions and pseudopodia following anti-CD3 stimulation (FIG. 7B). This indicates an essential role of WIP in cytoskeletal reorganization after TCR engagement.

Upon initial TCR triggering by engagement with peptide-MHC in the APC surface, T cells polarize towards the APC, crawl around them and spread lamellipodia. These changes, which require a functional actin cytoskeleton (Valitutti, S., et al., (1995) *J. Exp. Med.* 181:577–584), allow the sustained association of multiple TCR/peptide-MHC complexes required for triggering optimal T cell activation. WIP$^{-/-}$ T cells fail to acquire a polarized shape and exhibit very few motile protrusions when exposed to an anti-CD3 coated surface (FIG. 7C), indicating that WIP$^{-/-}$ T cells are unable to establish the sustained contact with the APC necessary for antigen driven T cell activation.

Experiments with anti-CD3 on planar bilayers demonstrated that CD3 is engaged and clustered in WIP$^{-/-}$ T cells similarly to WT T cells. Nevertheless, there was a profound defect in expansion of the contact area, which is a hallmark of early immunological synapse formation. Similar results were obtained with T cell-APC interactions triggered by SEA. LFA-1 clustering in the nascent immunological synapse was observed in response to antigen in WIP-deficient T cells, but the interface was not normal in that it never underwent the characteristic expansion observed for WT cells within two minutes of cell-cell contact. The finding that WIP$^{-/-}$ T cells can cluster LFA-1 in the interface indicates that LFA-1 activation may not require formation of new actin filaments and demonstrates that some actin dependent functions, which also include actin cap formation, are intact in WIP$^{-/-}$ mice.

Electron microscopy revealed that the amount of F-actin associated with the cytoplasmic side of the adherent membrane was reduced in WIP$^{-/-}$ T cells and did not increase after CD3 ligation. Furthermore, actin filaments associated with adherent membranes were sparse, disrupted and disorganized (FIG. 8A). Disruption of the actin network is likely to explain the T cell defect in WIP$^{-/-}$ mice.

Cross-linking of the BCR has been reported to cause its translocation to lipid rafts and its association with the cytoskeleton in a detergent insoluble fraction(Braun, J., et. al., (1982) *J. Immunol.* 128:1198–1204; Cheng, P. C., et. al., (1999) *J. Exp. Med.* 190:1549–1560; Jugloff, L. S., and Jongstra-Bilen, J. (1997) *J. Immunol.* 159:1096–1106). In spite of a reduced association of the actin cytoskeleton with the plasma membrane (FIG. 8B), B cells from WIP$^{-/-}$ mice exhibited increased proliferation and CD69 expression in response to ligation of the BCR, anti-CD40 and LPS. This indicates that WIP and an intact actin cytoskeleton are negative regulators of B cell activation. The opposite effect of WIP deficiency on the activation of T and B cells indicates that WIP and the actin network play fundamentally different roles in signaling by the TCR versus the BCR. While the TCR aggregates after stimulation, the BCR exists as an oligomer that is thought to dissociate following receptor ligation (Schamel, W. W., and Reth, M. (2000) *Immunity* 13:5–14). This dissociation is likely to be inhibited by actin filaments. Since WIP stabilizes actin filaments, it is likely that WIP normally inhibits BCR signaling. Furthermore, while inhibition of actin polymerization by cytochalasin blocks raft assembly following TCR ligation, translocation of the BCR into rafts following cross-linking is not affected (Cheng, P. C., et. al., (2001) *J. Immunol.* 166:3693–3701), and B cell proliferation in response to BCR ligation is enhanced (Rothstein, T. L. (1985) *J. Immunol.* 135:106–110).

It is likely that some of the functions of WASP and its homolog N-WASP are mediated by WIP. The ability of WASP to enhance TCR induction of NFAT activity and IL-2 expression, depends on the WIP binding WH1 region of WASP (Silvin, C., et al., (2001) *J. Biol. Chem* 276:21450–21457). It has been suggested that WASP/N-WASP and WIP function as a unit (Martinez-Quiles, N., et al., (2001) *Nat. Cell Biol.* 3:484–491). This would explain the similarities between the phenotype of WIP$^{-/-}$ mice and that of WAS patients and WASP-deficient mice. WASP-deficient T cells proliferate poorly and fail to increase their F-actin content to anti-CD3. However, there are important differences between the functions of WIP and WASP.

WASP/N-WASP enhance Arp2/3 dependent actin polymerization. In contrast, WIP diminishes N-WASP-mediated actin polymerization. Unlike WIP$^{-/-}$ mice, WASP$^{-/-}$ mice respond with a normal antibody response to TD antigens and their B cells do not hyper-proliferate in response to BCR ligation, anti-CD40 and LPS (Snapper, S. B., et al., (1998) *Immunity* 9:81–91; Zhang, J., et al., (1999) *J. Exp. Med.* 190:1329–1342). Furthermore, the proliferative defect to anti-CD3 in WASP$^{-/-}$ T cells may be incomplete (Zhang, J., et al., (1999) *J. Exp. Med.* 190:1329–1342) and is partially corrected by anti-CD28, whereas this defect is absolute in WIP$^{-/-}$ T cells and is not corrected by anti-CD28. This indicates that WASP and WIP can signal independently.

The findings herein show a critical role for WIP in T cell activation and immune synapse formation.

The relevant teachings of all the references, patents and patent applications cited herein are incorporated herein by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A transgenic mouse whose genome comprises a homozygous disruption of a WASP-Interacting Protein (WIP) gene, wherein the T cells of said transgenic mouse have a disrupted cortical actin network, and, following T cell receptor ligation, fail to:
   form an expanded interface with an antigen presenting cell;
   proliferate;
   secrete IL-2;
   increase F-actin content; and
   polarize and extend protrusions;
   and wherein the B cells of said transgenic mouse fail to undergo immunoglobulin IgG isotype switching following T cell-dependent antigen stimulation of said B cell.

2. The transgenic mouse of claim 1, wherein the disruption of the WASP-Interacting Protein (WIP) gene in the genome of said transgenic mouse is in a segment comprising exons 2 to 5 of the WASP-Interacting Protein (WIP) gene.

3. The transgenic mouse of claim 1, wherein the disruption of the WASP-Interacting Protein (WIP) gene in the genome of said transgenic mouse comprises a substitution of an exon of said WASP-Interacting Protein (WIP) gene with an exogenous nucleic acid sequence.

4. A method of producing a transgenic mouse whose genome comprises a homozygous disruption of a WASP-Interacting Protein (WIP) gene, said method comprising:
   a) introducing a targeting vector which disrupts the WASP-Interacting Protein (WIP) gene in an embryonic stem cell, thereby producing a transgenic embryonic stem cell with a disrupted WASP-Interacting Protein (WIP) gene;
   b) introducing the transgenic embryonic stem cell in a) into a blastocyst, thereby forming a chimeric blastocyst; and
   c) introducing the chimeric blastocyst of b) into the uterus of a pseudo-pregnant mouse, wherein said pseudo-pregnant mouse gives birth to a chimeric transgenic mouse whose genome comprises a disruption of the WASP-Interacting Protein (WIP) gene;
   d) breeding the chimeric transgenic mouse with a second mouse to generate F1 progeny having a heterozygous disruption of the WASP-Interacting Protein (WIP) gene, and crossbreeding the F1 progeny to produce a transgenic mouse which lacks a functional WASP-Interacting Protein (WIP) gene due to a homozygous disruption of the WASP-Interacting Protein (WIP) gene, wherein the T cells of said transgenic mouse have a disrupted cortical actin network, and, following T cell receptor ligation, fail to:
      form an expanded interface with an antigen presenting cell;
      proliferate;
      secrete IL-2;
      increase F-actin content; and
      polarize and extend protrusions;
   and wherein the B cells of said transgenic mouse fail to undergo immunoglobulin IgG isotype switching following T cell-dependent antigen stimulation of said B cell.
thereby producing a transgenic mouse whose genome comprises a homozygous disruption of a WASP-Interacting Protein (WIP) gene.

5. The method of claim 4, further comprising selecting the transgenic embryonic stem cell whose genome comprises the disrupted WASP-Interacting Protein (WIP) gene following step a).

6. The transgenic mouse of claim 5, wherein the disruption of the WASP-Interacting Protein (WIP) gene in the genome of said transgenic mouse is in a segment comprising exons 2 to 5 of the WASP-Interacting Protein (WIP) gene.

7. The transgenic mouse of claim 5, wherein the disruption of the WASP-interacting Protein (WIP) gene in the genome of said transgenic mouse comprises a substitution of an exon of said WASP-Interacting Protein (WIP) gene with an exogenous nucleic acid sequence.

8. A transgenic mouse produced by the method of claim 5.

9. The method of claim 4, wherein the disruption of the WASP-Interacting Protein (WIP) gene in the genome of said transgenic mouse is in a segment comprising exons 2 to 5 of the WASP-Interacting Protein (WIP) gene.

10. A transgenic mouse produced by the method of claim 9.

11. The method of claim 4, wherein the disruption of the WASP-Interacting Protein (WIP) gene in the genome of said transgenic mouse comprises a substitution of an exon of said WASP-interacting Protein (WIP) gene with an exogenous nucleic acid sequence.

12. A transgenic mouse produced by the method of claim 11.

13. A transgenic mouse produced by the method of claim 4.

14. An isolated cell whose genome comprises a homozygous disruption of a WASP-Interacting Protein (WIP) gene, wherein the cell is isolated from a transgenic mouse whose genome comprises a homozygous disruption of a WASP-Interacting Protein (WIP) gene, wherein the T cells of said transgenic mouse have a disrupted cortical actin network, and, following T cell receptor ligation, fail to:
   form an expanded interface with an antigen presenting cell;
   proliferate;
   secrete IL-2;
   increase F-actin content; and
   polarize and extend protrusions;
and wherein the B cells of said transgenic mouse fail to undergo immunoglobulin IgG isotype switching following T cell-dependent antigen stimulation of said B cell.

15. An isolated T cell whose genome comprises a homozygous disruption of a WASP-Interacting Protein (WIP) gene, wherein the T cell is isolated from a transgenic mouse whose genome comprises a homozygous disruption of a WASP-Interacting Protein (WIP) gene, and wherein the T cell has a disrupted cortical actin network, and, following T cell receptor ligation, fails to:
   form an expanded interface with an antigen presenting cell;
   proliferate;
   secrete IL-2;
   increase F-actin content; and
   polarize and extend protrusions.

16. An isolated B cell whose genome comprises a homozygous disruption of a WASP-Interacting Protein (WIP) gene, wherein the B cell is isolated from a transgenic mouse whose genome comprises a homozygous disruption of a WASP-Interacting Protein (WIP) gene, and wherein the B cell fails to undergo immunoglobulin IgG isotype switching following T cell-dependent antigen stimulation of said B cell.

17. A transgenic mouse whose genome comprises a heterozygous disruption of a WASP-Interacting Protein (WIP) gene, wherein disruption of the WASP-Interacting Protein (WIP) gene in a homozygous state results in a transgenic mouse having T cells having a disrupted cortical actin network, and, which following T cell receptor ligation, fail to:
   form an expanded interface with an antigen presenting cell;
   proliferate;
   secrete IL-2;
   increase F-actin content; and
   polarize and extend protrusions;
and B cells which fail to undergo immunoglobulin IgG isotype switching following T cell-dependent antigen stimulation of said B cell.

18. The transgenic mouse of claim 17, wherein the disruption of the WASP-Interacting Protein (WIP) gene in the genome of said transgenic mouse is in a segment comprising exons 2 to 5 of the WASP-Interacting Protein (WIP) gene.

19. The transgenic mouse of claim 17, wherein the disruption of the WASP-Interacting Protein (WIP) gene in the genome of said transgenic mouse comprises a substitution of an exon of said WASP-Interacting Protein (WIP) gene with an exogenous nucleic acid sequence.

20. A method of producing the transgenic mouse whose genome comprises a heterozygous disruption of a WASP-Interacting Protein (WIP) gene of claim 17, said method comprising:
   a) introducing a targeting vector which disrupts the WASP-Interacting Protein (WIP) gene in an embryonic stem cell, thereby producing a transgenic embryonic stem cell with a disrupted WASP-Interacting Protein (WIP) gene;
   b) introducing the transgenic embryonic stem cell in a) into a blastocyst, thereby forming a chimeric blastocyst; and
   c) introducing the chimeric blastocyst of b) into the uterus of a pseudo-pregnant mouse, wherein said pseudo-pregnant mouse gives birth to a chimeric transgenic mouse whose genome comprises a disruption of the WASP-Interacting Protein (WIP) gene;
   d) breeding the chimeric transgenic mouse with a second mouse to generate F1 progeny having a heterozygous disruption of the WASP-Interacting Protein (WIP) gene.

21. The method of claim 20, further comprising selecting the transgenic embryonic stem cell whose genome comprises the disrupted WASP-Interacting Protein (WIP) gene following step a).

22. A transgenic mouse produced by the method of claim 21.

23. The method of claim 20, wherein the disruption of the WASP-Interacting Protein (WIP) gene in the genome of said transgenic mouse is in a segment comprising exons 2 to 5 of the WASP-Interacting Protein (WIP) gene.

24. A transgenic mouse produced by the method of claim 23.

25. The method of claim 20, wherein the disruption of the WASP-Interacting Protein (WIP) gene in the genome of said transgenic mouse comprises a substitution of an exon of said WASP-Interacting Protein (WIP) gene with an exogenous nucleic acid sequence.

26. A transgenic mouse produced by the method of claim 25.

27. A transgenic mouse produced by the method of claim 20.

28. An isolated cell whose genome comprises a heterozygous disruption of a WASP-Interacting Protein (WIP) gene, wherein the cell is isolated from the transgenic mouse of claim 17.

29. The isolated cell of claim 28, wherein the cell is a T cell.

30. The isolated cell of claim 28, wherein the cell is a B cell.

* * * * *

UNITED STATES PATENT AND TRADEMARK OFFICE
CERTIFICATE OF CORRECTION

| | | |
|---|---|---|
| PATENT NO. | : 6,927,318 B2 | Page 1 of 1 |
| APPLICATION NO. | : 10/078547 | |
| DATED | : August 9, 2005 | |
| INVENTOR(S) | : Narayanaswamy Ramesh et al. | |

It is certified that error appears in the above-identified patent and that said Letters Patent is hereby corrected as shown below:

Col. 69, Line 46, delete "The transgenic mouse" insert --The method--

Col. 69, Line 50, delete "The transgenic mouse" insert --The method--

Col. 69, Line 51, Claim 7, delete "WASP-interacting Protein" insert --WASP-Interacting Protein--

Signed and Sealed this

Twenty-ninth Day of July, 2008

JON W. DUDAS
*Director of the United States Patent and Trademark Office*